United States Patent
Yaari et al.

(10) Patent No.: US 12,285,188 B2
(45) Date of Patent: Apr. 29, 2025

(54) LAPAROSCOPIC WORKSPACE DEVICE

(71) Applicant: Ark Surgical Ltd., Nazareth (IL)

(72) Inventors: Abraham J. Yaari, Zikhron-Yaakov (IL); Stav Tori, Moshav Neve Yarak (IL)

(73) Assignee: Ark Surgical Ltd., Nazareth (IL)

( * ) Notice: Subject to any disclaimer, the term of this patent is extended or adjusted under 35 U.S.C. 154(b) by 471 days.

(21) Appl. No.: 16/645,803

(22) PCT Filed: Sep. 6, 2018

(86) PCT No.: PCT/IL2018/051014
§ 371 (c)(1),
(2) Date: Mar. 10, 2020

(87) PCT Pub. No.: WO2019/049152
PCT Pub. Date: Mar. 14, 2019

(65) Prior Publication Data
US 2020/0268410 A1    Aug. 27, 2020

Related U.S. Application Data

(63) Continuation-in-part of application No. PCT/IL2017/051015, filed on Sep. 10, 2017.
(Continued)

(51) Int. Cl.
*A61B 17/34*    (2006.01)
*A61B 17/00*    (2006.01)

(52) U.S. Cl.
CPC .... *A61B 17/3423* (2013.01); *A61B 17/00234* (2013.01); *A61B 17/3431* (2013.01);
(Continued)

(58) Field of Classification Search
CPC ............ A61B 17/3423; A61B 17/3431; A61B 17/3439; A61B 17/0218; A61B 17/0225;
(Continued)

(56) References Cited

U.S. PATENT DOCUMENTS 3,634,938 A    1/1972  Hutchinson
4,478,580 A    10/1984 Barrut
(Continued)

FOREIGN PATENT DOCUMENTS

AU    2012202287    5/2012
CN    1939224    4/2007
(Continued)

OTHER PUBLICATIONS

Invitation to Pay Additional Fees, Communication Relating to the Results of the Partial International Search and the Provisional Opinion Dated Apr. 8, 2022 From the International Searching Authority Re. Application No. PCT/IL2021/051499. (15 Pages).
(Continued)

*Primary Examiner* — Anu Ramana

(57) ABSTRACT

A workspace device comprising: (a) a workspace body having a workspace inner wall defining an internal volume, including one or more expandable segments, said workspace body is: collapsible to a collapsed state where said body fits through a laparoscopic passageway in an abdominal wall, which passageway extends to an abdominal cavity; and expandable, to increase said internal volume, to an expanded state within said cavity, where, in said expanded state said workspace body: has an opening to said internal volume; and extends axially from a proximal to a distal direction defining a workspace axis; (b) one or more channels sized and shaped to supply inflation fluid to said workspace body; (c) said workspace body including: a plurality of circumferentially extending inflatable segments; a fluid pathway connecting at least one of said one or more channels to at least one of said segments.

19 Claims, 63 Drawing Sheets

Related U.S. Application Data

(60) Provisional application No. 62/642,741, filed on Mar. 14, 2018, provisional application No. 62/393,015, filed on Sep. 10, 2016.

(52) U.S. Cl.
CPC .. *A61B 17/3439* (2013.01); *A61B 2017/0003* (2013.01); *A61B 2017/00287* (2013.01); *A61B 2017/00336* (2013.01); *A61B 2017/00557* (2013.01); *A61B 2017/00867* (2013.01); *A61B 2017/3433* (2013.01)

(58) Field of Classification Search
CPC .. A61B 2017/00557; A61B 2017/3433; A61B 2017/3486; A61B 2017/22051
See application file for complete search history.

(56) References Cited

U.S. PATENT DOCUMENTS

| | | | |
|---|---|---|---|
| 4,571,180 A | 2/1986 | Kulick | |
| 4,665,621 A | 5/1987 | Ackerman et al. | |
| 4,764,114 A | 8/1988 | Jeffcoat et al. | |
| 4,790,751 A | 12/1988 | Reinhardt et al. | |
| 4,873,651 A | 10/1989 | Raviv | |
| 4,883,425 A | 11/1989 | Zimble | |
| 4,935,635 A | 6/1990 | O'Harra | |
| 5,051,823 A | 9/1991 | Cooper et al. | |
| 5,176,687 A | 1/1993 | Hasson et al. | |
| 5,178,537 A | 1/1993 | Currie | |
| 5,215,521 A | 6/1993 | Cochran et al. | |
| 5,224,049 A | 6/1993 | Mushabac | |
| 5,230,621 A | 7/1993 | Jacoby | |
| 5,244,387 A | 9/1993 | Fuierer | |
| 5,257,184 A | 10/1993 | Mushabac | |
| 5,308,327 A | 5/1994 | Heaven et al. | |
| 5,313,053 A | 5/1994 | Koenck et al. | |
| 5,318,442 A | 6/1994 | Jeffcoat et al. | |
| 5,320,462 A | 6/1994 | Johansson et al. | |
| 5,361,752 A | 11/1994 | Moll et al. | |
| 5,368,597 A | 11/1994 | Pagedas | |
| 5,372,502 A | 12/1994 | Massen et al. | |
| 5,423,677 A | 6/1995 | Brattesani | |
| 5,524,633 A | 6/1996 | Heaven et al. | |
| 5,618,296 A | 4/1997 | Sorensen et al. | |
| 5,743,731 A | 4/1998 | Lares et al. | |
| 5,850,289 A | 12/1998 | Fowler et al. | |
| 5,862,559 A | 1/1999 | Hunter | |
| 5,897,509 A | 4/1999 | Toda et al. | |
| 5,919,129 A | 7/1999 | Vandre | |
| 5,944,523 A | 8/1999 | Badoz | |
| 5,947,992 A | 9/1999 | Zadini et al. | |
| 5,969,321 A | 10/1999 | Danielson et al. | |
| 5,993,209 A | 11/1999 | Matoba et al. | |
| 6,000,939 A | 12/1999 | Ray et al. | |
| 6,007,333 A | 12/1999 | Callan et al. | |
| 6,116,899 A | 6/2000 | Takeuchi | |
| 6,142,936 A | 11/2000 | Beane et al. | |
| 6,179,611 B1 | 1/2001 | Everett et al. | |
| 6,276,934 B1 | 8/2001 | Rakocz | |
| 6,309,219 B1 | 10/2001 | Robert | |
| 6,406,440 B1 | 6/2002 | Stefanchik | |
| 6,423,803 B1 * | 7/2002 | Nagpal | C08F 283/06 526/333 |
| 6,468,079 B1 | 10/2002 | Fischer et al. | |
| 6,589,268 B1 | 7/2003 | McEwen | |
| 6,819,318 B1 | 11/2004 | Geng | |
| 6,885,464 B1 | 4/2005 | Pfeiffer et al. | |
| 6,942,679 B1 | 9/2005 | Terai | |
| 7,041,056 B2 | 5/2006 | Deslauriers et al. | |
| 7,056,329 B2 | 6/2006 | Kerr | |
| 7,097,648 B1 * | 8/2006 | Globerman | A61B 17/22032 606/86 R |
| 7,235,066 B1 | 7/2007 | Narini et al. | |
| 7,346,417 B2 | 3/2008 | Lueth et al. | |
| 7,494,338 B2 | 2/2009 | Durbin et al. | |
| 7,625,335 B2 | 12/2009 | Deichmann et al. | |
| 7,668,583 B2 | 2/2010 | Fegert et al. | |
| 7,766,823 B2 | 8/2010 | Moll | |
| 7,813,591 B2 | 10/2010 | Paley et al. | |
| 8,280,152 B2 | 10/2012 | Thiel et al. | |
| 8,287,561 B2 * | 10/2012 | Nunez | A61B 17/07207 227/180.1 |
| 8,371,848 B2 | 2/2013 | Okawa et al. | |
| 8,744,194 B2 | 6/2014 | Kawasaki et al. | |
| 8,764,646 B2 | 7/2014 | Grundeman | |
| 8,936,470 B2 | 1/2015 | Pruckner et al. | |
| 9,137,511 B1 | 9/2015 | LeGrand, III et al. | |
| 9,179,987 B2 | 11/2015 | Goodacre | |
| 9,463,081 B2 | 10/2016 | Urakabe | |
| 9,522,054 B2 | 12/2016 | Kim et al. | |
| 9,603,675 B2 | 3/2017 | Pruckner | |
| 9,918,805 B2 | 3/2018 | Pruckner | |
| 10,136,970 B2 | 11/2018 | Pesach | |
| 10,182,875 B2 * | 1/2019 | Yates | A61B 90/03 |
| 10,206,666 B2 * | 2/2019 | Dickson | A61B 17/32053 |
| 10,226,599 B2 * | 3/2019 | Schaffer | A61M 25/1002 |
| 10,299,880 B2 | 5/2019 | Ramirez Luna et al. | |
| 10,470,846 B2 | 11/2019 | Kopelman et al. | |
| 10,695,150 B2 | 6/2020 | Kopelman et al. | |
| 11,253,239 B2 | 2/2022 | Bar-Yoseph et al. | |
| 2002/0103420 A1 | 8/2002 | Coleman et al. | |
| 2002/0133096 A1 | 9/2002 | Toda et al. | |
| 2004/0087937 A1 | 5/2004 | Eggers et al. | |
| 2004/0097792 A1 | 5/2004 | Moll et al. | |
| 2004/0106868 A1 | 6/2004 | Liew et al. | |
| 2004/0158261 A1 | 8/2004 | Vu | |
| 2005/0116673 A1 | 6/2005 | Carl et al. | |
| 2006/0154198 A1 | 7/2006 | Durbin et al. | |
| 2007/0037125 A1 | 2/2007 | Maev et al. | |
| 2007/0042315 A1 | 2/2007 | Boutoussov et al. | |
| 2007/0064242 A1 | 3/2007 | Childers | |
| 2007/0065782 A1 | 3/2007 | Maschke | |
| 2007/0172112 A1 | 7/2007 | Paley et al. | |
| 2007/0225744 A1 | 9/2007 | Nobles et al. | |
| 2007/0260231 A1 | 11/2007 | Rose et al. | |
| 2008/0002011 A1 | 1/2008 | Mizutani et al. | |
| 2008/0002869 A1 | 1/2008 | Scharlack et al. | |
| 2008/0038688 A1 | 2/2008 | Kopelman et al. | |
| 2008/0051817 A1 | 2/2008 | Leahy | |
| 2008/0145817 A1 | 6/2008 | Brennan et al. | |
| 2008/0160477 A1 | 7/2008 | Stookey et al. | |
| 2008/0201101 A1 | 8/2008 | Hebert et al. | |
| 2008/0261165 A1 | 10/2008 | Steingart et al. | |
| 2009/0017416 A1 | 1/2009 | Nguyen et al. | |
| 2009/0043314 A1 | 2/2009 | Sevensson et al. | |
| 2009/0061383 A1 | 3/2009 | Kang | |
| 2009/0087050 A1 | 4/2009 | Gandyra | |
| 2009/0306506 A1 | 12/2009 | Heger et al. | |
| 2009/0326383 A1 | 12/2009 | Barnes et al. | |
| 2010/0047733 A1 | 2/2010 | Nahlieli | |
| 2010/0092908 A1 | 4/2010 | Rothenwaender et al. | |
| 2010/0189341 A1 | 7/2010 | Oota et al. | |
| 2010/0238279 A1 | 9/2010 | Thoms et al. | |
| 2010/0239136 A1 | 9/2010 | Gandyra et al. | |
| 2010/0239996 A1 | 9/2010 | Ertl | |
| 2010/0268069 A1 | 10/2010 | Liang | |
| 2010/0268071 A1 | 10/2010 | Kim | |
| 2010/0305435 A1 | 12/2010 | Magill | |
| 2011/0087235 A1 | 4/2011 | Taylor et al. | |
| 2011/0184245 A1 * | 7/2011 | Xia | A61B 1/32 600/202 |
| 2011/0184432 A1 * | 7/2011 | Parihar | A61B 17/00234 606/114 |
| 2011/0190781 A1 | 8/2011 | Collier et al. | |
| 2011/0301419 A1 | 12/2011 | Craft et al. | |
| 2012/0015329 A1 | 1/2012 | Gross et al. | |
| 2012/0040305 A1 | 2/2012 | Karazivan et al. | |
| 2012/0046536 A1 | 2/2012 | Cheung et al. | |
| 2012/0097002 A1 | 4/2012 | Thiedig | |
| 2012/0179281 A1 | 7/2012 | Steingart et al. | |
| 2012/0189182 A1 | 7/2012 | Liang et al. | |
| 2012/0270177 A1 | 10/2012 | Nakashima et al. | |
| 2012/0271176 A1 | 10/2012 | Moghaddam et al. | |

(56) References Cited

U.S. PATENT DOCUMENTS

| | | |
|---|---|---|
| 2013/0000666 A1 | 1/2013 | Hu |
| 2013/0017507 A1 | 1/2013 | Moffson et al. |
| 2013/0027515 A1 | 1/2013 | Vinther et al. |
| 2013/0188012 A1 | 7/2013 | Bellis et al. |
| 2013/0209953 A1 | 8/2013 | Arlinsky et al. |
| 2013/0253278 A1 | 9/2013 | Smith |
| 2013/0273492 A1 | 10/2013 | Suttin, Sr. et al. |
| 2014/0066784 A1 | 3/2014 | Yokota |
| 2014/0093835 A1 | 4/2014 | Levin |
| 2014/0111616 A1 | 4/2014 | Blayvas |
| 2014/0120492 A1 | 5/2014 | Loannidis et al. |
| 2014/0120493 A1 | 5/2014 | Levin |
| 2014/0146142 A1 | 5/2014 | Duret et al. |
| 2014/0178832 A1 | 6/2014 | Choi et al. |
| 2014/0194696 A1 | 7/2014 | Fischvogt |
| 2014/0199650 A1 | 7/2014 | Moffson et al. |
| 2014/0221819 A1 | 8/2014 | Sarment |
| 2014/0276055 A1 | 8/2014 | Barthe et al. |
| 2014/0248577 A1 | 9/2014 | Tahmasebi et al. |
| 2014/0275801 A1 | 9/2014 | Menchaca |
| 2014/0309523 A1 | 10/2014 | Daon et al. |
| 2014/0330285 A1 | 11/2014 | Rosenblatt et al. |
| 2014/0343395 A1 | 11/2014 | Choi et al. |
| 2015/0015701 A1 | 1/2015 | Yu |
| 2015/0118638 A1 | 4/2015 | Cowburn |
| 2015/0182299 A1 | 7/2015 | Koubi et al. |
| 2015/0223910 A1 | 8/2015 | Pruckner |
| 2015/0223916 A1 | 8/2015 | Kim et al. |
| 2015/0229911 A1 | 8/2015 | Ge et al. |
| 2015/0297254 A1 | 10/2015 | Sullivan et al. |
| 2015/0348320 A1 | 12/2015 | Pesach et al. |
| 2016/0100857 A1 | 4/2016 | Wachli et al. |
| 2016/0120615 A1 | 5/2016 | Scurtescu |
| 2016/0259515 A1 | 9/2016 | Sabina et al. |
| 2016/0262856 A1 | 9/2016 | Atiya et al. |
| 2016/0270878 A1 | 9/2016 | Fulton, III |
| 2016/0302783 A1 | 10/2016 | Greenberg et al. |
| 2016/0338682 A1 | 11/2016 | Hoyte et al. |
| 2016/0338803 A1 | 11/2016 | Pesach |
| 2017/0007377 A1 | 1/2017 | Pesach et al. |
| 2017/0079708 A1 | 3/2017 | Gilbert et al. |
| 2017/0128059 A1 | 5/2017 | Coe et al. |
| 2017/0202483 A1 | 7/2017 | Sorimoto et al. |
| 2017/0252026 A1 | 9/2017 | Gupta et al. |
| 2018/0008250 A1 | 1/2018 | Joseph |
| 2018/0049830 A1* | 2/2018 | Yates ............... A61B 34/35 |
| 2018/0360481 A1 | 12/2018 | Bonadio et al. |
| 2019/0117241 A1 | 4/2019 | Sherman et al. |
| 2019/0192262 A1 | 6/2019 | Pesach |
| 2019/0247033 A1 | 8/2019 | Yaari |
| 2019/0262098 A1 | 8/2019 | Pesach et al. |
| 2019/0328376 A1 | 10/2019 | Bar-Yoseph et al. |
| 2019/0343598 A1 | 11/2019 | Knobel et al. |
| 2020/0060550 A1 | 2/2020 | Pesach et al. |
| 2020/0155285 A1 | 5/2020 | Pesach et al. |
| 2022/0071737 A1 | 3/2022 | Pesach et al. |
| 2022/0160342 A1 | 5/2022 | Bar-Yoseph et al. |

FOREIGN PATENT DOCUMENTS

| | | |
|---|---|---|
| CN | 101677757 | 3/2010 |
| EP | 1707130 | 10/2006 |
| EP | 1901033 | 3/2008 |
| EP | 2165674 | 3/2010 |
| EP | 2485664 | 8/2012 |
| EP | 2630929 | 6/2016 |
| EP | 3558143 | 8/2021 |
| ES | 2115544 | 6/1998 |
| FR | 2692773 | 12/1993 |
| GB | 2495522 | 3/2013 |
| JP | 63-005742 | 1/1988 |
| JP | 07-155297 | 6/1995 |
| JP | 10-165425 | 6/1998 |
| JP | H10-262996 | 10/1998 |
| JP | 11-192207 | 7/1999 |
| JP | 2002-125927 | 5/2002 |
| JP | 2003-325451 | 11/2003 |
| JP | 2006-102497 | 4/2006 |
| JP | 2007-152004 | 6/2007 |
| JP | 2007-296249 | 11/2007 |
| JP | 2009-268614 | 11/2009 |
| JP | 2010-104652 | 5/2010 |
| JP | 2012-016573 | 1/2012 |
| JP | 5016311 | 6/2012 |
| JP | 2014-236957 | 12/2014 |
| JP | 5661255 | 1/2015 |
| KR | 10-1782740 | 9/2017 |
| WO | WO 98/06352 | 2/1998 |
| WO | WO 98/09569 | 3/1998 |
| WO | WO-2004002327 A1 * | 1/2004 ............. A61B 17/02 |
| WO | WO 2005/104959 | 11/2005 |
| WO | WO 2007/063980 | 6/2007 |
| WO | WO 2008/013181 | 1/2008 |
| WO | WO 2014/020247 | 2/2014 |
| WO | WO 2014/102779 | 7/2014 |
| WO | WO 2015/028646 | 3/2015 |
| WO | WO 2015/084769 | 6/2015 |
| WO | WO 2015/107520 | 7/2015 |
| WO | WO 2016/028429 | 2/2016 |
| WO | WO 2016/028789 | 2/2016 |
| WO | WO 2016/064617 | 4/2016 |
| WO | WO 2016/068825 | 5/2016 |
| WO | WO 2016/110855 | 7/2016 |
| WO | WO 2016/113745 | 7/2016 |
| WO | WO 2016/178212 | 11/2016 |
| WO | WO 2017/125926 | 7/2017 |
| WO | WO 2017/216803 | 12/2017 |
| WO | WO 2018/047180 | 8/2018 |
| WO | WO 2019/008586 | 1/2019 |
| WO | WO 2019/021285 | 1/2019 |
| WO | WO 2019/049152 | 3/2019 |
| WO | WO 2020/144692 | 7/2020 |
| WO | WO 2022/130385 | 6/2022 |

OTHER PUBLICATIONS

Communication Pursuant to Article 94(3) EPC Dated Jan. 29, 2021 From the European Patent Office Re. Application No. 18769813.9. (9 Pages).
Final Official Action Dated Apr. 12, 2021 From the US Patent and Trademark Office Re. U.S. Appl. No. 16/310,435. (19 Pages).
International Preliminary Report on Patentability Dated Dec. 27, 2018 From the International Bureau of WIPO Re. Application No. PCT/IL2017/050674. (9 Pages).
International Search Report and the Written Opinion Dated Sep. 18, 2017 From the International Searching Authority Re. Application No. PCT/IL2017/050674. (12 Pages).
Notice of Allowance Dated Dec. 15, 2021 from US Patent and Trademark Office Re. U.S. Appl. No. 16/310,435. (6 pages).
Official Action Dated Aug. 19, 2021 From the US Patent and Trademark Office Re. U.S. Appl. No. 16/310,435. (7 Pages).
Official Action Dated Oct. 27, 2020 From the US Patent and Trademark Office Re. U.S. Appl. No. 16/310,435. (11 Pages).
Supplementary European Search Report and the European Search Opinion Dated Jan. 21, 2020 From the European Patent Office Re. Application No. 17812894.8. (10 Pages).
Bar-Yoseph et al.
Restriction Official Action Dated May 17, 2022 from US Patent and Trademark Office Re. U.S. Appl. No. 16/331,974. (10 pages).
Summons to Attend Oral Proceedings Pursuant to Rule 115(1) EPC Dated Mar. 19, 2021 From the European Patent Office Re. Application No. 17780530.6. (7 Pages).
Communication Pursuant to Article 94(3) EPC Dated Jan. 31, 2020 From the European Patent Office Re. Application No. 17780530.6. (3 Pages).
International Preliminary Report on Patentability Dated Mar. 19, 2020 From the International Bureau of WIPO Re. Application No. PCT/IL2017/051014. (10 Pages).
International Preliminary Report on Patentability Dated Mar. 21, 2019 From the International Bureau of WIPO Re. Application No. PCT/IL2017/051015. (13 Pages).

(56) References Cited

OTHER PUBLICATIONS

International Search Report and the Written Opinion Dated Dec. 11, 2018 From the International Searching Authority Re. Application No. PCT/IL2017/051014. (18 Pages).
International Search Report and the Written Opinion Dated Jan. 24, 2018 From the International Searching Authority Re. Application No. PCT/IL2017/051015. (23 Pages).
Invitation to Pay Additional Fees, Communication Relating to the Results of the Partial International Search and the Provisional Opinion Dated Nov. 17, 2017 From the International Searching Authority Re. Application No. PCT/IL2017/051015. (17 Pages).
Communication Pursuant to Article 94(3) EPC Dated Nov. 16, 2021 From the European Patent Office Re. Application No. 17707964.7. (4 Pages).
Applicant-Initiated Interview Summary Dated Aug. 2, 2017 From the US Patent and Trademark Office Re. U.S. Appl. No. 15/115,196. (3 pages).
Communication Pursuant to Article 94(3) EPC Dated Oct. 5, 2021 From the European Patent Office Re. Application No. 18759184.7. (6 Pages).
Communication Pursuant to Article 94(3) EPC Dated Aug. 10, 2017 From the European Patent Office Re. Application No. 13830124.7. (6 Pages).
Communication Pursuant to Article 94(3) EPC Dated Nov. 19, 2018 From the European Patent Office Re. Application No. 13830124.7. (8 Pages).
Communication Pursuant to Article 94(3) EPC Dated Nov. 19, 2020 From the European Patent Office Re. Application No. 13830124.7. (6 Pages).
Communication Pursuant to Article 94(3) EPC Dated Nov. 30, 2021 From the European Patent Office Re. Application No. 17780530.6. (4 Pages).
Communication Pursuant to Rules 70(2) and 70a(2) EPC Dated Sep. 7, 2018 From the European Patent Office Re. Application No. 16789407.0. (1 Page).
Communication Relating to the Results of the Partial International Search and the Provisional Opinion Dated Jun. 14, 2017 From the International Searching Authority Re. Application No. PCT/IL2017/050072. (12 Pages).
Communication Relating to the Results of the Partial International Search Dated May 8, 2014 From the International Searching Authority Re. Application No. PCT/IL2013/051059.
Decision of Rejection Dated Jan. 14, 2020 From the Japan Patent Office Re. Application No. 2017-228103 and Its Translation Into English. (7 Pages).
English Translation Dated Nov. 30, 2021 of Ground(s) of Reason of Rejection Dated Nov. 19, 2021 From the Korean Intellectual Property Office Re. Application No. 2010-7032325. (2 Pages).
European Search Report and the European Search Opinion Dated Feb. 4, 2020 From the European Patent Office Re. Application 19211372.8. (10 Pages).
Final Official Action Dated Dec. 28, 2020 from the US Patent and Trademark Office Re. U.S. Appl. No. 16/634,152. (29 pages).
Ground(s) of Reason of Rejection Dated Nov. 19, 2021 From the Korean Intellectual Property Office Re. Application No. 2010-7032325. (2 Pages).
International Preliminary Report on Patentability Dated Aug. 2, 2018 From the International Bureau of WIPO Re. Application No. PCT/IL2017/050072. (10 Pages).
International Preliminary Report on Patentability Dated Feb. 6, 2020 From the International Bureau of WIPO Re. Application No. PCT/IL2018/050825. (10 Pages).
International Preliminary Report on Patentability Dated Jul. 9, 2015 From the International Bureau of WIPO Re. Application No. PCT/IL2013/051059.
International Preliminary Report on Patentability Dated Jan. 16, 2020 From the International Bureau of WIPO Re. Application No. PCT/IL2018/050731. (9 Pages).
International Preliminary Report on Patentability Dated Nov. 16, 2017 From the International Bureau of WIPO Re. Application No. PCT/IL2016/050449. (11 Pages).
International Preliminary Report on Patentability Dated Jul. 20, 2017 From the International Bureau of WIPO Re. Application No. PCT/IL2016/050023. (10 Pages).
International Preliminary Report on Patentability Dated Jul. 22, 2021 From the International Bureau of WIPO Re. Application No. PCT/IL2020/050040. (10 Pages).
International Preliminary Report on Patentability Dated Jul. 27, 2017 From the International Bureau of WIPO Re. Application No. PCT/IL2016/050058. (7 Pages).
International Search Report and the Written Opinion Dated Oct. 1, 2018 From the International Searching Authority Re. Application No. PCT/IL2018/050731. (16 Pages).
International Search Report and the Written Opinion Dated Sep. 2, 2014 From the International Searching Authority Re. Application No. PCT/IL2013/051059.
International Search Report and the Written Opinion Dated Nov. 7, 2018 From the International Searching Authority Re. Application No. PCT/IL2018/050825. (17 Pages).
International Search Report and the Written Opinion Dated Aug. 8, 2017 From the International Searching Authority Re. Application No. PCT/IL2017/050072. (17 Pages).
International Search Report and the Written Opinion Dated Apr. 18, 2016 From the International Searching Authority Re. Application No. PCT/IL2016/050058.
International Search Report and the Written Opinion Dated Apr. 21, 2016 From the International Searching Authority Re. Application No. PCT/IL2016/050023.
International Search Report and the Written Opinion Dated Aug. 23, 2016 From the International Searching Authority Re. Application No. PCT/IL2016/050449.
International Search Report and the Written Opinion Dated Jul. 23, 2020 From the International Searching Authority Re. Application No. PCT/IL2020/050040. (14 Pages).
Invitation to Pay Additional Fees Dated May 12, 2020 From the International Searching Authority Re. Application No. PCT/IL2020/050040. (3 Pages).
Notice of Allowance Dated Aug. 9, 2018 From the US Patent and Trademark Office Re. U.S. Appl. No. 15/571,231. (17 pages).
Notice of Allowance Dated Jul. 11, 2018 From the US Patent and Trademark Office Re. U.S. Appl. No. 15/115,196. (8 pages).
Notice of Allowance Dated May 12, 2016 From the US Patent and Trademark Office Re. U.S. Appl. No. 14/655,286.
Notice of Allowance Dated Jul. 13, 2021 from the US Patent and Trademark Office Re. U.S. Appl. No. 16/227,995. (7 pages).
Notice of Allowance Dated Nov. 30, 2020 from the US Patent and Trademark Office Re. U.S. Appl. No. 16/071,058. (10 pages).
Notice of Reasons for Rejection Dated May 7, 2019 From the Japan Patent Office Re. Application No. 2017-228103 and Its Translation Into English. (8 Pages).
Notice of Reasons for Rejection Dated Jul. 11, 2017 From the Japan Patent Office Re. Application No. 2015-548888 and Its Translation Into English. (5 Pages).
Notice of Reasons for Rejection Dated Feb. 14, 2017 From the Japan Patent Office Re. Application No. 2015-548888 and Its Translation Into English. (10 Pages).
Notice of Reasons for Rejection Dated Sep. 25, 2018 From the Japan Patent Office Re. Application No. 2017-228103 and Its Translation Into English. (15 Pages).
Notice Requesting Submission of Opinion Dated Feb. 3, 2021 From the Korean Intellectual Property Office Re. Application No. 10-2020-7032325 and Its Translation Into English. (14 Pages).
Notice Requesting Submission of Opinion Dated Jan. 21, 2020 From the Korean Intellectual Property Office Re. Application No. 10-2019-7034814. (3 Pages).
Notice Requesting Submission of Opinion Dated Apr. 26, 2019 From the Korean Intellectual Property Office Re. Application No. 10-2015-7020305. (4 Pages).
Notification of Office Action and Search Report Dated Jan. 5, 2017 From the State Intellectual Property Office of the People's Republic of China Re. Application No. 201380071840.0. (7 Pages).

(56) References Cited

OTHER PUBLICATIONS

Notification of Office Action Dated Apr. 15, 2016 From the State Intellectual Property Office of the People's Republic of China Re. Application No. 201380071840.0.
Office Action Dated Aug. 6, 2019 From the Israel Patent Office Re. Application No. 264237 and Its Translation Into English. (6 Pages).
Official Action Dated Sep. 3, 2021 from the US Patent and Trademark Office Re. Application No. 16/634, 152. (43 pages).
Official Action Dated Nov. 4, 2020 From the US Patent and Trademark Office Re. U.S. Appl. No. 15/274,756. (19 Pages).
Official Action Dated Mar. 9, 2017 From the US Patent and Trademark Office Re. U.S. Appl. No. 15/115,196. (26 pages).
Official Action Dated Jun. 12, 2020 from the US Patent and Trademark Office Re. Application No. 16/634, 152. (41 pages).
Official Action Dated Dec. 13, 2017 From the US Patent and Trademark Office Re. Application No. 15/115, 196. (26 pages).
Official Action Dated Jun. 13, 2019 From the US Patent and Trademark Office Re. U.S. Appl. No. 15/274,756. (39 pages).
Official Action Dated May 15, 2020 from the US Patent and Trademark Office Re. U.S. Appl. No. 16/071,058. (31 pages).
Official Action Dated Feb. 19, 2021 From the US Patent and Trademark Office Re. U.S. Appl. No. 16/227,995. (27 Pages).
Official Action Dated Sep. 28, 2016 From the US Patent and Trademark Office Re. U.S. Appl. No. 15/115,196. (19 pages).
Official Action Dated Apr. 3, 2020 from the US Patent and Trademark Office Re. U.S. Appl. No. 16/199,954. (31 pages).
Requisition by the Examiner Dated Oct. 4, 2019 From the Innovation, Science and Economic Development Canada, Canadian Intellectual Property Office Re. Application No. 2,896,210. (3 Pages).
Restriction Official Action Dated Nov. 14, 2019 From the US Patent and Trademark Office Re. U.S. Appl. No. 16/199,954. (6 pages).
Restriction Official Action Dated Sep. 26, 2018 From the US Patent and Trademark Office Re. U.S. Appl. No. 15/274,756. (10 Pages).
Summons to Attend Oral Proceedings Pursuant to Rule 115(1) EPC Dated Mar. 19, 2020 From the European Patent Office Re. Application No. 13830124.7. (13 Pages).
Supplementary European Search Report and the European Search Opinion Dated Feb. 19, 2021 From the European Patent Office Re. Application No. 18837606.5. (7 Pages).
Supplementary European Search Report and the European Search Opinion Dated Aug. 21, 2018 From the European Patent Office Re. Application No. 16789407.0. (6 Pages).
Translation Dated Feb. 2, 2020 of Notice Requesting Submission of Opinion Dated Jan. 21, 2020 From the Korean Intellectual Property Office Re. Application No. 10-2019-7034814. (3 Pages).
Translation Dated May 9, 2019 of Notice Requesting Submission of Opinion Dated Apr. 26, 2019 From the Korean Intellectual Property Office Re. Application No. 10-2015-7020305. (4 Pages).
Translation Dated Nov. 30, 2021 of Ground(s) of Reason of Rejection Dated Nov. 19, 2021 From the Korean Intellectual Property Office Re. Application No. 2010-7032325. (2 Pages).
Translation of Notification of Apr. 15, 2016 From the State Intellectual Property Office of the People's Republic of China Re. Application No. 201380071840.0.
Translation of Notification of Office Action Dated Jan. 5, 2017 From the State Intellectual Property Office of the People's Republic of China Re. Application No. 201380071840.0. (4 Pages).
Bouguet et al. "3D Photography Using Shadows in Dual-Space Geometry", The International Journal of Computer Vision, 35(2): 129-149, Nov./Dec. 1999.
Fluegge et al. "Precision of Intraoral Digital Dental Impressions With iTero and Extraoral Digitization With the iTero and a Model Scanner", American Journal of Orthodontics and Dentofacial Orthopedics, 144(3): 471-478, Sep. 2013.
Geng "Structured-Light 3D Surface Imaging: A Tutorial", Advances in Optics and Photonics, 3: 128-160, 2011.
Goshtasby et al. "A System for Digital Reconstruction of Gypsum Dental Casts", IEEE Transactions on Medical Imaging, 16(5): , Oct. 1997.

Logozzo et al. "Recent Advances in Dental Optics—Part I: 3D Intraoral Scanners for Restorative Dentistry", Optics and Lasers in Engineering, 54: 203-221, Mar. 2014.
Maintz et al. "A Survey of Medical Image Registration", Medical Image Analysis, 2(1): 1-36, Mar. 1998.
Medeiros et al. "Coded Structred Light for 3D-Photography: An Overview", IEEE-RITA, (Latin-American Learning Technologies Journal), IV(2): 109-124, Jul. 1999.
OmniVision "OVM6946 400x400. Compact, Cost-Effective Wafer-Level Camera Module for Single-Use Endoscopes", Omni Vision, Product Brief, 2 P., Aug. 10, 2016.
Paperno et al. "A New Method for Magnetic Position and Orientation Tracking", IEEE Transactions on Magnetics, XP011033696, 37(4): 1938-1940, Jul. 2001.
Salvi et al. "Pattern Codification Strategies in Structured Light Systems", Pattern Recognition, 37(4): 827-849, 2004.
Savarese et al. "3D Reconstruction by Shadow Carving: Theory and Practical Evaluation", International Journal of Computer Vision, 71(3): 305-336, Published Online Jun. 1, 2006.
Toshiba "IK-CT2: 0.7 x 0.7 mm, 220x220, CMOS", Toshiba Information Systems, Product Sheet, 1 P., Dec. 2016.
European Search Report and the European Search Opinion Dated Jan. 3, 2022 From the European Patent Office Re. Application No. 21200149.9. (10 Pages).
Communication Pursuant to Article 94(3) EPC Dated Oct. 7, 2020 From the European Patent Office Re. Application No. 177805300.6. (5 Pages).
International Search Report and the Written Opinion Dated Jul. 6, 2022 From the International Searching Authority Re. Application No. PCT/IL2021/051499. (24 Pages).
Summons to Attend Oral Proceedings Pursuant to Rule 115(1) EPC Dated Apr. 20, 2021 From the European Patent Office Re. Application No. 17780530.6. (2 Pages).
Summons to Attend Oral Proceedings Pursuant to Rule 115(1) EPC Dated Mar. 18, 2022 From the European Patent Office Re. Application No. 18769813.9. (9 Pages).
Communication Pursuant to Article 94(3) EPC Dated Jun. 22, 2023 From the European Patent Office Re. Application No. 17812894.8. (7 Pages).
Notice of Allowance Dated Mar. 7, 2023 from the US Patent and Trademark Office Re. U.S. Appl. No. 16/331,974. (14 pages).
Supplementary European Search Report and the European Search Opinion Dated Feb. 7, 2023 From the European Patent Office Re. Application No. 22213874.5. (11 Pages).
Communication Pursuant to Article 94(3) EPC Dated Mar. 10, 2023 From the European Patent Office Re. Application No. 17780530.6 (3 Pages).
Restriction Official Action Dated May 5, 2023 from the US Patent and Trademark Office Re. U.S. Appl. No. 17/670,56. (6 pages).
Official Action Dated May 14, 2024 from the US Patent and Trademark Office Re. U.S. Appl. No. 17/670,562. (26 pages).
Communication Pursuant to Article 94(3) EPC Dated Oct. 9, 2024 From the European Patent Office Re. Application No. 17812894.8. (7 Pages).
Interview Summary Dated Oct. 25, 2024 from the US Patent and Trademark Office Re. U.S. Appl. No. 17/670,562. (10 pages).
International Preliminary Report on Patentability Dated Jun. 29, 2023 From the International Bureau of WIPO Re. Application No. PCT/IL2021/051499 (15 Pages).
Official Action Dated Aug. 24, 2023 from the US Patent and Trademark Office Re. U.S. Appl. No. 17/670,562. (102 pages).
Decision to Refuse a European Patent Application Dated Oct. 18, 2022 From the European Patent Office Re. Application No. 18769813. 9. (15 Pages).
Official Action Dated Oct. 13, 2022 From the US Patent and Trademark Office Re. U.S. Appl. No. 16/331,974. (83 Pages).
Provision of the Minutes in Accordance With Rule 124(4) EPC Dated Oct. 12, 2022 From the European Patent Office Re. Application No. 18769813.9. (11 Pages).

\* cited by examiner

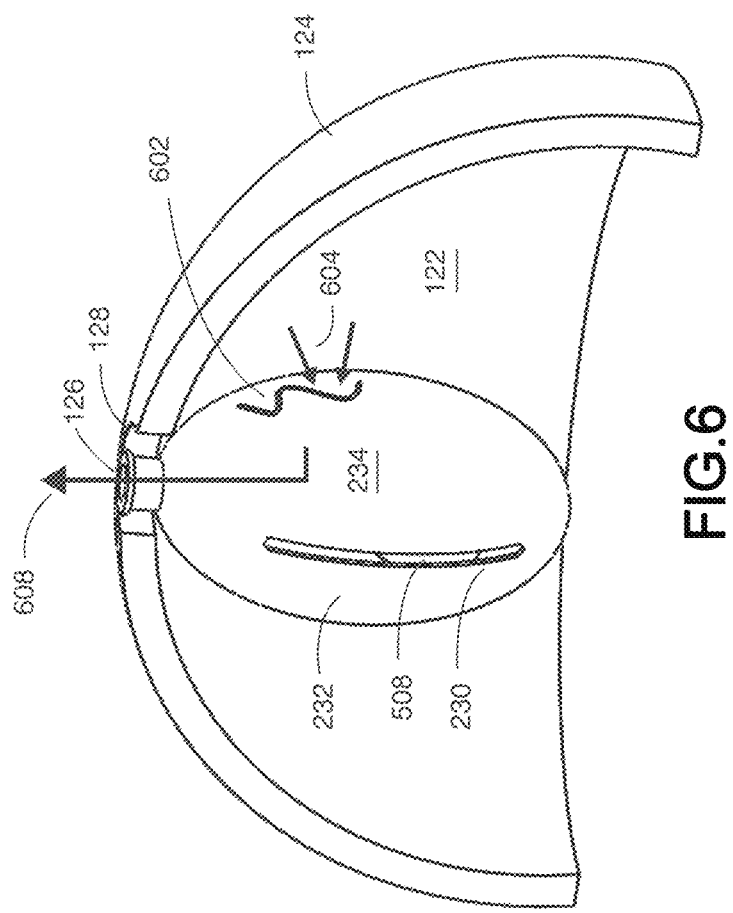

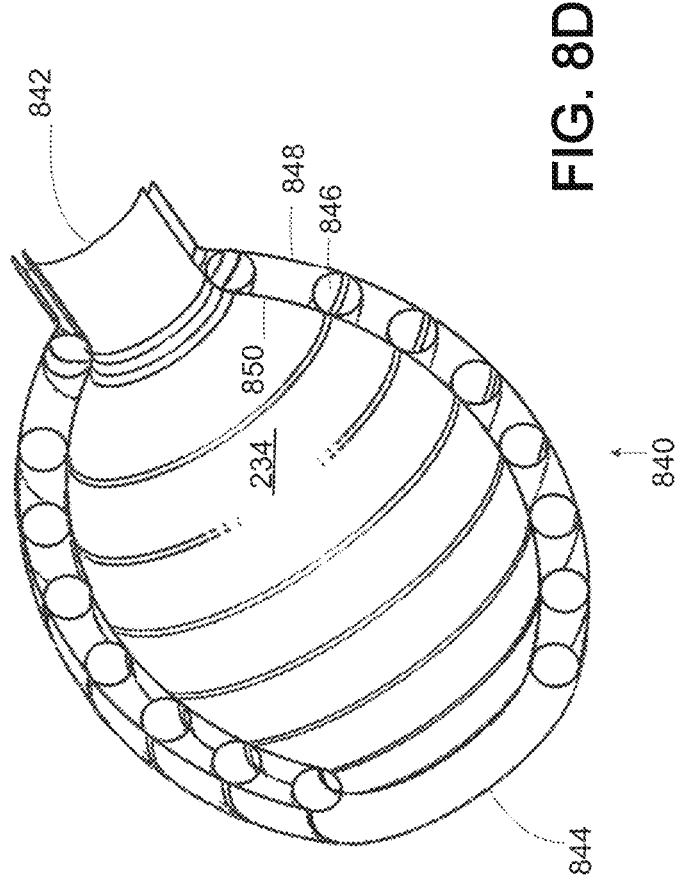

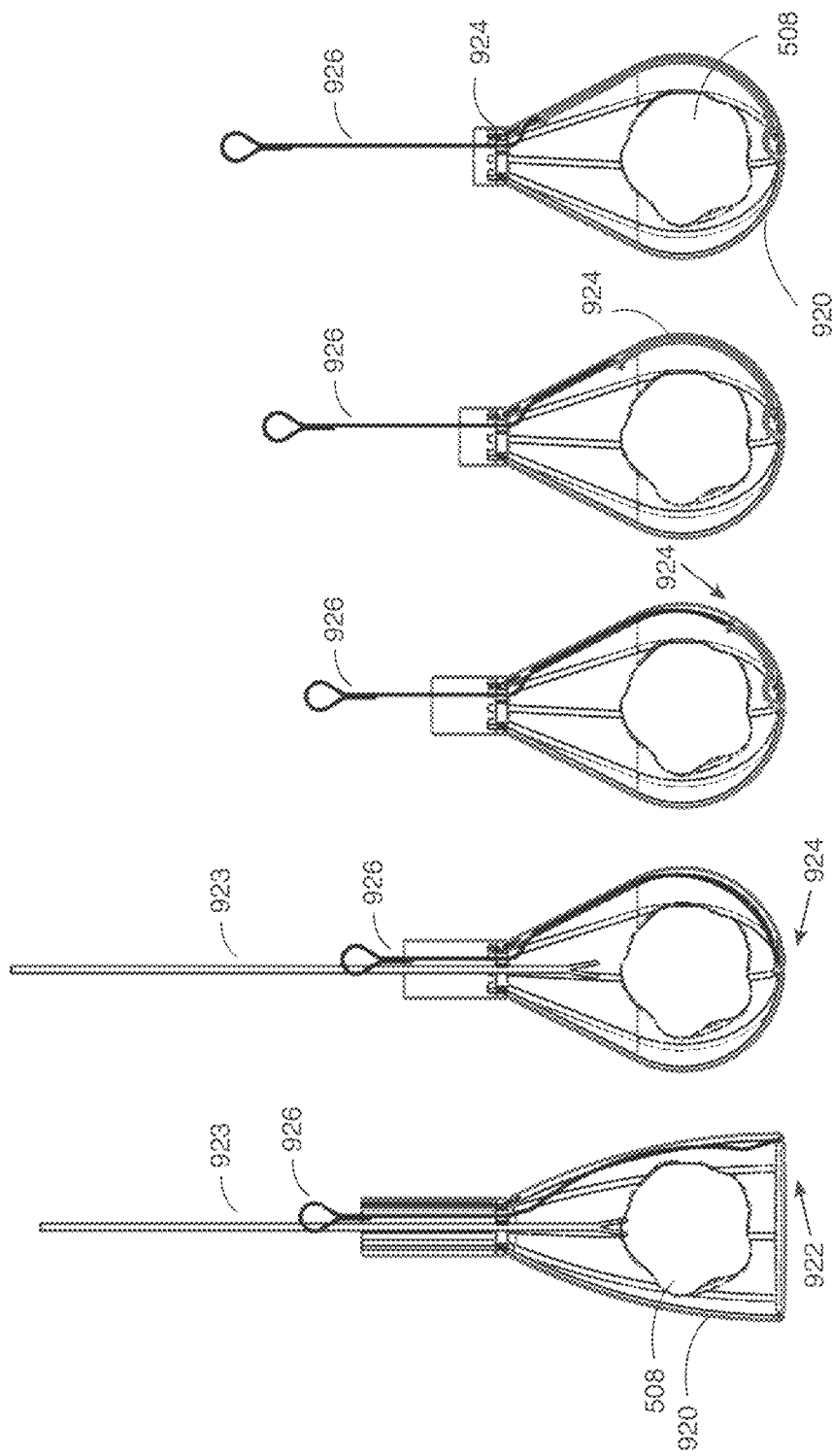

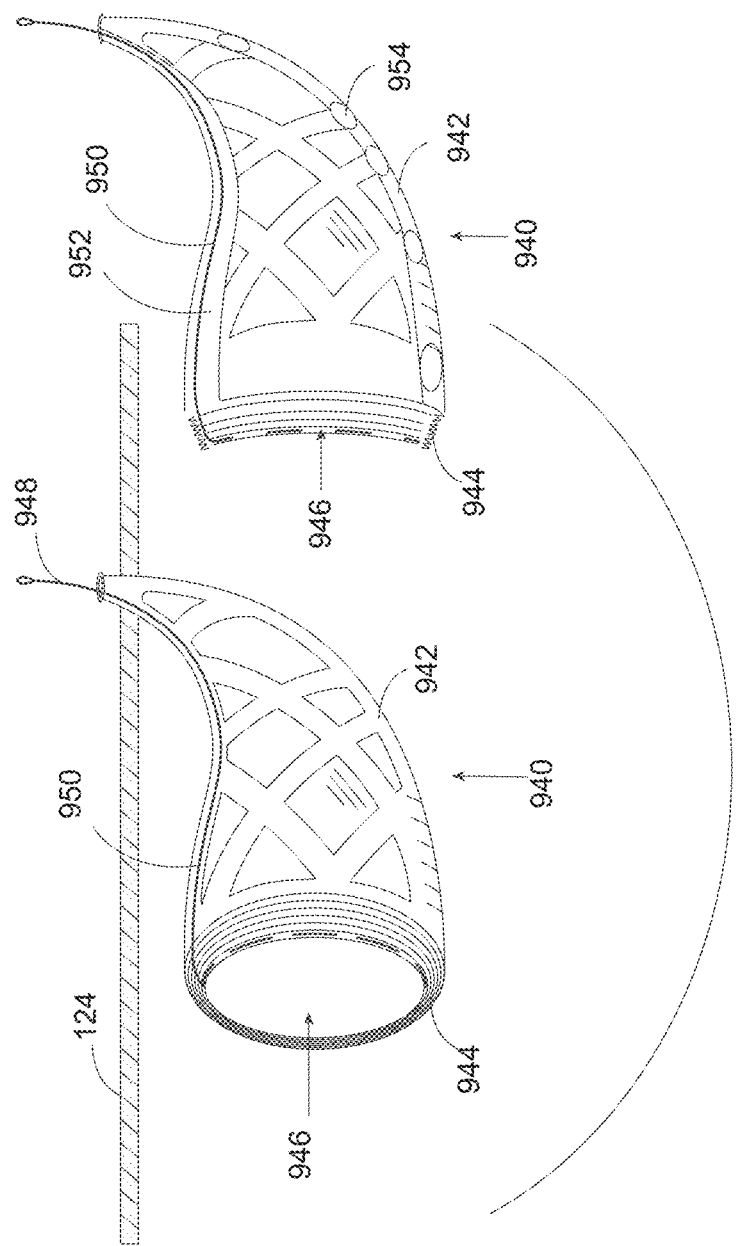

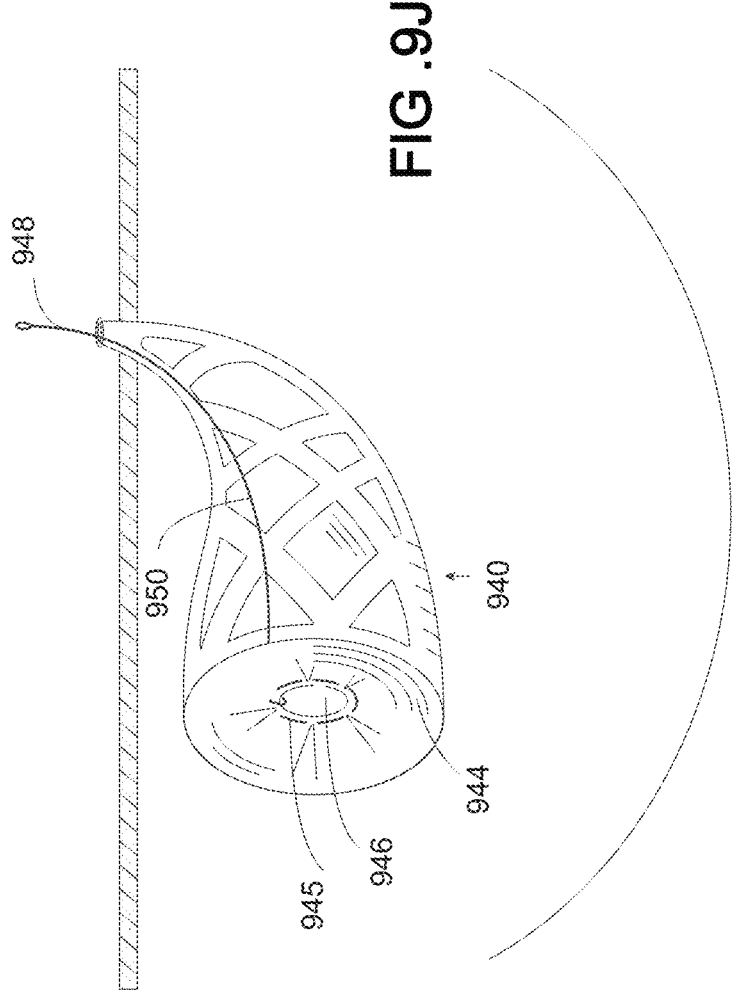

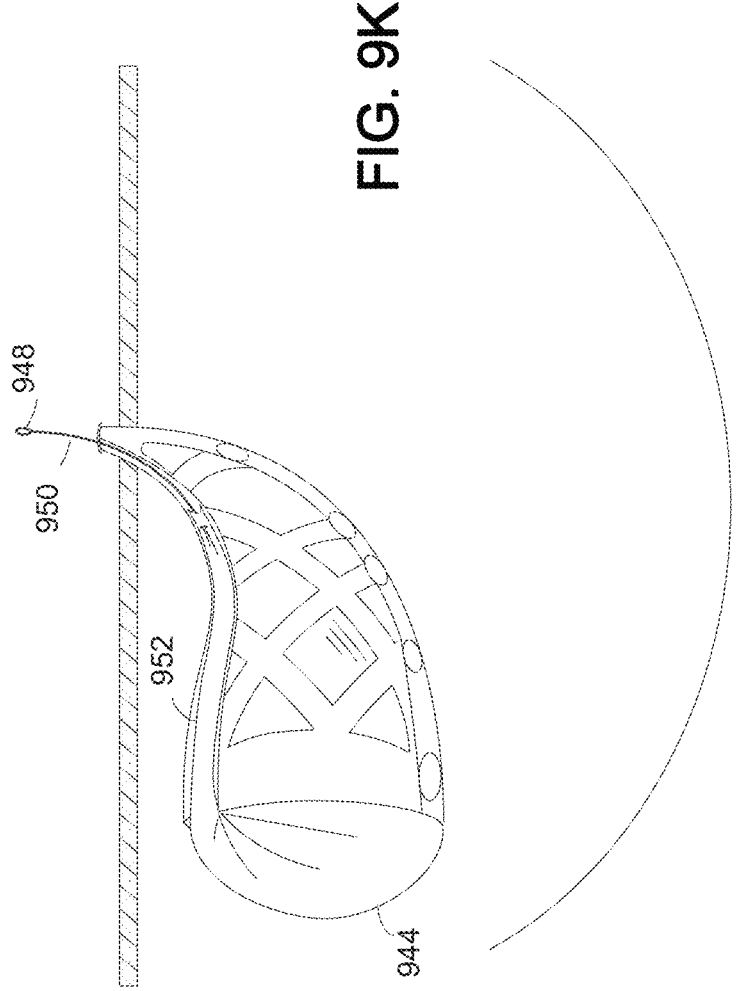

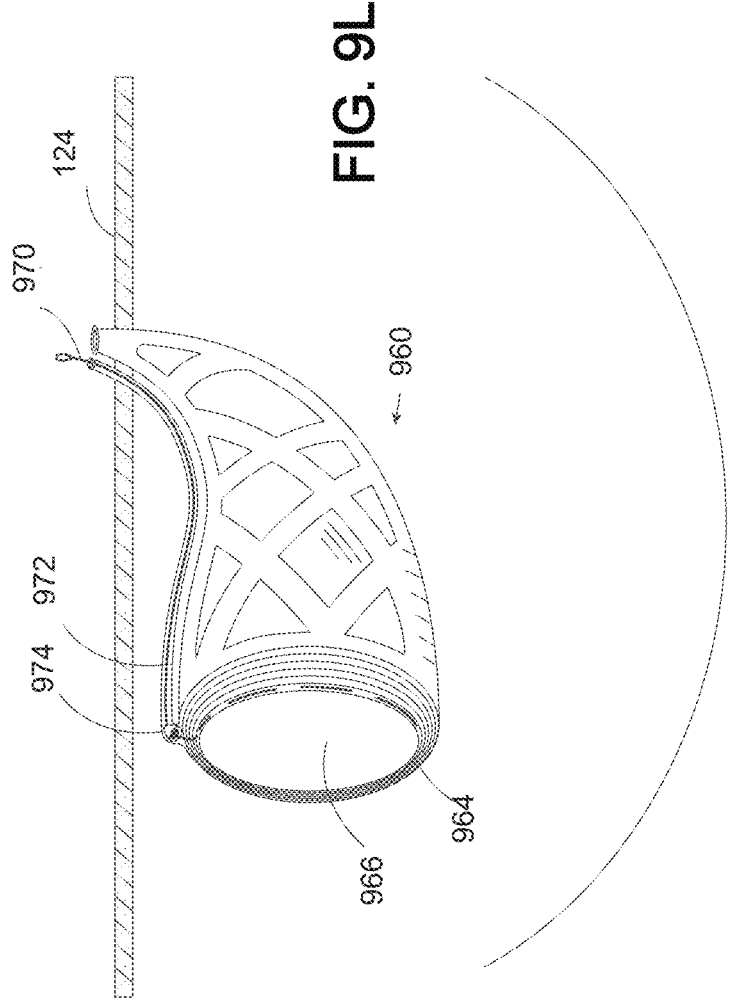

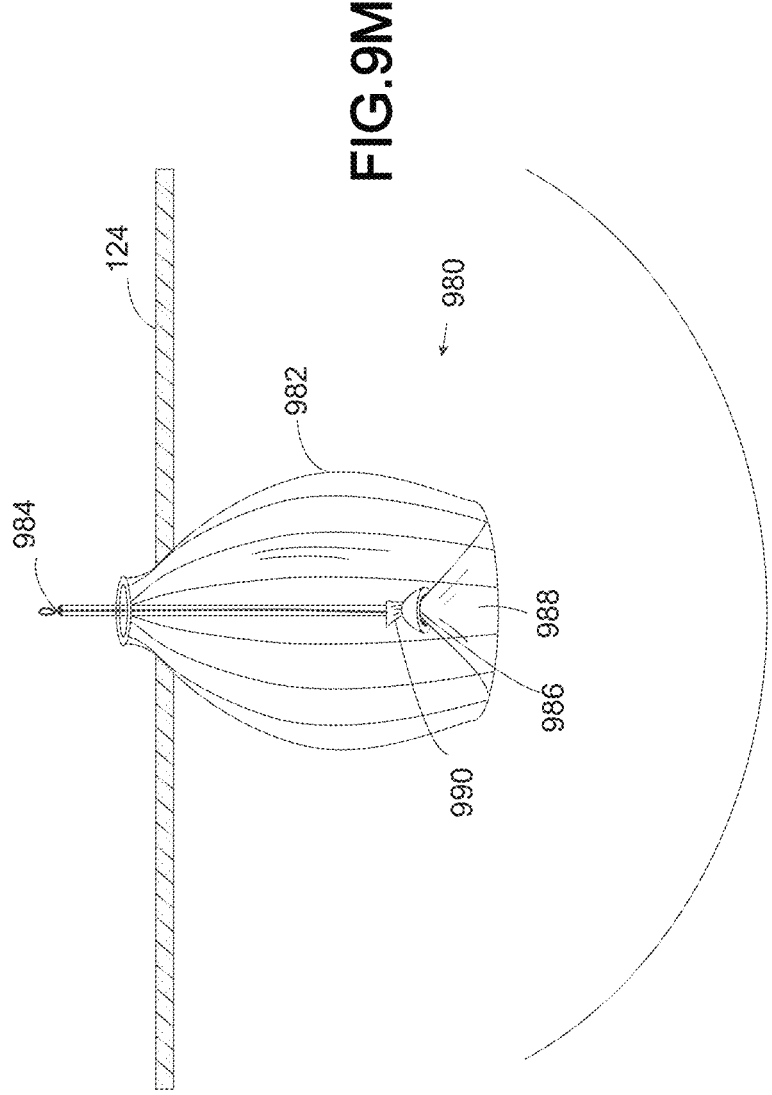

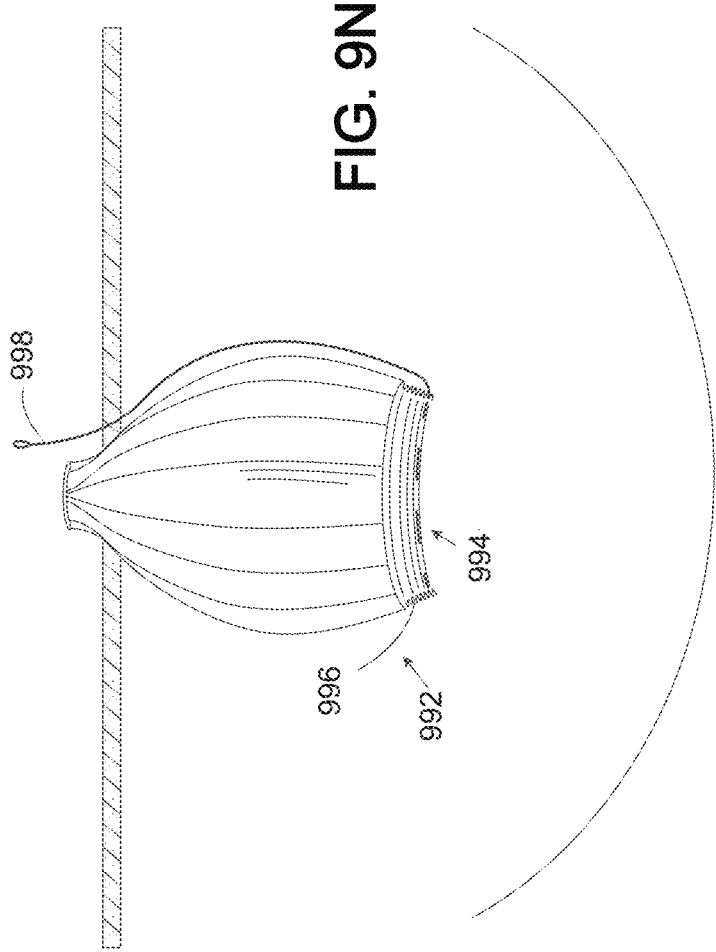

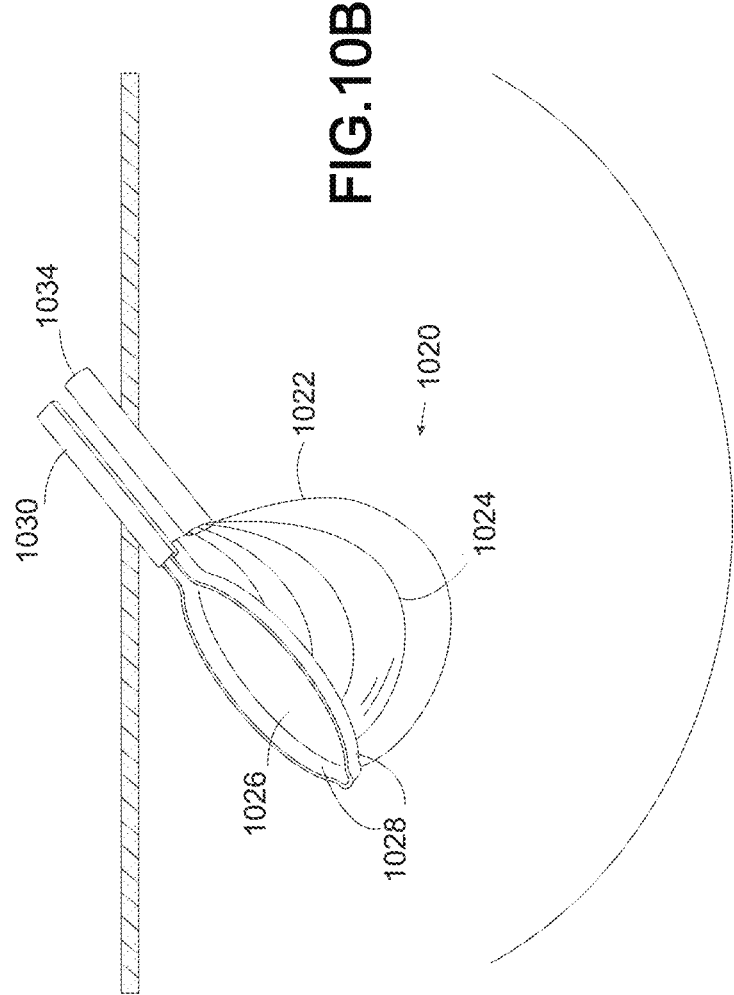

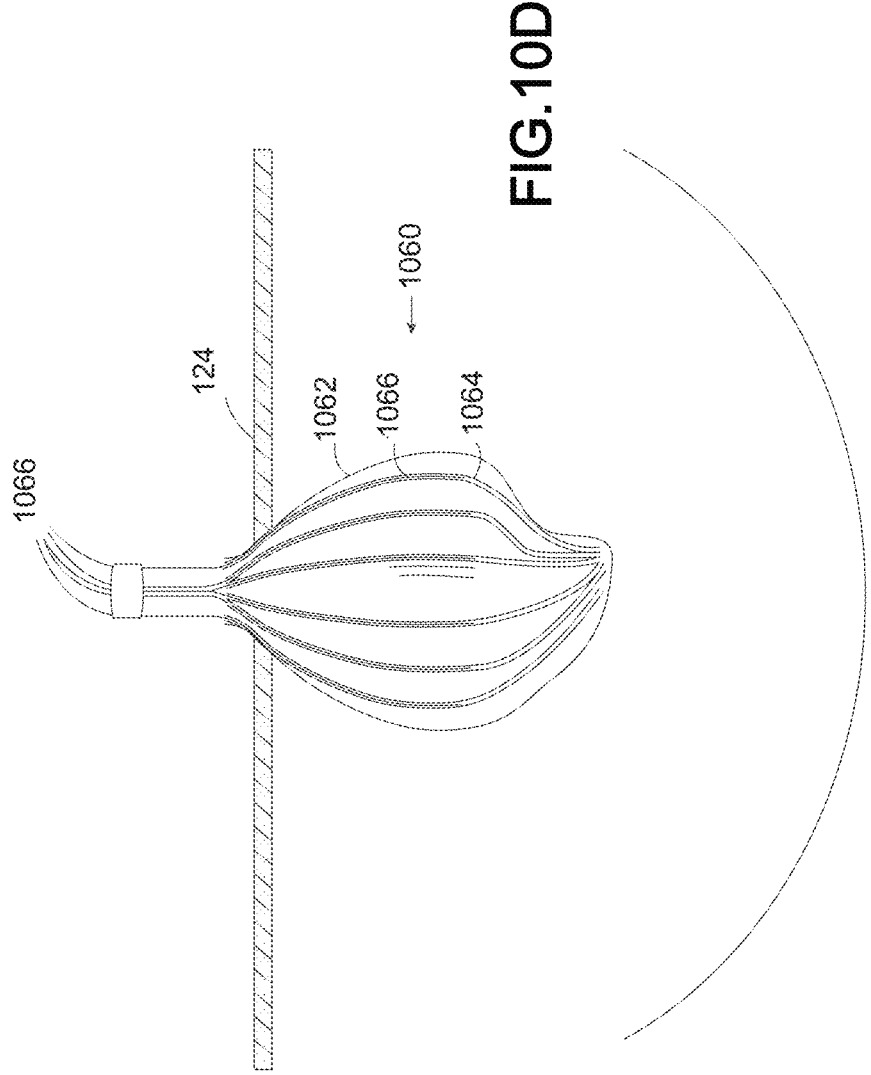

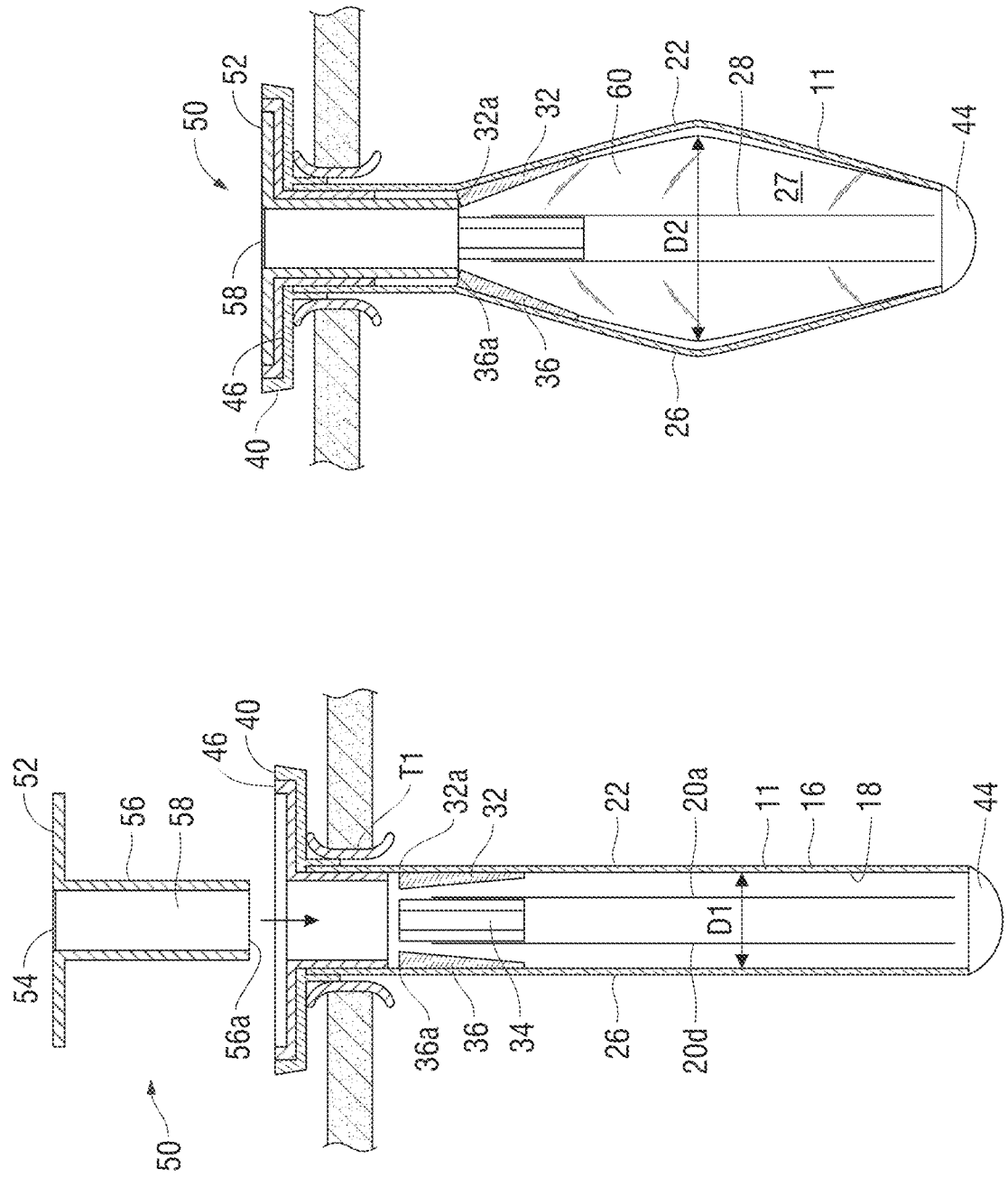

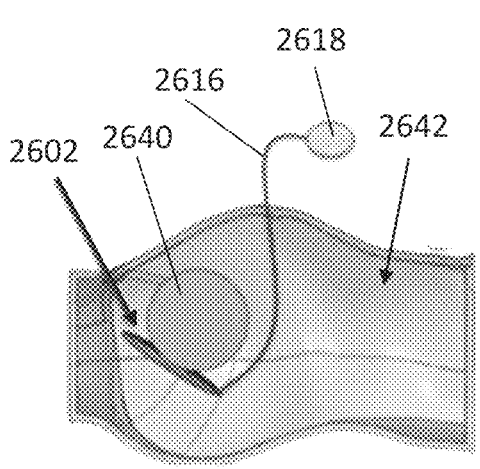
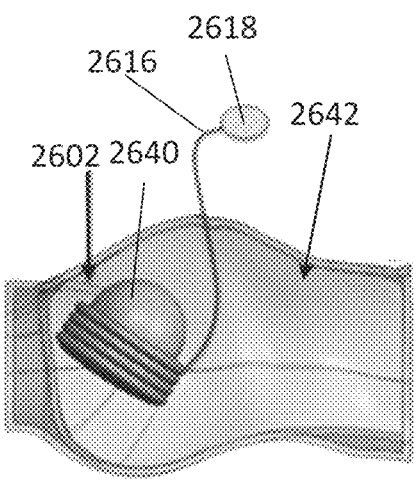
FIG. 26A    FIG. 26B
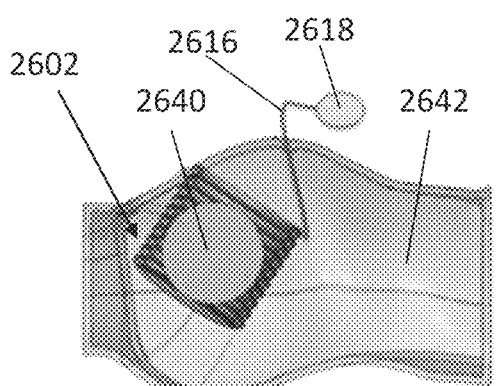
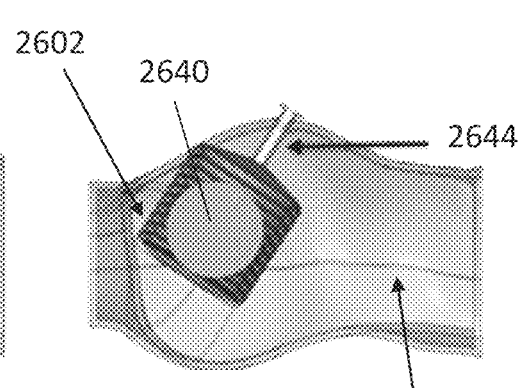
FIG. 26C    FIG. 26D
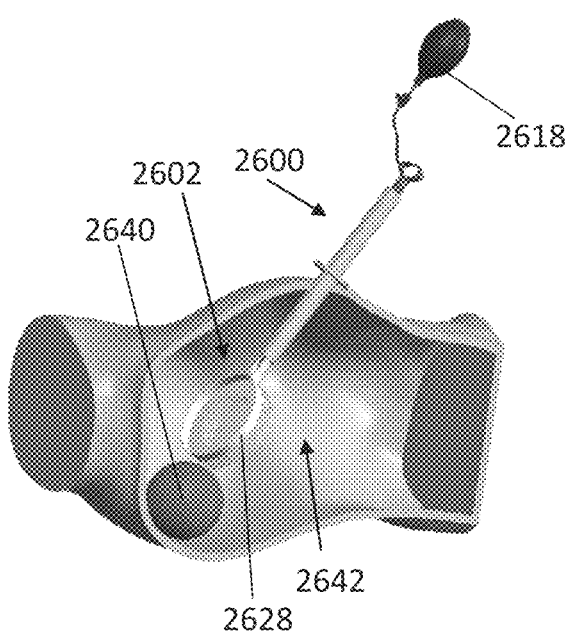
FIG. 26E

LAPAROSCOPIC WORKSPACE DEVICE

RELATED APPLICATIONS

This application is a National Phase of PCT Patent Application No. PCT/IL2018/051014 having International filing date of Sep. 6, 2018, which claims the benefit of priority under 35 USC § 119(e) of U.S. Provisional Patent Application No. 62/642,741 filed on Mar. 14, 2018.

PCT Patent Application No. PCT/IL2018/051014 is also a Continuation-in-Part (CIP) of PCT Patent Application No. PCT/IL2017/051015 having International filing date of Sep. 10, 2017, which claims the benefit of priority under 35 USC § 119(e) of U.S. Provisional Patent Application No. 62/393,015 filed on Sep. 10, 2016.

The contents of the above applications are all incorporated by reference as if fully set forth herein in their entirety.

TECHNICAL FIELD

This application relates to a device used in reduced invasiveness surgery, for example, but not exclusively, to a laparoscopic device which may be used for specimen removal.

BACKGROUND OF RELATED ART

Every year about 15-20 million laparoscopic procedures are performed worldwide. The advantages of laparoscopy (minimally invasive surgery) over laparotomy (open surgery) are well recognized and include reduced morbidity, less time in the hospital, faster recovery time and reduced costs to the patient and surgery center.

Many of the laparoscopic procedures include the removal of internal organs, such as cholecystectomies, nephrectomies, myomectomies, ovarian cystectomies etc. The removed organs can either be solid or cystic. Currently, there are several ways to remove the mass. One way is by creating an incision in the abdominal wall that allows the removal of the mass. This converts the procedure to a laparotomy or mini-laparotomy with the attendant disadvantages of open surgery. Another way is by removing the mass through the cul-de-sac, by performing an incision at the vaginal apex (culdotomy). This disadvantageously requires another incision and also has the disadvantages of increased injury and infection. A third way is by draining the cystic mass and then removing the cyst capsule through one of the laparoscopy ports. The disadvantage of this method is the risk of spillage of the cyst contents. A fourth method of removing the mass is by cutting the large solid mass to smaller particles inside the abdomen and removing the particles through one of the laparoscopy ports or through a culdotomy. Such cutting is achieved by laparoscopic cutting devices which have the disadvantages of scattering tissue in the abdominal cavity and injury to the abdominal organs by the cutting devices.

Another alternative method developed over the years involved the use of a morcellator, a dedicated device that shreds the mass inside the abdomen and allows the removal of the shredded particles through one of the laparoscopy ports. Since 1993, several types of electromechanical and manual morcellators were developed, either disposable or for multiple use. The morcellators allowed fast removal of large abdominal solid masses through a laparoscopy port by reducing the mass size so it could fit through the port. Their use offered patients the benefits of laparoscopic surgery even when large masses had to be removed from the abdominal cavity, such as procedures that involved myomectomy, hysterectomy, removal of large solid adnexal masses or nephrectomy.

For power morcellation, several specimen bags are currently being used. The bag is introduced though a laparoscopy port, the specimen is placed inside the bag, a large laparoscopy port is removed and the free edges of the bag are brought through the incision. Then the port is placed into the bag opening and insufflation is placed through this port. The scope can be placed in two ways: 1) through a port located outside the bag; or 2) through a new port that is placed from the outside into the insufflated bag and is secured by a balloon tip trocar.

US patent 521551 describes "Laparoscopy organ retrieval apparatus and procedures are presented for minimum invasion surgery inclusive of laparoscopic nephrectomy, cholecystectomy and other organ dissection, morsellation removal from the abdomen through a keyhole incision. The apparatus and procedures permit the safe and total removal of an organ from a body cavity in a morsellated condition through the combination utilization of an entrapment envelope sheath. The entrapment envelope having an apparatus for opening and closing, the apparatus controlled from an exterior position of the body cavity wherein the entrapment envelope after entry of the sheath is extruded from the sheath which has been inserted through a laparoscopic port in place in a keyhole surgical opening. The entrapment envelope is constructed of flexible, relatively low bulk fluid impermeable materials having sufficient strength to contain morsellator entry, organ fragmentation and removal."

US patent application publication 2004/0097792 describes "A method of providing access to tissue for a surgical instrument through a body wall is provided. The method includes providing an expandable retractor having a flexible sheath, the retractor being in a collapsed state; introducing the retractor into the body and placing the retractor adjacent the tissue; expanding the retractor; deploying the flexible sheath by engaging the flexible sheath with a tool and driving the flexible sheath through the body wall with the tool; and inserting the surgical instrument from outside the body through the flexible sheath to provide access to the tissue by the surgical instrument."

US patent application publication US20150297254 describes "A morcellator shield and bag assembly including a shield having a cavity and a bag coupled to the shield. The bag is moveable between a contracted position, in which at least a portion of the bag is positioned within the cavity, and an expanded position. The bag has an opening that is in fluid communication with the cavity when the bag is in the expanded position. A method for using the assembly along with a morcellator to remove tissue from a body cavity. The method includes inserting at least a portion of the assembly into a body cavity, moving the bag to the expanded position, placing tissue in the bag, pulling the bag through an opening in a patient, inserting the morcellator into the assembly, and morcellating the tissue with the morcellator. The assembly is designed to contain the tissue being morcellated and prevent the morcellator from contacting the bag."

SUMMARY OF THE INVENTION

Some exemplary embodiments of the invention are now noted as the following examples. It is noted that features from one example may be used with another example.

Example 1

A workspace device comprising:
(a) a body having a wall defining an internal volume, collapsible to fit through a laparoscopic passageway in an abdominal wall to an abdominal cavity and expand therein;
(b) a first opening defined in said body;
(c) a tool channel contiguous with said first opening and extending from said body and configured to remain, at least in part, outside of abdominal wall and sized to receive a laparoscopic tool therein; and
(d) said body defining an orifice configured to lie in said abdominal cavity when said body is inserted therein, said orifice sized to receive tissue with a minimal cross-sectional area that is twice a minimal cross-sectional area of said first opening,
thereby defining a workspace volume to process said tissue in said cavity while said body is not collapsed, using a tool inserted through said first opening.

Example 2

A device according to example 1, wherein said tool channel comprises a rigid element which maintains a shape of said first opening and restricts advance of said tool channel into said abdominal cavity.

Example 3

A device according to example 1, wherein said orifice is directed generally laterally relative to an axis of said volume extending from said opening.

Example 4

A device according to any of examples 1-3, comprising a valve configured to seal around said tool.

Example 5

A device according to any of examples 1-4, wherein said orifice is closable.

Example 6

A device according to example 5, wherein said orifice has lips configured to close against each other.

Example 7

A device according to example 5, wherein said orifice has lips configured to close against tissue.

Example 8

A device according to any of examples 5-7, wherein said orifice seals when closed.

Example 9

A device according to any of examples 5-8, wherein said orifice has lips configured to be interlocked using a zipper.

Example 10

A device according to any of examples 5-8, wherein said orifice comprises a draw string which constricts the orifice when drawn.

Example 11

A device according to any of examples 5-8, wherein said orifice comprises a draw string which pulls lips of said orifice into a narrow aperture.

Example 12

A device according to any of examples 5-8, wherein said orifice comprises an inflatable lip, which when inflated closes said orifice.

Example 13

A device according to any of examples 5-12, wherein said orifice has a normally open state.

Example 14

A device according to any of examples 5-13, wherein said orifice has a normally closed state.

Example 15

A device according to any of examples 5-10, wherein said orifice is closable by moving said orifice out of the abdominal cavity, while said body remains in said abdominal cavity.

Example 16

A device according to example 15, wherein said wall comprises a movable thin membrane and wherein said orifice is formed in said membrane and wherein said membrane is pull able towards said channel and out of said abdominal cavity, while said workspace volume remains in said abdominal cavity.

Example 17

A device according to example 15, wherein said orifice comprises a collected sleeve, and wherein said orifice is closed by said sleeve being extended and closed.

Example 18

A device according to example 17, wherein said sleeve is long enough to extend out of said laparoscopic passageway while said body and said volume remain in said abdominal cavity.

Example 19

A device according to example 18, wherein said sleeve is configured to be extended outside of said body.

Example 20

A device according to example 18, wherein said sleeve is configured to be extended through said body.

Example 21

A device according to any of example 17-20, wherein said sleeve acts as said wall when extended, to cover said orifice.

Example 22

A device according to any of examples 17-21, wherein said sleeve is collected in a pleated configuration.

Example 23

A device according to any of examples 5-22, wherein said orifice is sealable.

Example 24

A device according to example 23, wherein said orifice comprises adhesive for providing said sealing.

Example 25

A device according to example 23, wherein said orifice comprises a suction seal between lips of said orifice.

Example 26

A device according to example 23, wherein said orifice comprises a zipperable lip.

Example 27

A device according to example 23, comprising a slider which clamps the lips of said orifice.

Example 28

A device according to any of examples 1-26, comprising at least one rigidizer configured to allow said body to resist external pressure of at least 5 mmHg without collapsing, when expanded inside said abdominal cavity.

Example 29

A device according to example 28, wherein said at least one rigidizer is configured to expand said body.

Example 30

A device according to example 28 or example 29, wherein said wall comprises a thin membrane and wherein said thin membrane is attached to and stretches over said at least one rigidizer to provide an outer surface for said wall.

Example 31

A device according to any of examples 28-30, wherein said at least one rigidizer defines a frame for said wall.

Example 32

A device according to any of examples 28-30, wherein said at least one rigidizer is insertable into said cavity after insertion of said body.

Example 33

A device according to example 32, wherein said rigidizer is inserted into said wall.

Example 34

A device according to any of examples 28-30, wherein said at least one rigidizer comprises at least one inflatable compartment.

Example 35

A device according to any of examples 28-30, wherein said at least one rigidizer is permanently attached to said wall.

Example 36

A device according to any of examples 28-35, wherein said at least one rigidizer is bendable.

Example 37

A device according to any of examples 28-35, wherein said at least one rigidizer is formed of a shape memory and/or super-elastic material.

Example 38

A device according to any of examples 28-35, wherein said at least one rigidizer includes one or more pre-defined bending points.

Example 39

A device according to any of examples 1-39, comprising at least one damage resistant section defined opposite said first opening and more resistant to damage from said tool than other parts of said wall.

Example 40

A device according to any of examples 1-40, comprising at least one sensor configured to indicate if said wall is damaged.

Example 41

A device according to any of examples 1-40, wherein said tool channel comprises a designated laparoscopic port.

Example 42

A device according to any of examples 1-41, comprising a port positioned for insertion of a tool to a side of said body.

Example 43

A device according to any of examples 1-42, wherein body has a general ellipsoid shape when expanded.

Example 44

A device according to any of examples 1-42, wherein body has an asymmetric curvature such that said body is directed down and then laterally and wherein said orifice is defined at an end of said body.

Example 45

A device according to any of examples 1-44, wherein workspace volume is large enough to receive an adult human kidney and small enough and rigid enough to not contact intra-abdominal organs when suspended from said laparoscopic channel into an abdominal cavity and containing said kidney.

Example 46

A device according to any of examples 1-45, comprising at least one suction channel extending from within said workspace volume to outside of said abdominal cavity.

Example 47

A workspace device comprising:
(a) a body having a wall defining an internal volume, collapsible to a collapsed state where said body fits through a laparoscopic passageway in an abdominal wall to an abdominal cavity and expandable to an expanded state within said cavity;
(b) said wall including at least one rigidizer, which, in said expanded state, causes said body to resist collapse by intra-abdominal forces; and
(c) said body defining an orifice configured to lie in said abdominal cavity when said body is in said expanded state in said cavity, said orifice sized to receive tissue, thereby defining a workspace volume to process said tissue in said cavity without process tissue leaking into said abdominal cavity, while said body is in said expanded state.

Example 48

A device according to example 47, wherein said at least one rigidizer is inflatable.

Example 49

A device according to example 48, wherein said at least one rigidizer comprises a plurality of separately inflatable compartments.

Example 50

A device according to example 47, wherein said wall defines at least one pocket for removably inserting said at least one rigidizer therein.

Example 51

A device according to any of examples 47-50, wherein said device, in said expanded state can withstand collapse under a condition where a pressure in said intra-abdominal cavity on one said of said wall is at least 10 mmHg greater than a pressure inside said workspace volume.

Example 52

A device according to any of examples 47-51, wherein said wall comprises a thin membrane stretched between said at least one rigidizer.

Example 53

A device according to example 52, wherein said at least one membrane is elastic.

Example 54

A device according to example 52 or example 53, wherein said at least one membrane mechanically interacts with said at least one rigidizer to set a geometry of said volume.

Example 55

A device according to any of examples 52-54, comprising at least one pusher which selectively applies a distally directed force on said at least one rigidizer to set a geometry of said volume.

Example 56

A device according to any of examples 47-55, comprising at least one adjustable elongate tensile member which mechanically interacts with said at least one rigidizer to set a geometry of said volume.

Example 57

A device according to example 56, wherein said tensile member comprises a wire located within at least one of said at least one rigidizer.

Example 58

A device according to any of examples 47-56, wherein said body defines an orifice closable to withstand intra-abdominal pressure.

Example 59

A workspace device comprising:
(a) a body having a wall defining an internal volume, collapsible to a collapsed state where said body fits through a laparoscopic passageway in an abdominal wall to an abdominal cavity and expandable to an expanded state within said cavity;
(c) said body configured to receive and enclose tissue from said abdominal cavity, of a volume of at least 300 cc;
(d) said body sealed or sealable and rigid enough to prevent collapse when an intra abdominal pressure is at least 10 mmHg higher than a pressure in said volume, when said body is in said expanded state.

Example 60

A workspace device comprising:
(a) a body having a wall defining an internal volume, collapsible to a collapsed state where said body fits through a laparoscopic passageway in an abdominal wall to an abdominal cavity and expandable to an expanded state within said cavity;
(b) said wall including at least one rigidizer, which, in said expanded state, causes said body to resist collapse by intra-abdominal forces;
(c) said body defining an orifice configured to lie in said abdominal cavity when said body is in said expanded state in said cavity, said orifice sized to receive tissue; and (d) a collected membrane coupled to said orifice and configured to be extended to close said orifice.

Example 61

A device according to example 60, wherein said membrane is collected around said orifice.

Example 62

A device according to example 60, wherein said orifice is at an end of said body and wherein said collected membrane forms an extension to said device.

Example 63

A device according to example 60, wherein said membrane is collected to a side of said orifice.

Example 64

A device according to example 60, wherein said membrane is collected around a circumference of said device and wherein said orifice is formed in a movable part of said membrane.

Example 65

A device according to any of examples 60-64, wherein said collected membrane is long enough to extend past a proximal end of said body, when said body is in said expanded state.

Example 66

A device according to any of examples 60-65, comprising a puller coupled to said membrane and extending to outside of said body.

Example 67

A device according to example 66, wherein said puller is coupled circumferentially to said collected membrane and thereby operative to reduce a diameter of said orifice when pulled.

Example 68

A device according to example 66 or example 67, comprising a channel for passage of said puller therethrough.

Example 69

A device according to any of examples 66-68, wherein said collected membrane includes a restrictor which prevent uncollection thereof.

Example 70

A device according to example 69, wherein said restrictor comprises adhesive or a weld.

Example 71

A device according to any of examples 60-70, comprising a channel for passage of said collected membrane therethrough to outside of said body.

Example 72

A device according to any of examples 60-70, comprising a restricted diameter restrainer for passage of said collected membrane therethrough.

Example 73

A workspace device comprising:
(a) a body having a wall defining an internal volume, collapsible to a collapsed state where said body fits through a laparoscopic passageway in an abdominal wall to an abdominal cavity and expandable to an expanded state within said cavity, said volume being at least 300 cc.;
(b) at least one sensor within or on said body and configured to generate a signal indicating damage or risk of damage to said wall.

Example 74

A device according to example 73, wherein said sensor comprises a mechanical sensor.

Example 75

A device according to example 73, wherein said sensor comprises an electrical sensor.

Example 76

A device according to any of examples 73-75, wherein said wall is hollow and wherein said sensor senses a change in pressure in said wall.

Example 77

A method of processing tissue in a laparoscopic manner, comprising:
(a) inserting a collapsed workspace device in to an abdominal cavity;
(b) expanding the device to define a workspace volume therein;
(c) bringing tissue from said cavity into said device;
(d) isolating said tissue from said cavity;
(e) processing said tissue,
wherein said cavity has a same or lower pressure than said workspace volume during said processing.

Example 78

A method according to example 77, wherein said bringing is via one opening and said processing is via another opening.

Example 79

A method according to example 77, wherein said abdominal cavity is insufflated during said insertion and is not deflated until said processing is completed.

Example 80

A method according to example 77, wherein said bringing comprises bringing through an orifice and wherein said isolating comprises closing said orifice.

Example 81

A method according to example 77, wherein said isolating does not require movement of said tissue.

Example 82

A method according to example 77, wherein said isolating comprises pulling on a puller to move a part of said device relative to another part of said device.

Example 83

A method according to example 77, wherein said processing is via an opening in said device which remains outside of the body during said (a)-(e).

Example 84

A method according to example 77, wherein said processing comprises processing without said device contacting intra-abdominal organs or tissue other than an abdominal wall.

Example 85

A method according to example 77, wherein said expanding comprises inflating one or more chambers in said device.

Example 86

A method according to example 77, wherein said expanding comprises inserting a rigidizer into said device.

In accordance with one aspect of some embodiments of the present invention, a minimally invasive specimen retrieval device is provided comprising a first member movable from a first collapsed position to a second expanded position, a plurality of rigidifying members positioned internal of the first member, and an engagement member insertable into the first member, the engagement member moving the plurality of rigidifying members radially outwardly to move the first member from the first collapsed position to the second expanded position.

In some embodiments, the first member is a tubular member having a longitudinal axis and a plurality of longitudinally extending slits. The tubular member can have an opening at a proximal end and can be closed at a distal end.

In some embodiments, the first member comprises a plurality of leaves separated by slits and a cover extends over the leaves. An opening can be formed between two of the leaves for receipt of a specimen into a space within the first member. In some embodiments, the opening is selectively closable and includes for example a zip-lock mechanism or a flexible member movable proximally.

In some embodiments, the first member is substantially football shaped in the second expanded position.

In some embodiments, the engagement member is a separate element insertable into the first member; in other embodiments the engagement member is non-removably attached to the first member. In some embodiments, the engagement member is threadingly attached to the first member, wherein rotation of the engagement member advances the engagement member distally to exert a force on the rigidifying members.

In accordance with another aspect of the present invention, a minimally invasive specimen retrieval device is provided comprising a first member movable from a first collapsed position to a second expanded position and including first and second portions separable in the second expanded position. A first internal member is attached to the first portion and a second internal member is attached to the second portion. A second member is movable distally with respect to the first member to exert a force on the first and second internal members to move the first member to the second expanded position.

In some embodiments, the first member is formed of a first material and the internal member is formed of a second material, the second material being more rigid than the first material. In some embodiments, the first member includes a transparent covering material spanning a space between the first and second portions. In some embodiments, the first member includes a third portion separable from the first and second portions, and further includes an opening between the second and third portions for receipt of a specimen in a space within the first member.

In accordance with another aspect of the present invention, a minimally invasive specimen retrieval device is provided comprising a tubular member having a plurality of longitudinal slits formed therein to form a plurality of spreadable leaves. The tubular member includes a base dimensioned to remain outside an opening in a body of a patient and has an opening at a proximal end. A plurality of projections extend inwardly toward a longitudinal axis of the tubular member and a second member is advanceable within the first member to apply a force to the projections to move the leaves to a spread position to create a box-like structure.

In some embodiments, the second member is advanceable distally into the first member by a screw thread. In some embodiments, the box-like structure is shaped like a football. In some embodiments, a gap between the spread leaves is covered by a transparent material, and a receiving opening can be provided between two of the plurality of spread leaves for access to an interior of the tubular member for receipt of a specimen therein.

In accordance with another aspect of the present invention, a minimally invasive specimen retrieval device is provided comprising a tubular member having a proximal portion, a distal portion, an intermediate portion and a plurality of hinges formed at the intermediate portion. The tubular member is normally positioned in an expanded position forming a box-like structure and is insertable through a trocar in a collapsed position and upon advancement through the trocar into a body cavity moves to the expanded position.

In some embodiments, the hinges are formed by spring biasing the tubular member to the expanded position. In some embodiments, the box-like structure is football shaped in configuration. In some embodiments, the tubular member has hinges at the proximal and distal portions.

In accordance with another aspect of the present invention, a method of retrieving a specimen from a body space in a minimally invasive procedure is provided comprising the steps of 1) providing a device having a plurality of separable portions and a plurality of internal projections; 2) inserting the device through an opening in a patient into the body space; 3) expanding the device to an expanded position, the device maintained by the projections in the expanded position; 4) placing a specimen in the device; and 5) closing the device to encapsulate the specimen.

In some embodiments, the method further comprises the step of morcellating the specimen within the device. Preferably, the projections keep the walls of the device away from the specimen placed within the device.

In some embodiments, the step of inserting the device introduces the device through a trocar through an abdominal wall of the patient. In other embodiments, the step of inserting the device introduces the device through a vaginal cuff.

In some embodiments, the inside of the device is viewable via direct visualization from outside the device. In some embodiments, the step of placing the specimen in the device comprises the step of placing a specimen through a side opening in the device. The device can include a marker for facilitating directing the side opening upwards during the procedure.

In some embodiments, the step of expanding the device includes the step of advancing a member inside the device to apply an outward force to the projections. In some embodiments, the member is advanced by sliding the member distally; in other embodiments the member is advanced by rotating the member to advance the member distally.

In some embodiments, the step of closing the device includes sliding a lock mechanism. In some embodiments, the member has a valve and a morcellator is insertable through the valve and through the member into the device.

Additional exemplary embodiments of the invention are now noted as the additional following examples. It is noted that features from one example may be used with another example.

Example 1

A workspace device comprising:
(a) a workspace body having a workspace inner wall defining an internal volume, including one or more expandable segments, said workspace body formed of a flexible material such that it is:
  collapsible to a collapsed state where said body fits through a laparoscopic passageway in an abdominal wall, which passageway extends to an abdominal cavity; and
  expandable, to increase said internal volume, to an expanded state within said cavity, by inflation of said one or more expandable segments, where, in said expanded state said workspace body:
   has an opening to said internal volume;
   and extends axially from a proximal to a distal direction defining a workspace axis;
(b) one or more channels sized and shaped to supply inflation fluid to said workspace body;
(c) said workspace body including:
  a plurality of circumferentially extending inflatable segments at a plurality of axial positions on said workspace body;
  a fluid pathway connecting at least one of said one or more channels to at least one of said segments;
  where each of said segments is fluidly connectable to at least one of said one or more channels;
 where inflation through said one or more channels expands said segments according to a predetermined order to said expanded state, where, in said expanded state, said segments rigidize said workspace body to resist collapse by intra-abdominal forces.

Example 2

The workspace device according to example 1 wherein a fluid pathway from a channel of said one or more channels to a plurality of segments, a first segment before one or more other segments in the pathway, defines said predetermined order.

Example 3

The workspace device according to example 2, wherein said first segment inflates by at least 50% before said one or more other segments in said pathway.

Example 4

The workspace device according to any one of examples 1-3, wherein one or more restrained segment is restrained from inflating, by one or more of:
 adhesion to one or more portion of the workspace device;
 friction;
 a valve in a fluid pathway for inflation of said one or more restrained segment.

Example 5

The workspace device according to example 4, wherein said valve opens under applied inflation pressure.

Example 6

The workspace device according to example 5, wherein a portion of said valve ruptures to open.

Example 7

The workspace device according to any one of examples 1-6, wherein an inflated segment presses on adjacent segments to expand said workspace device.

Example 8

The workspace device according to any one of examples 1-7, wherein at least one segment is fluidly connected one or more adjacent segment.

Example 9

The workspace device according to example 8, wherein each segment is fluidly connected to axially adjacent segments.

Example 10

The workspace device according to any one of examples 1-9, wherein said segments press against each other to expand said workspace device.

Example 11

The workspace device according to any one of examples 1-10, wherein said segments inflate sequentially according to said predefined order.

Example 12

The workspace device according to any one of examples 1-11, wherein said workspace device includes at least one elastic element, where said elastic element is elastically compressed in said collapsed configuration and relaxed in said expanded configuration.

Example 13

The workspace device according to any one of examples 1-12, wherein said workspace device has a deployed configuration, where said body is expanded from said collapsed configuration in one direction.

Example 14

The workspace device according to example 13, wherein an elastic element elastically relaxes to transfer said workspace device from said collapsed configuration to said deployed configuration.

Example 15

The workspace device according to example 14, wherein said elastic element is a rim connected to said opening.

Example 16

The workspace device according to example 15, wherein said rim is attached to an elongate handle sized and shaped to extend through said laparoscopic passageway outside of said cavity.

Example 17

The workspace device according to example 16, wherein said handle and said workspace device in said collapsed configuration is sized and shaped to contained by a lumen of a deployment device, where said deployment device is sized and shaped to extend from outside said cavity, through said laparoscopic passageway and into said cavity.

Example 18

The workspace device according to any one of examples 1-17, where, when said workspace device expands from said collapsed configuration in a direction along said axis and in a direction perpendicular to said axis to said expanded configuration.

Example 19

The workspace device according to any one of examples 1-18, comprising a flexible portion connected to said body.

Example 20

The workspace device according to example 19, wherein said flexible portion is connected to said body between said opening and body.

Example 21

The workspace device according to example 20, wherein said flexible portion is tubular.

Example 22

The workspace device according to example 21, wherein portion is sized and shaped to collapse to fit inside said laparoscopic opening with a morcellator device.

Example 23

The workspace device according to any one of examples 1-22, wherein one said workspace body includes at least a portion which is tubular in shape.

Example 24

The workspace device according to any one of examples 1-23, wherein said workspace wall includes at least a portion which is tubular in shape.

Example 25

The workspace device according to any one of examples 1-24, wherein said plurality of circumferentially extending segments are contiguous.

Example 26

The workspace device according to example 25, wherein said plurality of circumferentially extending segments form a single inflatable chamber.

Example 27

The workspace device according to example 26, wherein said single inflatable chamber has a helical shape.

Example 28

The workspace device according to any one of examples 1-27, wherein one or more of said segments has a reduced axial dimension portion, forming a window between axially adjacent segments.

Example 29

The workspace device according to any one of examples 1-28, wherein one or more of said segments have a ring shaped lumen.

Example 30

The workspace device according to example 29, wherein one or more of said segments contacts axially adjacent segments.

Example 31

The workspace device according to any one of examples 29-30, wherein one or more of said segments is connected to one or more adjacent segment by an uninflated ring of material.

Example 32

The workspace device according to any one of examples 29-31, wherein:
  one or more of said segments is toroidal in shape with a circular cross section;
  one or more of said segments has an elliptical cross section;
  one or more of said segments has a semicircular cross section;
  one or more of said segments has cross section which changing dimensions.

Example 33

The workspace device according to any one of examples 1-32, wherein one or more of said segments has a circular cross section with a varying diameter.

Example 34

The workspace device according to any one of examples 1-33, comprising a reinforced base portion connected to a distal end of said body.

Example 35

The workspace device according to any one of examples 1-34, wherein said body is constructed from two tubular sheets of material connected at portions to form said segments.

Example 36

The workspace device according to example 35, wherein one of both of said tubular sheets are shaped with a non-planar shape when relaxed.

Example 37

The workspace device according to any one of examples 1-36, wherein said body is constructed by adhering segments to each other.

Example 38

The workspace device according to example 37, wherein one or more of said segments are formed by two adhered sheets of material.

Example 39

The workspace device according to any one of examples 1-38, comprising a sieve connected to said body within said workspace, said sieve separating said workspace into two portions.

Example 40

The workspace a device according to any one of examples 1-39, comprising an outer bag sized and shaped to surround said workspace device in an expanded configuration.

Example 41

A method of processing tissue in a laparoscopic manner, comprising:
 inserting a collapsed workspace device in to an abdominal cavity;
 expanding the device to define a workspace volume therein by inflating segments of said device sequentially in a predefined order;
 bringing tissue from said cavity into said device through an opening of said workspace device;
 isolating said tissue from said cavity.

Example 42

The method according to example 41, comprising increasing a pressure within said workspace volume to a pressure above a pressure within said cavity.

Example 43

The method according to any one of examples 41-42, wherein said expanding is performed before said bringing.

Example 44

The method according to any one of examples 41-42, wherein said bringing is performed before said expanding.

Example 45

The method according to any one of examples 41-42, wherein said expanding and said bringing occur simultaneously or alternatively.

Example 46

The method according to any one of examples 41-45, comprising processing said tissue.

Example 47

The method according to any one of examples 41-46, comprising collapsing and removing said workspace device from said abdominal cavity.

Example 48

The method according to any one of examples 41-47, wherein said isolating comprises extracting said opening of said workspace device to outside said abdominal cavity.

Example 49

The method according to any one of examples 41-48, wherein said segments are circumferentially extending segments.

Example 50

The method according to any one of examples 41-49, wherein said expanding comprises expanding an opening of said workspace device.

Example 51

The method according to any one of examples 41-50 wherein said expanding comprising elastically relaxing a portion of said workspace device.

Example 52

The method according to example 51, wherein said portion is an opening of said workspace device.

Example 53

The method according to any one of examples 41-52, wherein said expanding comprises inflating a first segment by at least 50% and then inflating segments axially adjacent said first segment.

Example 54

The method according to any one of examples 41-53, wherein expanding comprises inflating segment distal of an opening of said device and sequentially inflating increasingly proximal segments.

Example 55

The method according to any one of examples 41-53, wherein expanding comprises inflating segment proximal to an opening of said device and sequentially inflating increasingly distal segments.

Example 56

The method according to any one of examples 41-55, wherein said inserting comprises inserting a deployment device including a deployment device lumen through an incision in an abdominal wall and inserting said workspace device through said deployment device lumen.

Example 57

The method according to example 56, wherein said lumen contains said workspace in a collapsed configuration.

Example 58

The method according to any one of examples 56-57, wherein said inserting comprises pushing said collapsed workspace device through said deployment device lumen into said cavity using a handle.

Example 59

The method according to any one of examples 41-58, wherein said inflating comprises selecting an order for inflation.

Example 60

The method according to any one of examples 47-59, wherein collapsing is performed before said removing.

Example 61

The method according to any one of examples 47-60, wherein said collapsing and said removing occur at the same time.

Example 62

The method according to example 61, wherein removing collapses said workspace device by one or more of deflating said workspace device and elastically compressing one or more portion of said device.

Example 63

The method according to examples 41-62, wherein inflating is by a fluid comprising one or more of gas and liquid.

Example 64

The method according to example 63, wherein said gas comprises one or more of air and carbon dioxide.

Example 65

The method according to example 64, wherein said liquid is water or saline.

Example 66

The method according to any one of examples 41-55, where said bringing comprises dethatching said tissue from surrounding tissue.

Example 67

The method according to any one of examples 41-66, wherein said tissue includes an abdominal organ.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 is a schematic showing of the effect of negative pressure difference, on leakage, in accordance with some exemplary embodiments of the invention;

FIGS. 8C and 8D are schematic showings of inflation based workspace devices, in accordance with some exemplary embodiments of the invention;

FIGS. 9B-9F are a series showing a workspace device with an internal sleeve extendible out of the body, at various stages of use, in accordance with some exemplary embodiments of the invention;

FIGS. 9H and 9I are views of a curved workspace device with a lateral orifice having extendible lips, in accordance with some exemplary embodiments of the invention;

FIG. 9J shows a curved workspace device with a purse-string mechanism for orifice closure, in accordance with some exemplary embodiments of the invention;

FIG. 9K shows a curved workspace device with an extended lip of an orifice passed through a closure channel within the device, in accordance with some exemplary embodiments of the invention;

FIG. 9L shows a curved workspace device with an extended lip of an orifice configured for passing through a closure channel on an outside of the device, in accordance with some exemplary embodiments of the invention;

FIG. 9M shows a workspace device with an extended lip of an orifice configured for passing through a restrictor, for closure of the orifice, in accordance with some exemplary embodiments of the invention;

FIG. 9N shows a workspace device with an extended lip of an orifice configured for being pulled outside the device and out of the body, for closure of the orifice, in accordance with some exemplary embodiments of the invention;

FIG. 10B shows a workspace device with a sliding closure, in accordance with some exemplary embodiments of the invention;

FIG. 10D is a side view of a workspace device using tensile members within rigidifying members for controlling a shape of the device, in accordance with some exemplary embodiments of the invention;

FIG. 12A is a cross-sectional view of the device of FIG. 11 shown in the collapsed configuration, and shown inserted through a trocar into the body cavity;

FIG. 12B is a cross-sectional view of the device of FIG. 11 shown in the expanded configuration;

FIGS. 26A-D are simplified schematics of use of a workspace device within a patient cavity, according to some embodiments of the invention;

FIG. 26E is a simplified schematic of a workspace device within a cavity, according to some embodiments of the invention;

DESCRIPTION OF SPECIFIC EMBODIMENTS OF THE INVENTION

Overview

Figure 1A:
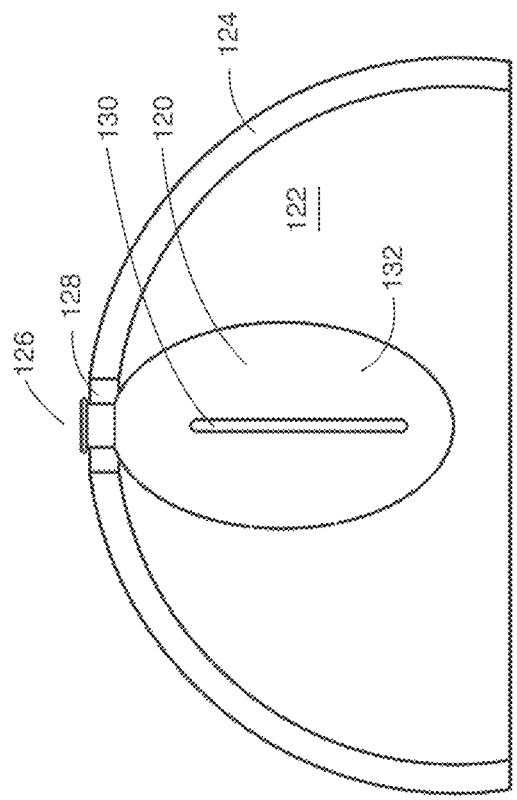
FIGS. 1A and 1B are side views of a workspace device in an open orifice state and a closed orifice state, in an abdominal cavity, in accordance with some exemplary embodiments of the invention.

A broad aspect of some embodiments of the invention relates to a workspace device, which may be inserted into the body (e.g., a body lumen such as the abdominal cavity) and used for processing body tissue therein, while inside the body. Optionally, the processing comprises morcellating or other size reduction method applied to tissue, prior to tissue removal from the body, such that the workspace device ultimately acts as a retrieval device.

In some embodiments, morcellating includes separating a small portion or "morsel" of tissue from a mass of tissue, the small portion being sufficiently small in size to be laparoscopically removed.

An aspect of some embodiments of the invention relates to a workspace device including at least one rigid or rigidifiable portion. In some exemplary embodiments of the invention, the portion is used to define the workspace inside the body. In some exemplary embodiments of the invention, the use of rigid portions allows the workspace to resist collapse due to pressure from organs or fluid (such as intra-abdominal gas used for insufflation) inside the body.

In some exemplary embodiments of the invention, the device is made more rigid and/or changes in shape to a more volumetric form when in the body and is maintained in such larger volumetric form during sealing thereof and/or processing of tissue therein.

In some exemplary embodiments of the invention, sealing comprises closing in a way which avoids pressure loss. Optionally or alternatively, sealing comprises closing in a way which avoids tissue cross-contamination.

In some exemplary embodiments of the invention, the device is defined by a wall with a plurality of rigid elements defining the wall. Optionally, flexible material is provided between the rigid elements. It should be appreciated that "rigid" does not mean hard. Rather, it means stiff enough to resist typical pressures and forces expected during an operation, for example, the device may be stiff enough to maintain its shape with less than 10% change in volume in an ambient environment with a pressure above the device pressure such as 5 mmHg, 10 mmHg, 20 mmHg, 30 mmHg or intermediate or higher pressure. Optionally, change in volume is defined by change in total volume or by the degree of spatial overlap between the volume with and without pressure, as a percentage of the original volume. Optionally, the rigid elements are resilient and may be deployed deformed, optionally formed of shape memory and/or super-elastic material. Optionally or alternatively, the rigid elements are deformed by deployment and/or include predefined folding regions for deployment.

In some exemplary embodiments of the invention, at least 20%, 40%, 60%, 70% or smaller, intermediate or larger percentages of the surface of the device inside the abdominal cavity do not have an underlying rigid or rigidizing element.

In some exemplary embodiments of the invention, rigidization is provided by inflation of one or more chambers formed in the device. Optionally, the device, at least in part, is formed of a double layer of fluid or gas impermeable material, which are sealed to each other to define chambers and, optionally, fluid provision pathways.

In some exemplary embodiments of the invention, the chambers or other types of rigid elements are interconnected to each other (or not) and flexible material spans spaces therebetween in a way which avoids a single point of failure. For example, a plurality of rigidization compartments or elements are provided and failure of a single one or tearing of a thin section between two such compartments, does not cause failure of the device as a whole. In some exemplary embodiments of the invention, the rigid elements are interconnected to the membrane, preventing the propagation of a tear past a neighboring rigid element. In some exemplary embodiments of the invention, each rigid element is independently fallible. For example, if the rigid elements are inflatable chambers, at least some chambers have a separate valve and/or inflation pathway, so failure of one does not mean failure of all. If the ribs are inserted in channels, the channels may have separate welds.

In some exemplary embodiments of the invention, the membrane includes one or more threads or other flexible strengthening elements, and that lie between ribs, so as to slow or prevent propagations of tears past the strengthening elements.

In some exemplary embodiments of the invention, if a first workspace device tears or otherwise fails, a second workspace device may be inserted (e.g., through another incision) and the first workspace device inserting into an orifice of the second device. The second workspace can be used as a patch (e.g., its lips 202 closing over the neck part of the first workspace device). Alternative, the contents of the first device are emptied into the second device and the first device removed and the second bag sealed and used to process tissue.

In some exemplary embodiments of the invention, the device is rigidized in steps, for example, a first rigidization of one or more components is used for deployment into the body. A second rigidization of one or more components is used for deployment and/or a third rigidization is used to close and/or seal an opening through which tissue is inserted into the workspace. In some exemplary embodiments of the invention, steps are provided by sequential inflation of different chambers, for example, using an automated inflator, or by manual inflation of each one, when desired. In some exemplary embodiments of the invention, one of the steps comprises retracting a tensile element, thereby modifying the shape of a rigidifying element of the device.

In some exemplary embodiments of the invention, rigidization of the workspace device is provided by insertion of rigid elements and/or by bending of existing rigid elements (e.g., at pre-defined bending areas or hinges). In some embodiments of the invention, the device defines channels (e.g., between welded layers of thin material), into which such rigid elements may be inserted.

In some exemplary embodiments of the invention, rigidization is provided by releasing (e.g., by sheath retraction) of existing rigid elements to expand to a pre-defined state. In some embodiments of the invention, rigidization is provided by interlocking of rigid elements, optionally after rearrangement thereof, for example, using a structure similar to that of an umbrella to lock together rigid elements that define a dome shape. Optionally or additionally, the thin membrane between the elements serves are part of the rigidifying structure, again, for example, as in an umbrella, by acting as a tensioning element. In some exemplary embodiments of the invention, the membrane is elastic and resists, to some extent, the bending of the rigid elements.

A potential advantage of such rigidization, in some embodiments thereof, is that the workspace can have a lower internal pressure than the abdomen and not collapse.

Another potential advantage of rigidization, in some embodiments thereof, is protection of organs in the body from forces applied inside the workspace.

Another potential advantage of rigidization, in some embodiments thereof, is allowing the workspace to be open to the body lumen while maintaining its shape. It is a particular feature of some embodiments of the invention that the rigidization elements may be maintained in place and rigidity during tissue processing, at least such elements as maintain the shape of the workspace.

Another potential advantage of rigidization is that the thin membrane is protected from being inadvertently processed by an inserted morcellator. In some embodiments of the invention, the thin membrane between the rigidization elements deflects inwardly (e.g., due to external pressure) less than 10 mm, 5 mm, 3 mm or intermediate distances, relative to a surface of a minimal convex object interconnecting the rigid elements.

An aspect of some embodiments of the invention relates to providing a negative pressure differential (or at least no significant positive differential) between an inside of a workspace and the surrounding tissue while the workspace is expanded. In some exemplary embodiments of the invention, this differential is made possible by the existence of one or more rigid elements maintain the shape of the workspace against such pressure difference.

In some exemplary embodiments of the invention, the provision of the pressure differential compensates for any leaks in a sealing and/or in a body of the workspace device, and prevent or reduce leakage of tissue or tissue parts back into the body lumen, once it had been provided into the workspace for processing.

A potential advantage of such negative pressure, in some embodiments thereof, is the avoidance of over-interfering with a surgical procedure, as neither insertion, nor deployment, nor usage, nor removable of the workspace device necessarily require abdominal decompression in some embodiments.

In some exemplary embodiments of the invention, there is equal pressure in the workspace and the body. This may be provided by the workspace including one or more apertures which are gas permeable and cell impermeable. Optionally, the apertures are provided in the form of a membrane which has these properties.

In some embodiments of the invention, the workspace device may be inflated after sealing thereof.

An aspect of some embodiments of the invention relates to a workspace device with a tissue entry orifice, which is closed after the tissue is inserted into the workspace. In some exemplary embodiments of the invention, the orifice is sealed, to prevent tissue particles from leaving the workspace back to the body lumen. It is a particular issue of some embodiments of the invention that the tissue entry office may coexist with an additional orifice open to the outside of the body.

In some exemplary embodiments of the invention, the orifice is in the form of a side opening in the workspace. In some exemplary embodiments of the invention, the orifice is formed between rigid or rigidifiable parts of the workspace device.

In some exemplary embodiments of the invention, the orifice is between 10% and 30% of an outside surface area of the workspace, of the portion intended for intrabody locating. In some exemplary embodiments of the invention, the orifice is significantly larger, for example, between 30% and 50%, 70, 80% or intermediate or greater percentages. In some embodiments of the invention, these percentages are of a surface of a geometrical object defined by the workspace. For example, the workspace may function as a frame, and once the organ or other tissue is placed therein, the frame is covered with a covering to provide sealing against the body lumen.

In some exemplary embodiments of the invention, the orifice has a normally open state and is closed when needed. Optionally or alternatively, the orifice has a normally closed state and can be opened when needed.

In some exemplary embodiments of the invention, the orifice is in the form of a valve (e.g., a flap valve), optionally supporting insertion of tissue into the workspace, but not egress out of the workspace. In some exemplary embodiments of the invention, the use of a valve is made possible by the rigidifying elements which maintain the shape of the workspace and/or by dedicated rigidifying elements associated with the valve itself and which may provide support to the valve.

In some exemplary embodiments of the invention, the orifice is designed to be sealed. Optionally, the orifice is designed to be sealed to itself or other part of the workspace device. Optionally or alternatively, the orifice is designed to be removed from the body (while the workspace remains in the body, thereby sealing the orifice from the body lumen. Optionally or alternatively, the orifice is designed to seal against tissue, for example, allowing a portion of tissue being treated to remain in the workspace, while connected parts of the tissue remain outside the workspace. This may be useful for draining cysts, where the cyst is brought into the workspace, drained and possibly ablated, while not overly damaging the rest of the tissue. This may allow the tissue damage to avoid damage (e.g., cutting) otherwise possibly necessitated by dealing with a bloated cyst.

In some exemplary embodiments of the invention, closing of the orifice and/or sealing thereof are by manipulations performed from outside the body, for example, pulling on a drawstring which extends to outside the body. Optionally, the drawstring is used for one or more of closing the orifice, sealing the orifice, rotating the workspace and/or extending the orifice out of the body.

In some exemplary embodiments of the invention, closing the orifice comprises closing a zipper. In some exemplary embodiments of the invention, closing the orifice comprises pulling a part of the workspace surface towards the outside of the body. In some exemplary embodiments of the invention, closing the orifice comprises folding a portion of the surface over the workspace. In some exemplary embodiments of the invention, closing comprises sliding or rotating one part of the workspace device relative to another. In some exemplary embodiments of the invention, sealing is not provided, for example, due to existence of a negative pressure differential between the workspace and the body lumen, which may sufficiently reduce or prevent tissue escape from the workspace.

In some embodiments of the invention, the workspace is closed, sealed and/or otherwise manipulated using a laparoscopic tool inserted from outside the body, optionally through its own port, and which access the outside of the workspace.

In some exemplary embodiments of the invention, the closure and/or sealing mechanism, when sealed and/or closed, is concave or flat and/or otherwise lacks protrusions away from the workspace device surface. This may help avoid parts of the workspace device snagging on body parts or medical tools during removal. Optionally, the closure and/or sealing mechanism have a minimum radius of curvature above 3 mm, 2 mm or 1 mm. Optionally or alternatively, the mechanism may or extends less than 3 mm, 2 mm, 1 mm, outwards from a surface of the workspace. Optionally or alternatively, such projection, and/or greater projection is of a material and/or geometry which does not damage tissue by contact thereof under small forces. It is noted that the parts of the device designed for intra-abdominal position may have such properties in addition to or instead of just the sealing and/or closing mechanism.

In some exemplary embodiments of the invention, the sealing mechanism comprises adhesive. Optionally, the adhesive is covered and is revealed, for example, by removing a cover layer, for example, using a drawstring. Optionally or alternatively, the adhesive is release from a reservoir using a zipper mechanism and/or by pinching together of lips of the orifice, for example, using a grasper.

In some exemplary embodiments of the invention, sealing is provided, at least in part by folding an extension of lips of the orifice.

In some exemplary embodiments of the invention, sealing is provided, at least in part by radially contracting together an extension of lips of the orifice, for example, using a ring. In some exemplary embodiments of the invention, sealing is provided, at least in part by pulling on a purse-string suture surrounding the orifice.

In some exemplary embodiments of the invention, sealing is provided, at least in part by applying suction by the lips to a surface in contact with the lips.

In some exemplary embodiments of the invention, the lips extend away from the rest of the device, for example, between 1 and 30 mm, for example, between 2 and 10 mm. Optionally, such extensions are soft. In some exemplary embodiments of the invention, the extension is much larger, for example, above 30 mm, above 50 mm, above 100 mm, above 200 mm, or intermediate in size.

In some exemplary embodiments of the invention, after closure, a small gap remains. Optionally, this gap is closed by inserting a plug thereinto.

In some exemplary embodiments of the invention, the tissue is pushed in to the orifice, for example, using the morcellator and/or using a gripper or other tool. In some exemplary embodiments of the invention, the tissue is pulled into the workspace, for example, by a morcellator, gripper or other tool extending into one aperture of the workspace and out the orifice. In one example, the morcellator applies vacuum to grasp the tissue during manipulation thereof. In another example, the orifice is larger than 180 degrees in extent and the workspace device or at least a membrane portions thereof is deployed around the tissue.

An aspect of some embodiments of the invention relates to a workspace device with two openings, one for insertion of tissue and one for insertion of a morcellator or other tissue processing tool. Optionally, the two openings remain at least 2 cm apart during use of the device. In some exemplary embodiments of the invention, one opening is to the side of the workspace and one opening is at a top of the workspace (e.g., where it is inserted into the body). In some embodiments of the invention, one opening extends to the outside of the body also while tissue is inserted into the workspace. Optionally or additionally, the locations of at least one opening relative to the workspace is maintained using a rigidifying element which interconnects them.

In some embodiments of the invention, an opening which is intended for tools for processing the tissue, for example, a morcellator, always extend to outside of the body. It is a particular feature of some embodiments of the invention that a different opening is used for inserting the tissue into the workspace than the one used for inserting tools, such as a morcellator.

It is a particular feature of some embodiments of the invention that no access is made to the tissue in the workspace from inside the abdominal cavity (or other body lumen) after the tissue ingress orifice is closed.

In some exemplary embodiments of the invention, the workspace is in the form of a sleeve, with one opening at either end of a generally tubular shape (straight or bent). Optionally, in use, the tissue ingress opening is closed and optionally removed from the body, while the tissue and the space of the workspace device, remain in the body. Optionally, a cord is used to both close and draw this ingress opening out of the body. In some embodiments of the invention, the part of eth sleeve near the orifice is folded or otherwise compacted to a ring surrounding the orifice.

In some exemplary embodiments of the invention, one opening extends out of the body, also while the tissue is provided into the workspace. Optionally, this opening is used for insertion and retraction of the morcellator and/or other tissue processing tool. In some embodiments, both openings remain inside the body and are optionally both sealed during tissue processing.

An aspect of some embodiments of the invention relates to safety of using a workspace device, especially for morcellation and/or manipulation using hard-tipped tools, such as grippers.

In some exemplary embodiments of the invention, the safety comprises protecting the workspace device itself from being damaged by the tools being used, such as the morcellator or gripper. Optionally, a part of the workspace surface where such tools are expected to contact (e.g., opposite a tool entry opening), is protected by a mesh, optionally spaced apart from the wall and/or by thickening the wall at such a part. Optionally or additionally, the sensitive parts of the device (e.g., thin membranes) are maintained in a taunt and/or concave configuration relative to the morcellator so that they cannot be inadvertently processed thereby.

In some embodiments of the invention, the workspace device includes one or more sensors to detect damage or risk of damage thereto. Optionally, the sensor is associated with the volume of the device, for example, a pressure sensor which can detect changes in volume that indicate a leak. In some embodiments of the invention, the sensor is associated with the surface of the device, for example, a conductive mesh which can be used, e.g., using impedance measurement, to detect a proximity of a metal tool tip to the surface. Optionally or additionally, the sensor detects a mechanical property of the surface itself, for example, strain or tears. In some embodiments of the invention, the sensor is in the form of a conductive mesh or an array of mechanical sensors embedded in the wall. In some exemplary embodiments of the invention, the sensor comprises a tube interconnecting inflatable chambers of the device with an indicator outside the body. Failure of an internal wall of the device will reduce pressure in one or more chambers, leading to reduction of pressure in the tube, which can be seen on the indicator, for example, electrically or mechanically. Optionally, a circuitry is attached to the tube and includes or is connected to a user interface for displaying an alert to a user. Optionally or alternatively, such a tube may carry tissue or blood to outside the body, also providing a visual indication.

In some exemplary embodiments of the invention, the safety comprises prevention failure of the procedure. For example, the workspace device, may be set up to fail gradually (e.g., a hole formed) rather than catastrophically (all the innards of the workspace volume spray out). For example, the device may include a plurality of independently fallible rigidifying components, such that only one fails at a time, rather than the entire structure. Optionally, at least 4, 6, 8 or more such stand-alone components are provided. Optionally or alternatively, when in the form of a thin membrane connected between the elements, the elements are interconnected so that a tear (or other failure) in the membrane does not cause the elements to move apart and enlarge the tear.

In some exemplary embodiments of the invention, the safety comprises resilience in face of damage or manufacturing problems of the workspace device. Optionally, the provision of lower pressure in the workspace than in the abdomen and/or provision of continuous suction out of the workspace prevents any surface integrity problems from allowing tissue debris to exit the workspace into the body. Optionally or alternatively, a suction source (e.g., a tube extending into the workspace, optionally to a bottom thereof) is provided to extract, optionally continuously, tissue fragments, so that any leak will have less material to leak out. Optionally, blood coagulator or absorbent material may be provided in the workspace and/or on lips of the orifice and/or near the orifice and/or between layers of the wall of the device (e.g., to be activated if a wall is breached).

In some exemplary embodiments of the invention, safety comprises safety of other, nearby organs. Optionally, the workspace is made soft enough and/or has a thick enough wall (e.g., a double inflated wall or sponge filled wall), so that tools moving inside the workspace device are less likely to damage nearby organs through the wall of the device.

In some embodiments of the invention, the wall of the device is a double wall, which is optionally filled with, for example, gas, fluid or a foam material, and which can provide softening of the outer wall and/or resistance to force and/or tool transmission therethrough. Optionally, the wall is connected to a vacuum source, so that damage to a surface of the wall, causes tissue particles to be sucked away, rather than potential leak out of the device.

In some exemplary embodiments of the invention, safety relates to user safety. In some exemplary embodiments of the invention, a seal is provided between the morcellator and the workspace, for example, in the form of a valve as part of the workspace device and outside the body or on the path to outside the body, through which valve the morcellator is inserted and removed. Optionally, the same valve or an additional valve is used for inserting and/or removing a different tool, such as a gripper or other tissue manipulator, used in tissue processing.

An aspect of some embodiments of the invention relates to the workspace volume being operative to be used for working on tissue, rather than just for tissue retrieval. In one example, the workspace is transparent or includes one or more transparent windows on the body or in a valve thereof allowing viewing of its inside from outside thereof. In another example, the workspace includes one or more valves for insertion and/or removal of tools for tissue processing, from within the abdominal cavity.

An aspect of some embodiments on the invention relates to integrating the use of a morcellator into laparoscopic or other minimally invasive procedures. In some exemplary embodiments of the invention, the morcellator includes a laparoscopic port, for example, a port into the workspace volume or to a side thereof, thereby controlling intra-abdominal pressure (for abdominal laparoscopy), while allowing tool insertion and removal. Optionally, this allows the workspace to be inserted early in the procedure and be physically collocated with a gripper or other tool. Optionally, the gripper passes through the workspace volume itself. Optionally, the workspace volume is axially collapsed during such deployment until a workspace volume is needed. Optionally, this allows tissue to be pulled into the workspace device after deployment thereof.

In some embodiments of the invention, a tool inserted through a different port into the body lumen is used to access the workspace and/or the inside of the workspace volume, optionally through a valved opening in the workspace surface.

In some embodiments of the invention, the outside surface of the device is marked, for example, with a grid or with indications where gripping is safe, to assist in interaction with tools during a laparoscopic procedure.

An aspect of some embodiments of the invention relates to a workspace device which has an end adapted to be attached to an abdominal wall and a laterally directed orifice for inserting tissue into the device. In some exemplary embodiments of the invention, the orifice is smaller than a maximal cross-section of the device. Optionally or alternatively, the orifice remains in the cavity while the tissue is processed. Optionally or alternatively, the device includes an opening where it is adapted for attachment to the abdominal wall, for insertion of a tool therethrough.

In some exemplary embodiments of the invention, a lateral orifice is an orifice whose axis lies along a line no more than 30 degrees off from a perpendicular to a perpendicular to the abdominal wall, where the device is attached. The orifice axis may be defined as the perpendicular to a plane which most closely approximates the perimeter of the orifice (e.g., using RMS distance).

An aspect of some embodiments of the invention relates to a damage indicator for a laparoscopic bag, in accordance with some embodiments of the invention. Optionally, the indicator comprises a channel connecting a pressurized part of the bag to a location outside the body. Change in pressure in the bag, which can indicate damage thereto, can be indicated, for example, visually, by a collapse or expansion or other movement of an indicator attached to the channel. Optionally or alternatively, a pressure sensor is used. Optionally or alternatively, a UI circuit is used to generate an alert, for example, a colored LED, or a sound. This indicator may be used for bags designed to be used at a pressure above, below or even at that of the abdominal cavity.

A broad aspect of some embodiments of the invention relates to a workspace device which deploys by inflation, where the workspace device is rigidized by inflatable compartments of the workspace device. In some embodiments, the inflated workspace device is sufficiently rigid to resist pressure levels within an insufflated patient cavity.

In some embodiments, after isolation of the workspace device from the abdominal cavity and, in some embodiments, at least partial inflation of the workspace device, pressure within a lumen of the workspace device is increased to a level which is higher than that of the abdominal cavity (e.g. including one or more feature as described previously in this document). In some embodiments, a pressure of inflation fluid within the inflatable chambers of the workspace device is increased after an initial inflation of the device. For example, in some embodiments, an inner pressure of inflatable chambers within the device required to expand the device being lower than the pressure required to withstand a pressure difference between the insufflated patient cavity and the isolated workspace device inner volume.

For example, in some embodiments, a pressure within expandable chambers of the device required to expand the device is 0.25-1 or about half an atmosphere, or lower or higher or intermediate ranges or pressures. For example, in some embodiments, a pressure within expandable chambers of the device required to rigidify the device sufficiently to prevent collapse of the device under abdominal cavity pressure is 1-4, or 1-3 or about 2 atmospheres, or lower or higher or intermediate ranges or pressure.

In some embodiments, the workspace device is delivered to a treatment site (e.g. patient cavity e.g. abdominal cavity) while in a collapsed configuration. In some embodiments, inflation of the compartments expands the workspace device from a collapsed configuration to an expanded configuration. For example, in some embodiments, an at least partially inflated compartment pushes against adjacent compartment/s the pressure acting to expand the workspace device. In some embodiments, inflation acts to unfold and/or unroll portions of the workspace device to transfer the workspace device from a collapsed configuration to an expanded configuration.

In some embodiments, the inflatable compartments of the workspace device form a plurality of circumferentially extending segments. Where, for example, in some embodiments, the circumferential segments each describe a circumference of a portion of a body of the workspace device. In some embodiments, the workspace has a tubular shape. In some embodiments, the workspace device has a tubular shape with varying cross sectional area, for example tapering. In some embodiments, the segments form a workspace body which includes at least a portion which is generally cylindrical in shape. A potential advantage of a generally cylindrical shape is increased structural strength and/or resistance to collapse under pressure, for example, in comparison to other shapes.

In some embodiments, the workspace has another tubular shape, for example, with oval cross section, and/or with a cross section with changing dimension and/or shape.

In some embodiments, the circumferential segments are each an inflatable compartment. In some embodiments, the workspace device includes a plurality of ring shaped compartments (e.g. toroid's e.g. with circular cross sections). In some embodiments, a cross sectional shape of one or more ring-shaped compartments or segments is elliptical, or semicircular or irregular in shape. In some embodiments, cross section of the ring-shaped segment/s varies at one or more circumferential portion. In some embodiments, the circumferential segments are sequentially contiguous, for example, in some embodiments, the workspace device includes a helical shaped chamber, each turn on the helical shape chamber defining a circumferential segment.

In some embodiments, compartments expand (e.g. by inflation) in a predetermined (and/or in some embodiments, a user selected and/or adjusted order) order. In some embodiments, the predetermined order is defined by a positioning of one or more inflation channels which convey fluid for inflation to the workspace device. Where, in some embodiments, inflation starts with a first chamber to which the inflation channel to which it is first fluidly connected, adjacent chamber/s inflating after the first chamber and, in some embodiments, chambers sequentially inflating with distance from the first chamber.

A potential advantage of controlled and/or predetermined and/or sequential expansion of the workspace device (e.g. by inflation) is improved control of positioning and/or manipulation of the device within the patient cavity, as, in some embodiments, rigidity of inflated portions enable accurate force transfer for moving the device and/or tissue within the device. Where, in some embodiments, inflation of a second chamber sequentially inflating after a first chamber includes the second chamber being inflated by at most 10% when the first chamber is inflated by at least 70%, or the second chamber being inflated by 0-20%, or 0-10%, or 1-10%, or 0-5%, or lower or higher or intermediate percentages or ranges when the first chamber is inflated by 60-100%, or 60-99%, or 70-100%, or 80-100%, or 90-100% or 95-100%, or lower or higher or intermediate percentages or ranges.

In some embodiments, more than one segment fills at the same time, for example, in embodiments, where more than one channel is used to inflate the device. In some embodiments, a plurality of inflation channels each serve (for inflation) one or more compartment, for example, allowing partial expansion of the workspace device. For example, in an exemplary embodiment, a first subset of the workspace chambers (e.g. subset of adjacent ring compartments) is fluidly connected to a first inflation channel and a second subset of the workspace chambers is fluidly connected to second inflation channel. In some embodiment each inflatable compartment is filled by a separate inflation channel.

In some embodiments, a user selects and/or controls (e.g. using one more valve, e.g. by using one or more hand pump and/or activating one or more pump e.g. by connecting one or more inflation channel to one or more pump) a workspace size and/or shape by selecting and/or controlling amount of fluid inserted into one or more inflation channel.

In some embodiments, a user, based on feedback (e.g. from one or more type of imaging e.g. from one or more sensor e.g. on the workspace device) controls inflation of the device, optionally, inflating different portions (e.g. axial and/or radial portions) at different times and/or at different rates and/or to different levels. In some embodiments, fluid which is used to inflate the chambers is a gas, for example, air and/or carbon dioxide. In some embodiments, the fluid used to inflate the chambers is a liquid, for example, water, saline. In some embodiments, the fluid used to inflate the chambers is a mixture of gas and liquid.

For example, in some embodiments, where inflation channel/s fluidly connect first to a top region of the workspace device (top, in some embodiments, referring to an opening of the workspace device e.g. where the workspace device has a single opening), inflation of the device starts at the top of the workspace device and extends downwards (e.g. towards a workspace device base), expanding the device in a downwards direction.

For example, in some embodiments, inflation channel/s fluidly connect first to a bottom region of the workspace device, the workspace inflating (and, in some embodiments, expanding) from the base upwards.

For example, in some embodiments, a middle section of the workspace inflates first followed by upper and lower portions, either sequentially or simultaneously.

In some embodiments, alternatively or additionally to control via fluid flow path, one or more valve controls an order of inflation of chambers (which, in some embodiments, controls direction expansion of the workspace device). For example, one or more first chamber including a valve between the chamber and an adjacent chamber, the valve opening (and allowing the adjacent chamber to inflated) only once a threshold pressure has been achieved e.g. when the first chamber is at least partially inflated. In some embodiments, a valve in a fluid pathway between chambers and/or between a fluid supply channel and a chamber is a one-way valve and/or is a valve which opens under a threshold pressure e.g. by rupture of a portion of the valve.

In some embodiments, alternatively or additionally to control via fluid flow path and/or valve/s, differing pressures required to inflate chambers controls the order of inflation of the chambers. In some embodiments, one or more chamber is configured to require a higher pressure to inflate (and, in some embodiments, the chamber then inflates after other fluidly connected chambers inflate). For example, the one or more chamber having walls adhered to each other and/or with high friction surface, inflation requiring the walls to separate. For example, in some embodiments, attachment of one or more chamber (e.g. in a collapsed configuration and/or to another chamber and/or a restraining portion) prevents filling of the attached chamber before other chamber/s are inflated. Where, for example, the attachment means that a higher pressure is required to expand the attached chambers, other fluidly connected chambers filling first. Where attachment includes one or more of glue, connector element/s.

In some embodiments, first a compartment at a base of the workspace device inflates, followed by upper compartments, for example, followed by a compartment adjacent to the base and sequentially after that adjacent compartments moving up the device. Towards, for example, an opening of the workspace device, where, in some embodiments, the workspace device includes a single opening, which, in some embodiments is at an opposite end of the device to the base.

In some embodiments, the predetermined order of inflation is from a top of the workspace device (which is in some embodiments, adjacent to a workspace device opening) downwards (e.g. sequentially) towards a base of the workspace device. For example, in some embodiments, the workspace device includes a helical shaped inflatable chamber, where, in some embodiments, an inflation channel is fluidly connected to a top of the helix proximal to the workspace device opening. Inflation of the chamber, in some embodiments, starting at the top of the workspace device and extending downwards, through the helical shape chamber, towards a base of the workspace device.

In some embodiments, inflatable compartments, when inflated, press up against each other to rigidize the workspace device. In some embodiments, the workspace device includes one or more gap between inflatable compartments, the gap/s providing windows through the workspace device, potentially enabling a user to view the patient cavity through the workspace (e.g. from camera images where the camera is located within the workspace). In some embodiments, gap/s are bridged by a connecting membrane.

In some embodiments, the workspace device includes two portions, where a first layer provides containment and a second portion, which includes inflatable portions, which provides rigidity to the structure. In some embodiments, the first layer sheaths the inner structure, forming containment between the abdominal cavity and the inner structure. In some embodiments, gap/s between inflatable compartments include holes, separation between the workspace and the patient cavity being provided by the first layer.

In some embodiments, at least a portion of workspace device has a generally cylindrical shape. In some embodiments, an inner lumen of a body of the workspace device has a shape which varies from cylindrical by at most 20%, or 10%, or 5%.

In some embodiments, the workspace device includes an opening which opens elastically during delivery of the workspace device, where, for example, in some embodiments, the workspace device is delivered to a patient cavity (e.g. abdominal cavity which is optionally insufflated) in a collapsed configuration where the opening is elastically compressed, and, upon deployment the opening is allowed to elastically relax. In some embodiments, delivery is through a deployment device, the workspace device being elastically compressed within the deployment device (e.g. within a lumen of the deployment device) elastically relaxing as the workspace device is delivered.

In some embodiments, inflation of the workspace device, optionally after opening (e.g. elastically opening) of the workspace device expands a body of the workspace device, in some embodiments, in a direction 40-120°, or perpendicular, or lower or higher or intermediate ranges or angles to a plane of the opening.

In some embodiments, the workspace device includes a closable orifice (e.g. as described elsewhere within this document). In some embodiments, the workspace device includes a single opening. In some embodiments, the workspace device includes more than one opening, one of which is a closable orifice.

In some embodiments, the workspace device is expandable, at least partially by one or more expanding framework, which in some embodiments includes one or more rigid portion. Before explaining at least one embodiment of the invention in detail, it is to be understood that the invention is not necessarily limited in its application to the details of construction and the arrangement of the components and/or methods set forth in the following description and/or illustrated in the drawings and/or the examples, if any. The invention is capable of other embodiments or of being practiced or carried out in various ways.

Referring now in detail to the drawings wherein like reference numerals identify similar or like components throughout the several views, various embodiments of the laparoscopic specimen retrieval device of the present invention are illustrated. The devices are designed to expand to a box-like structure to create a protected space within the patient's body. This enables the tissue particles to be isolated for removal, and in certain applications, enables morcellation of the particles without the risk of scattering the tissue within the patient's body. The configuration and rigidity of the device maintains its wall away from the specimen placed therein, reducing the risk of the wall of the device being cut by the morcellator and leaking contents from the device into the body cavity.

Exemplary Workspace Device

Figure 1B:
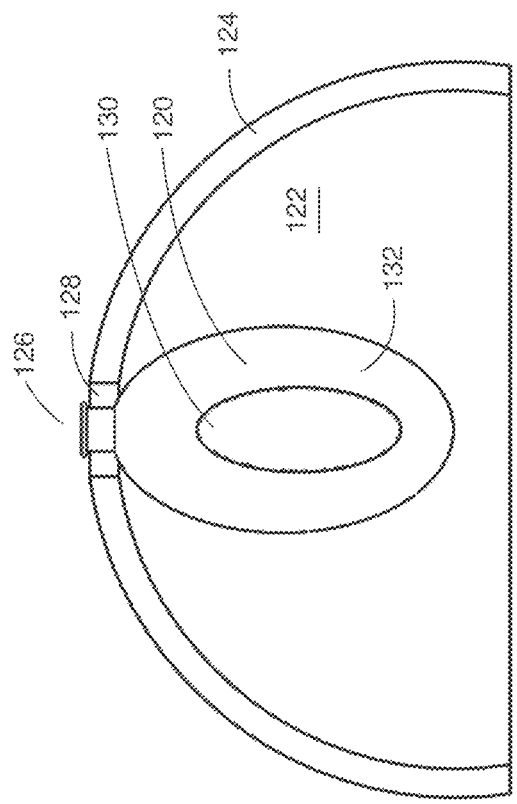

FIGS. 1A and 1B are side views of a workspace device 120 in an open orifice state (FIG. 1A) and a closed orifice state (FIG. 1B) in an abdominal cavity 122, in accordance with some exemplary embodiments of the invention.

FIG. 1A shows a schematic workspace device 120 inside an abdominal cavity 122, and inserted through an aperture 128 in an abdominal wall 124.

A tissue orifice 130 is shown in a body surface 132 of workspace device 120. In some embodiments of the invention, tissue is inserted into an internal volume 134 of workspace device 120 through orifice 130 for later processing. FIG. 1B shows device 120 in a closed orifice configuration, where orifice 130 is closed, allowing, for example, processing of tissue inside device 120 without contaminating tissue in abdominal cavity 122.

In some embodiments of the invention, processing includes inserting a morcellator or other tool through an opening portion 126 of device 120. Optionally, opening 126 includes or is fitted in a laparoscopic port. Optionally, opening 126 includes a valve, for example, inside volume 134 and/or outside of volume 134 (possibly as part of the laparoscopic port), but configured to press inward one or more flexible extensions of surface 132 against any tool inserted into device 120 through opening 126. In some embodiments of the invention, opening 126 includes a rigid structure (e.g., a laparoscopic port) which maintains aperture 128 open.

As will be explained below, in some embodiments, closing and/or sealing of orifice 130 is by extending a portion of the opening outside of the body. It is noted, that opening 126 optionally remains at and in aperture 128 throughout the usage of device 120.

Figure 2:
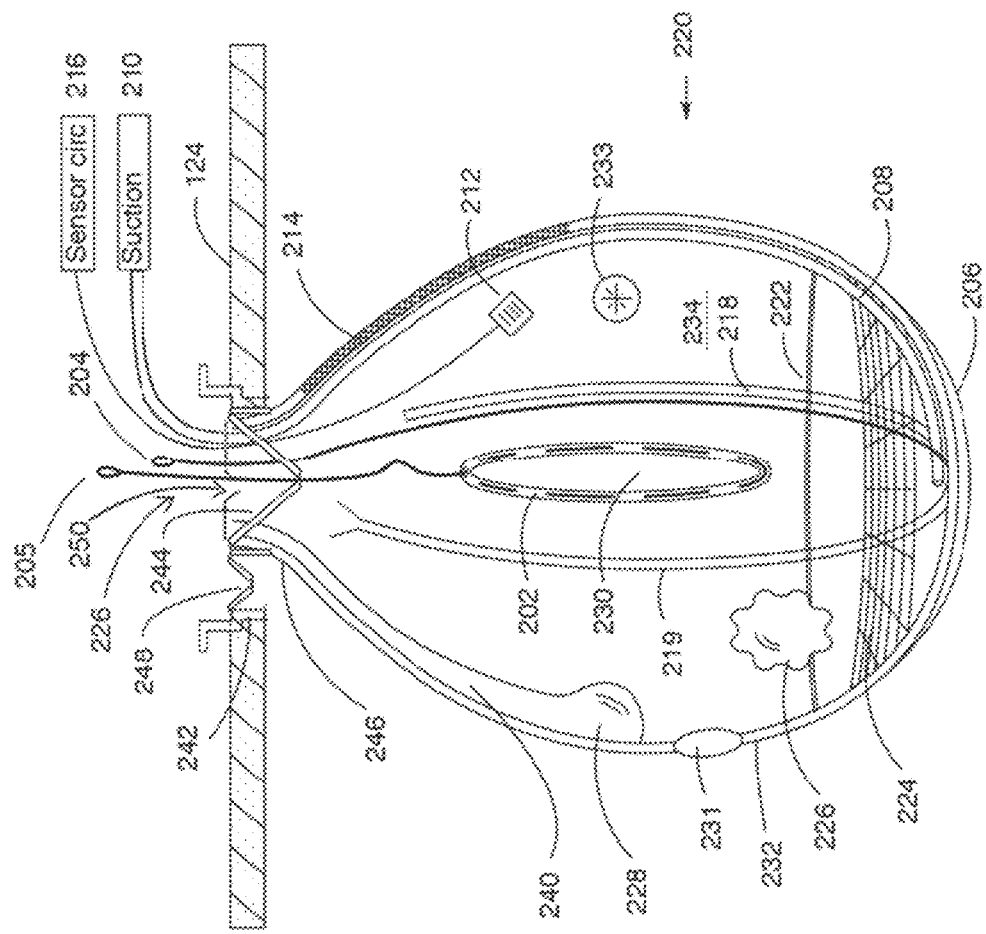
FIG. 2 is a side cross-sectional schematic view of a workspace device, including various optional features, in accordance with some exemplary embodiments of the invention.

FIG. 2 is a side cross-sectional schematic view of a workspace device 220, including various optional features, in accordance with some exemplary embodiments of the invention. Exemplary use of some of the optional features will be described in more detail in later parts of this document.

In some embodiments of the invention, device 220 has a body formed of a thin membrane (surface 232 which acts as a wall) stretched out between or bridging one or more rigidifying elements 218, 222. As shown, one or more vertical rigidifying elements 218 may be provided. Optionally or additionally, one or more horizontal and/or circumferential (e.g., longer than 30%, 50%, 80% or intermediate percentages of the circumference of device 220 where they are located) rigidifying elements 222 may be provided. Optionally or additionally, one or more helical elements or other shapes which extend in both vertical and horizontal directions, may be used.

A channel 219 is shown, which is adapted for later insertion of a rigidifying element thereto. Optionally, the channel is formed by welding of a layer to the thin membrane. In some embodiments, a rigidifying cage or structure is inserted into volume 234 without a dedicated channel.

Figure 16:
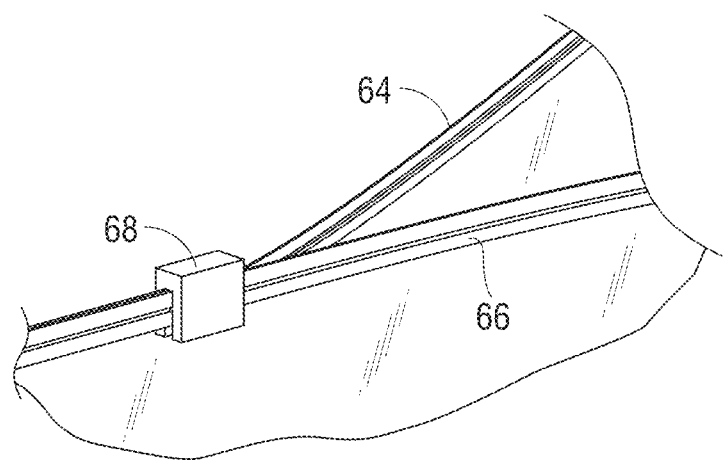
FIG. 16 is a close up view of one embodiment of a closing mechanism.

An orifice 230 is shown, optionally with a vertical orientation and which includes a lip 202. In some embodiments of the invention, lip 202 includes one or more rigidifying member for shaping orifice 230 (e.g., and setting it to normally open or normally closed states). Optionally or additionally, lip 202 includes a closure and/or sealing mechanism (e.g., a zipper as described for example in FIG. 16). Optionally or additionally, lip 202 includes a compacted sleeve, for example an extension of membrane 232, for example, as may be used for a sleeve embodiment of FIGS. 9A-N.

Optionally, a manipulation element 204, for example, mechanical pull element is provided to manipulate lip 202. In one example, element 204 is a wire which forms an extension of a purse-string suture for closing orifice 230. In another example, element 202 serves to pull a zipper shut. In another example, element 202 when manipulated, releases adhesive to adhere lips 202 together. In embodiments where the rigidifying elements are inflatable or where lips 202 include an inflatable compartment, element 204 may be used to deliver fluid, such as gas or liquid, optionally using a syringe.

Some parts of surface 232 may be thickened 206, or be double walled.

In some embodiments of the invention, a protective layer 224, for example a mesh, is provided, optionally spaced apart from wall 232 of volume 234, to protect wall 232 from mechanical damage.

In some embodiments of the invention, additional material, such as a coagulant 226 are attached to inside surface 232. Alternatively, such materials may be added later.

In some embodiments of the invention, volume 234 includes a connection to a suction source 210, for example, a pump. Optionally, the connection comprises a channel 208 which may extend to a bottom of the volume (e.g., where fluid is expected to collect gravitationally) and/or into a double layered wall section 206.

In some embodiments of the invention, device 220 includes a sensor circuitry 216 for processing signals received from device 220, for example, from a sensor 212, such as a pressure sensor. Optionally, circuitry 216 generates an alert, for example, if pressure increases indicating a wall breech and/or sends data to a processing unit (not shown), for example a workstation. Optionally, a planar sensor 214 is used and mounted to or in wall 232. In one example, sensor 214, which may be in the form of a conductive mesh or grid, is operated as an impedance sensor which detects the proximity of metal tools and/or objects which deform electric fields. Optionally or additionally, sensor 214 includes one or more stain sensors for detecting a strain on wall 232, especially strain as may be caused by contact of a tool thereon. Optionally or additionally, sensor 214 includes one or more (conductive) tear fuse sections which tear before or with wall 232 and generate an indication of damage thereto (e.g., when their electrical resistance goes up).

In some embodiments of the invention, there is provided a chamber 228 for an optical instrument for viewing operations inside device 220. Optionally, a channel 240 extends from outside the body to chamber 228 and may be used to insert a camera, optionally in the form of an endoscope. Optionally, chamber 228, which may be elastic and/or flexible allows bending and/or rotation of a tip of such an imager, to control viewing field thereof.

Referring now to an opening portion 226 of device 220, which is optionally configured to remain partly outside and partly across abdominal wall 124 through the use of the workspace, including deployment thereof. In some embodiments of the invention, opening 226 includes a rigid frame 242, which may be a part of a laparoscopic port and/or otherwise maintain open the point of insertion through abdominal wall 124.

In some exemplary embodiments of the invention, wall 232 extends into opening 226 (outside or inside of frame 242) as a neck/tube 246 so as to provide a continuous covering for volume 234. In some embodiments of the invention, the top (e.g., proximal side) of tube 246 is sealed with a valve 244 which optionally closes around a morcellator (or other tools) when inserted and which may prevent spraying of tissue from device 220 into the room. In some embodiments of the invention, one or more additional openings 250 into volume 234, are provided, optionally valved. In some embodiments of the invention, a valved opening 248 is provided between tube 246 and frame 242 and which may be used for inserting tools which can access the outside of workspace device 220. Optionally, valve 248 is compressible to a more flat configuration when a larger tool is inserted into tube 246, for example, the walls of tube 246 being properly sized and/or being elastically compliant.

A laparoscopic port is not shown for brevity in many of the figures herein. Also, it is noted that while some parts may be shown as entering abdominal wall 124 through a separate opening than used for the device, this is sometimes done to more easily distinguish the different objects entering the body, but a single hole may be used. Similarly, the wound in the abdominal wall is generally shown open, even when it would naturally collapse on the device. Also similarly, the thickness of the abdominal wall is schematic and an actual patient may have a thicker wall, due, for example, to subcutaneous fat layers. Optionally, neck 246 is selected to be long enough to cross this distance and/or any fixed tubular portion of a port, if used.

Exemplary Laparoscopic Procedure Using Workspace Device

Figure 3:
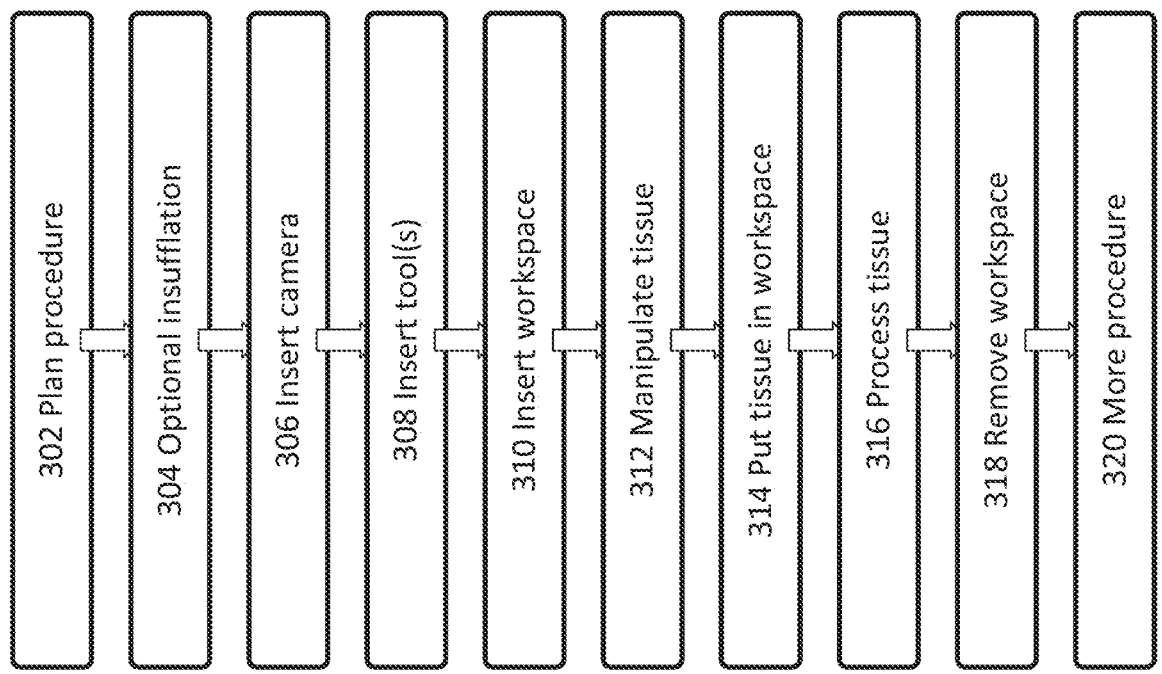
FIG. 3 is a flowchart of a method of laparoscopic treatment using a workspace device, in accordance with some exemplary embodiments of the invention.

FIG. 3 is a flowchart of a method of laparoscopic treatment using workspace device 220, in accordance with some exemplary embodiments of the invention.

At 302, the procedure is planned, for example, removal of a kidney, a uterus, a portion of GI tract or a tumor. As part of the planning a particular workspace device may be selected and/or an insertion location therefore planned. For example, if a procedure involves removing one large organ (e.g., a kidney) and several small pieces of tissue, a suitably sized device 220 may be selected. Optionally or additionally, the shape of the deployed workspace is chosen according to a location within the abdomen and nearby tissue and/or a tissue insertion direction, for which it will be used. Such choosing and selecting may also be done later in the procedure.

At 304 the abdominal cavity (if that is the body lumen treated) is optionally insufflated. Insufflation may also be done at a later stage, optionally following standard guidelines for laparoscopic procedures. It is noted that in some embodiments of the invention insufflation practices are not changed due to use of workspace device 220, as compared to a procedure without tissue removal.

At 306 and 308 a camera and/or other tools, maybe inserted, for carrying out the procedure, for example, following standard methods of laparoscopic surgery. In some exemplary embodiments of the invention, one or more tools may be inserted into the abdominal cavity through device 220, so device 220 will be inserted first.

FIGS. 11-18 show an exemplary embodiment of a workspace device 10, including exemplary usage steps in FIGS. 13-21.

Figure 13:
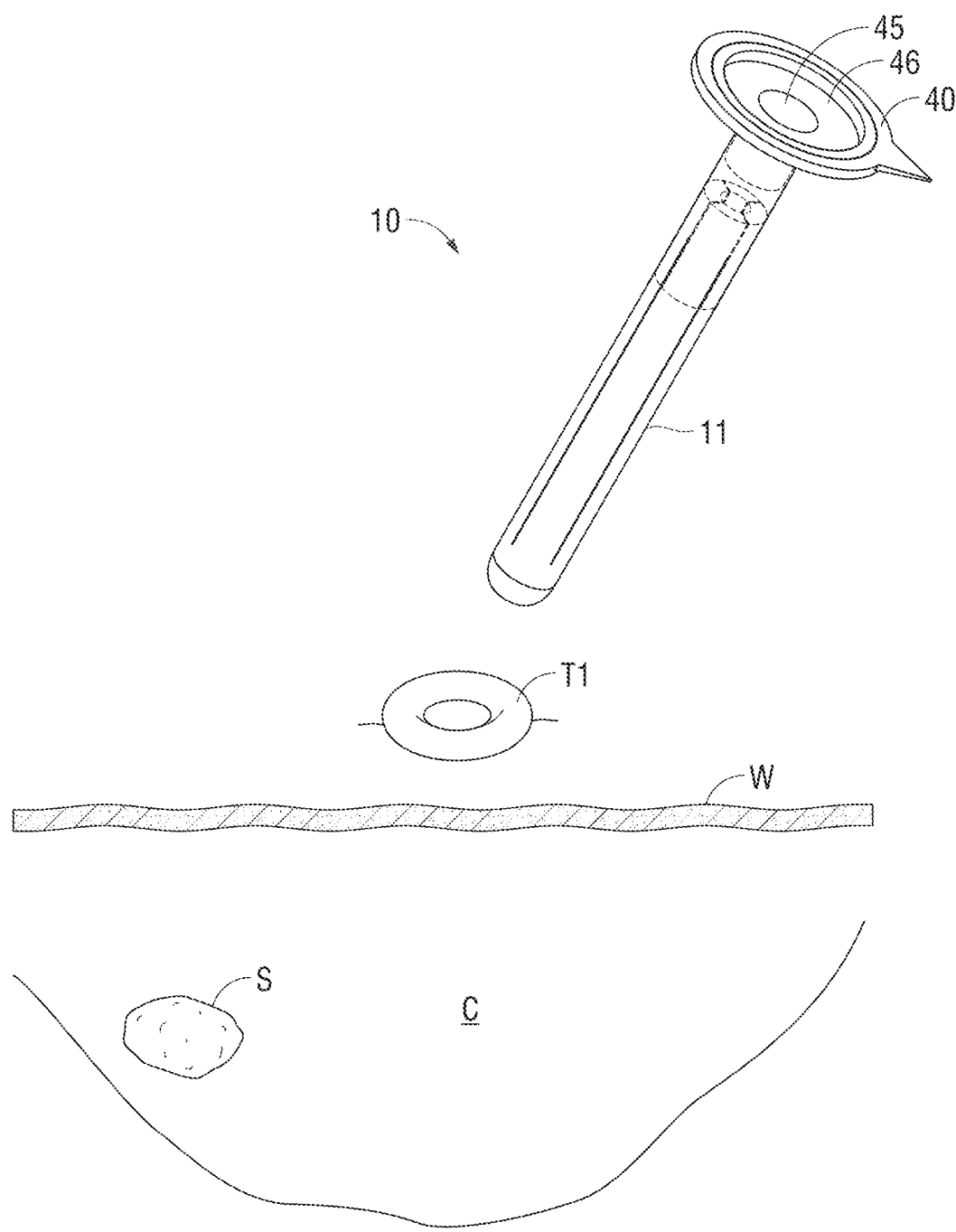
FIG. 13 is a perspective view of the device of FIG. 11 shown prior to advancement through a trocar positioned in the abdominal wall to retrieve a specimen from the abdominal cavity.
Figure 14:
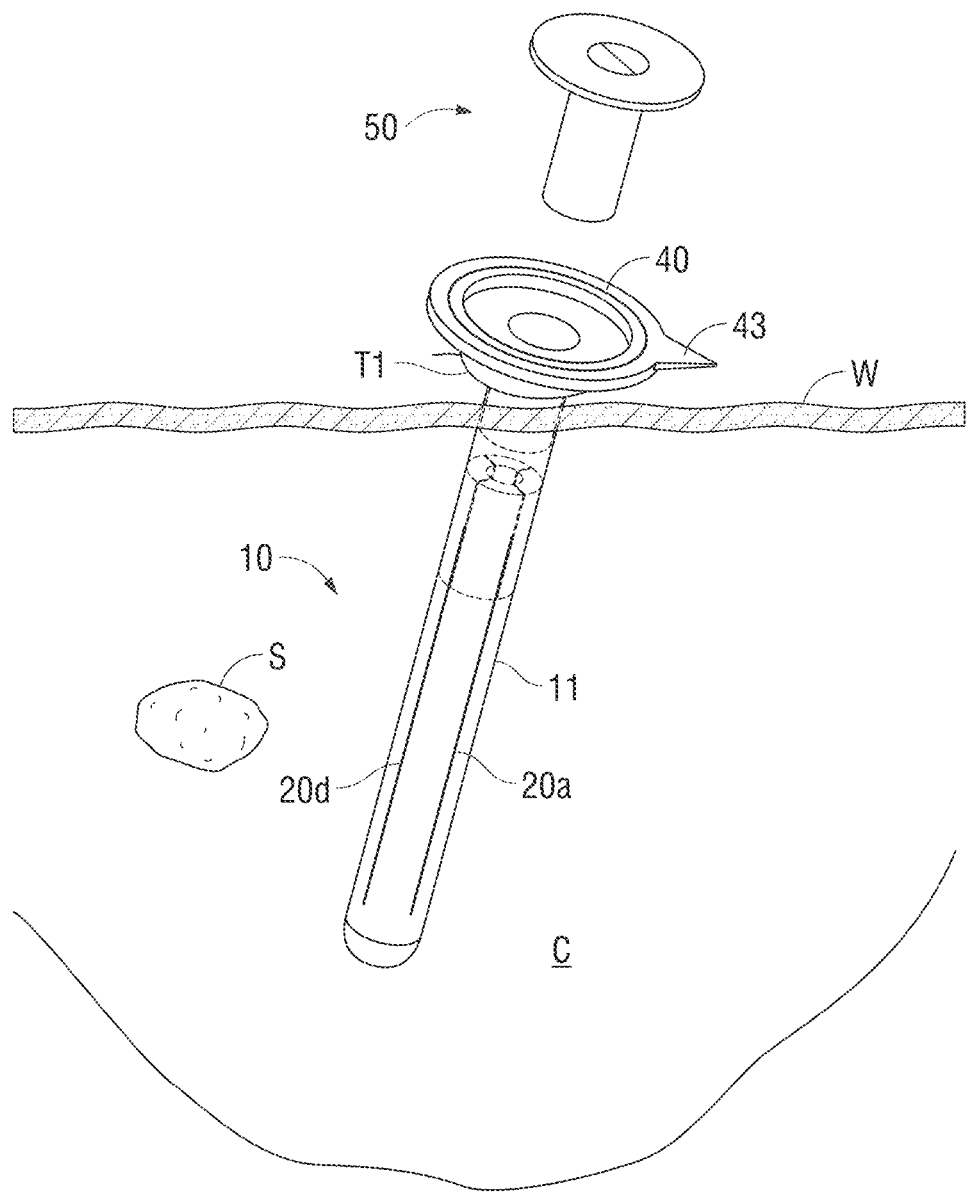
FIG. 14 is perspective view of the device of FIG. 11 shown inserted in a collapsed configuration through the trocar into the abdominal cavity.
Figure 15:
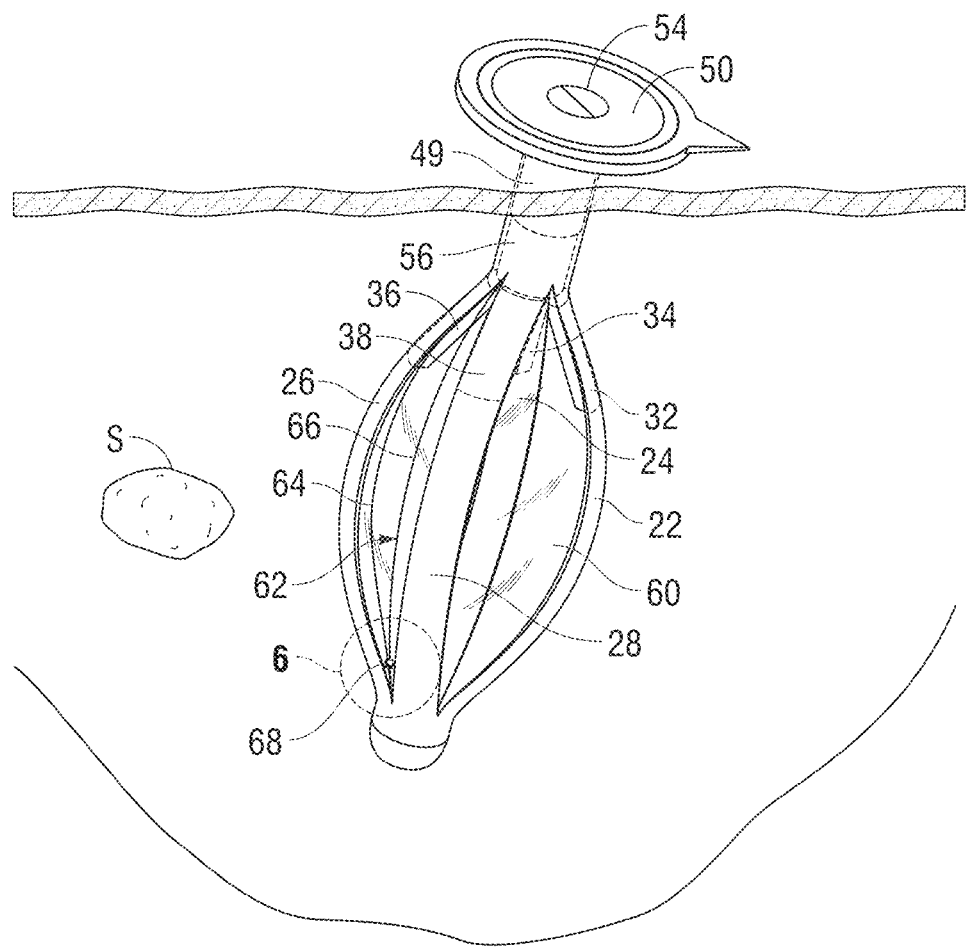
FIG. 15 is perspective view similar to FIG. 14 showing the expander positioned within the tube and the device in the expanded configuration.

At 310, a workspace device is inserted, for example, during an existing or through a dedicated incision in the abdominal wall. In some embodiments, the workspace device is inserted at the beginning of the procedure long (e.g., 10-15 minutes or more) before the workspace device is needed. In some embodiments of the invention, the workspace device is maintained in a less obtrusive configuration until it is needed. Alternatively, device 220 is inserted nearer to when it is needed, for example, just before tissue is cut away or after it is cut away, for removal thereof. FIGS. 13-15 show insertion and deployment of a workspace device 10 (called below a retrieval device) through a laparoscopic port 11.

At 312 tissue is manipulated, for example, selected or cut away from other tissue. In FIG. 13 a tissue 8 is already separated from other tissue.

Figure 17:
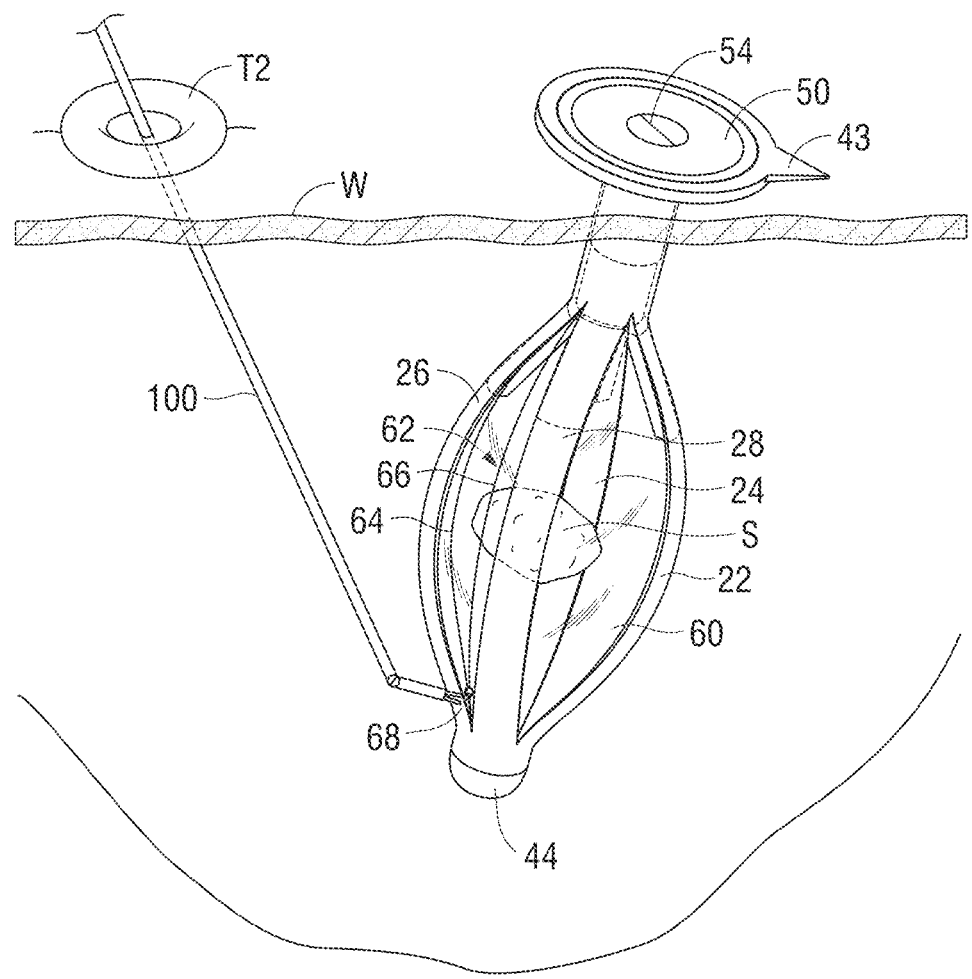
FIG. 17 is perspective view similar to FIG. 15 showing a grasper inserted through another trocar port for sealing the device once the specimen is placed within the device.

At 314, the selected tissue is placed inside volume 234, for example, pulled in or pushed in, using a gripper. FIG. 17 shows tissue 8 inserted into device 10.

Figure 18:
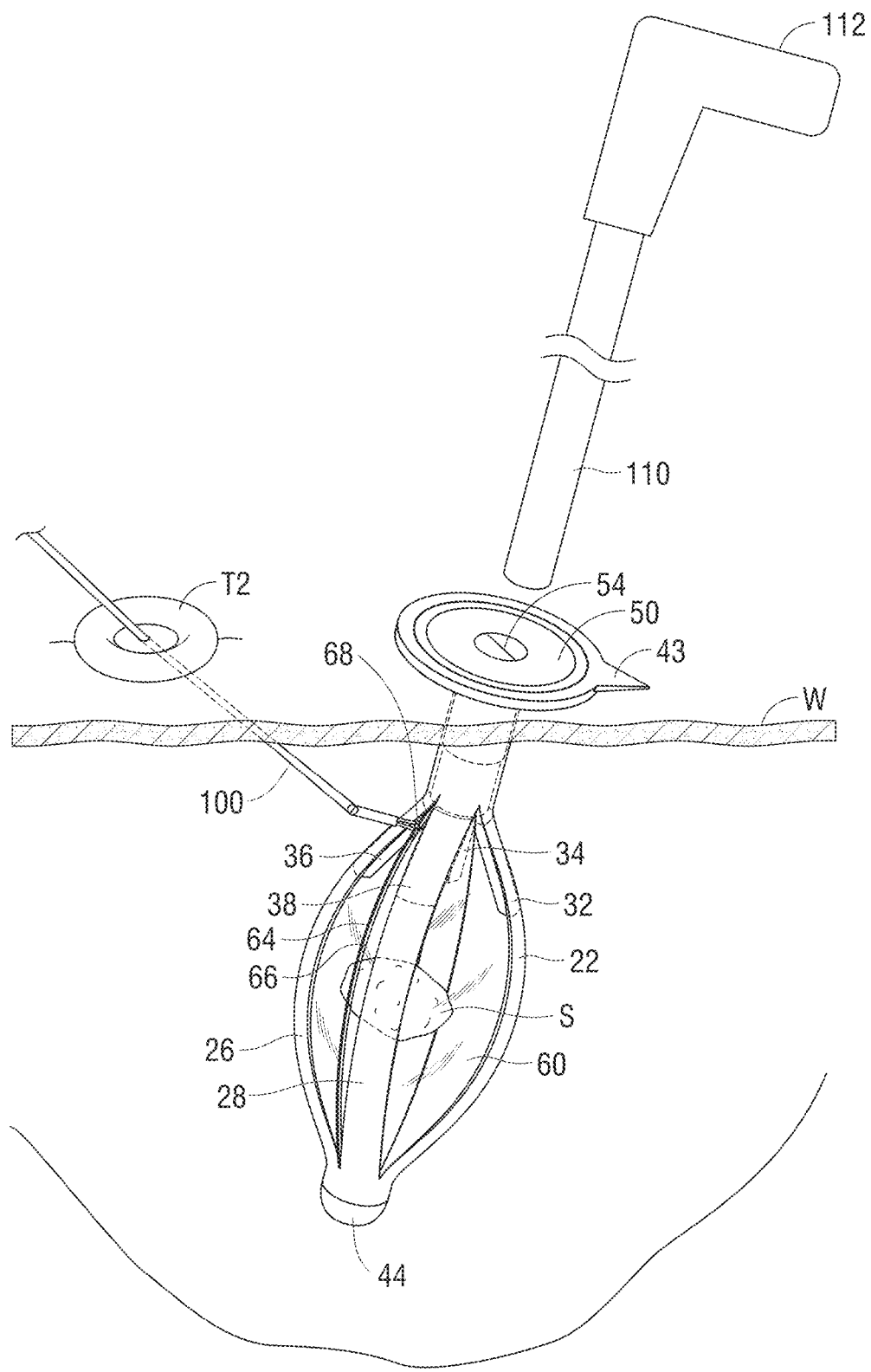
FIG. 18 is perspective view similar to FIG. 16 showing the grasper sliding the lock of the locking mechanism of FIG. 16 to seal the device and further showing a morcellator prior to introduction through the trocar into the device.
Figure 20:
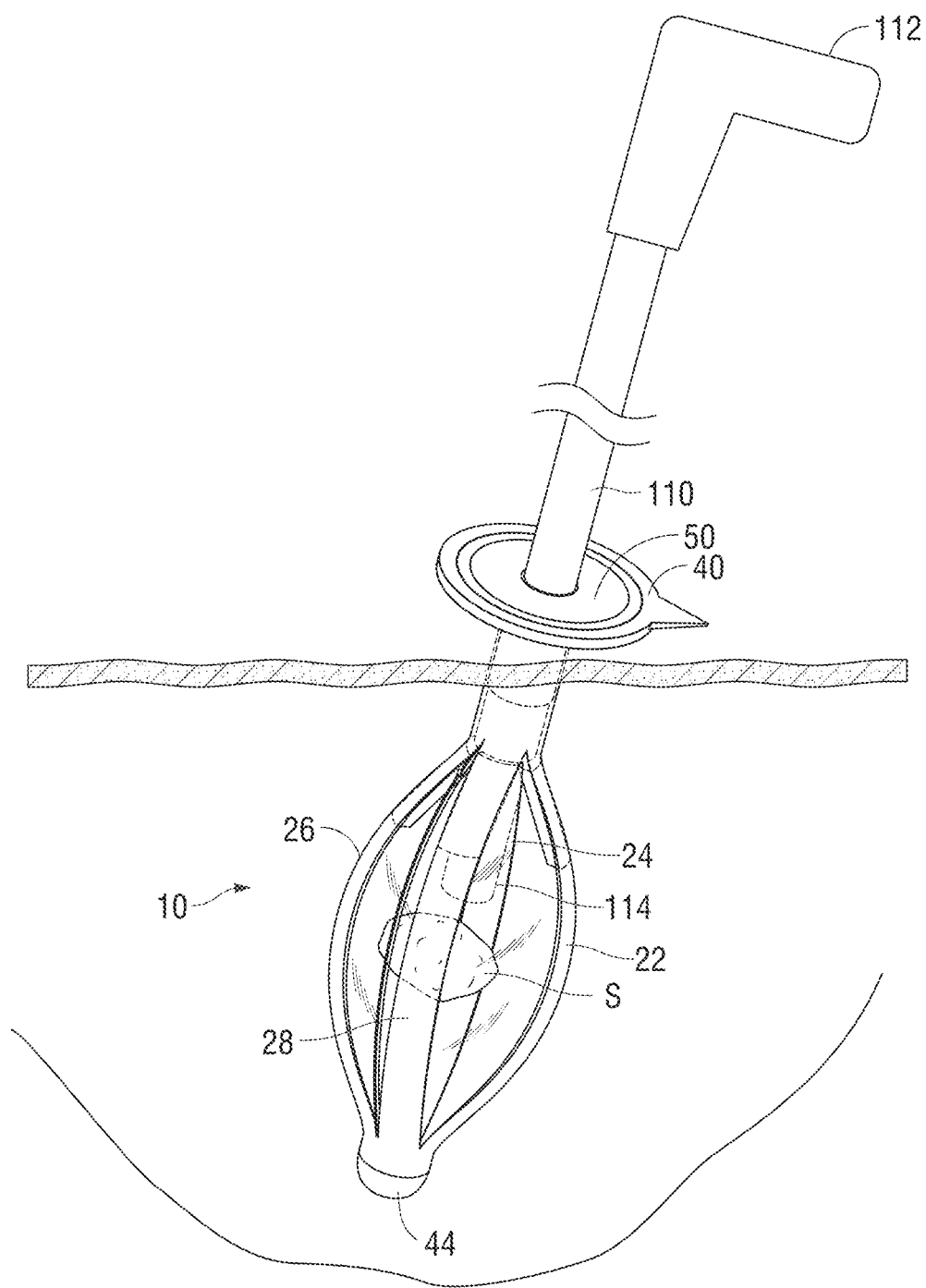
FIG. 20 is perspective view similar to FIG. 18 showing the morcellator inserted into the device for breaking up the specimen within the device.

At 316, the issue is processed, for example macerated. In some embodiments of the invention, the abdominal cavity remains insufflated during this processing and is not decompressed for insertion or manipulation of device 220. FIGS. 18 & 20 show the insertion of a morcellator 110 into device 10 to process tissue 8.

Figure 21:
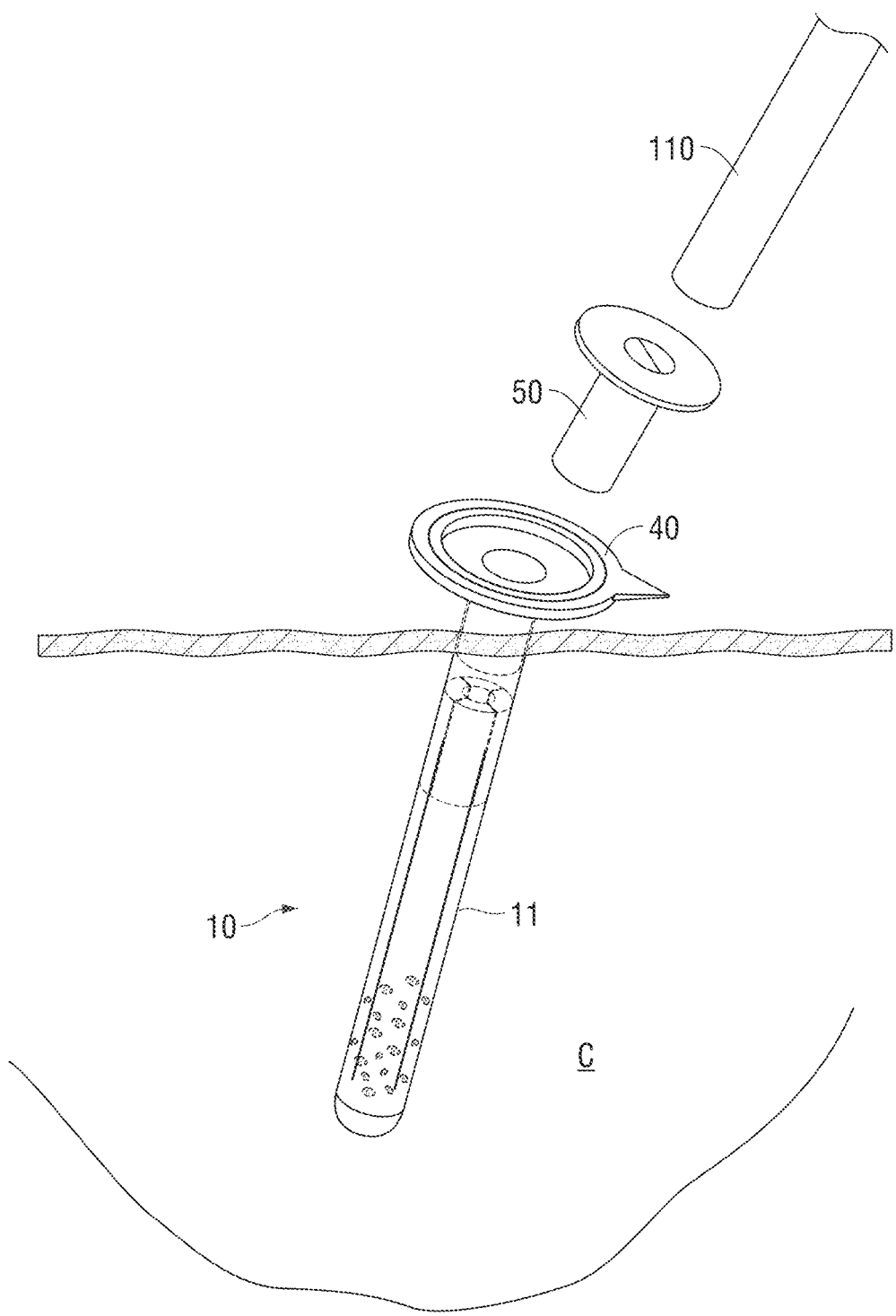
FIG. 21 is perspective view of similar to FIG. 19 showing the morcellator and expander being removed from the device, and the device in the collapsed position.

At 318 workspace device 220 is removed from the body with the processed tissue. In some embodiments, the macerated tissue is removed first. FIG. 21 shows a collapsed workspace device 10 with morcellated tissue therein during removal thereof.

At 320, the procedure may continue (e.g., suturing, implanting).

Exemplary Usage of a Workspace Device

Figure 4A:
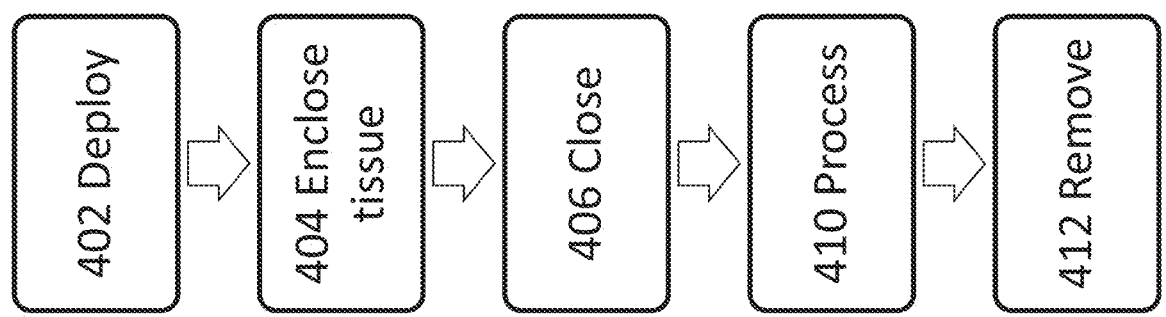
FIG. 4A is a top-level flowchart of a method of using a workspace device during a laparoscopic procedure, in accordance with some exemplary embodiments of the invention.
Figure 4B:
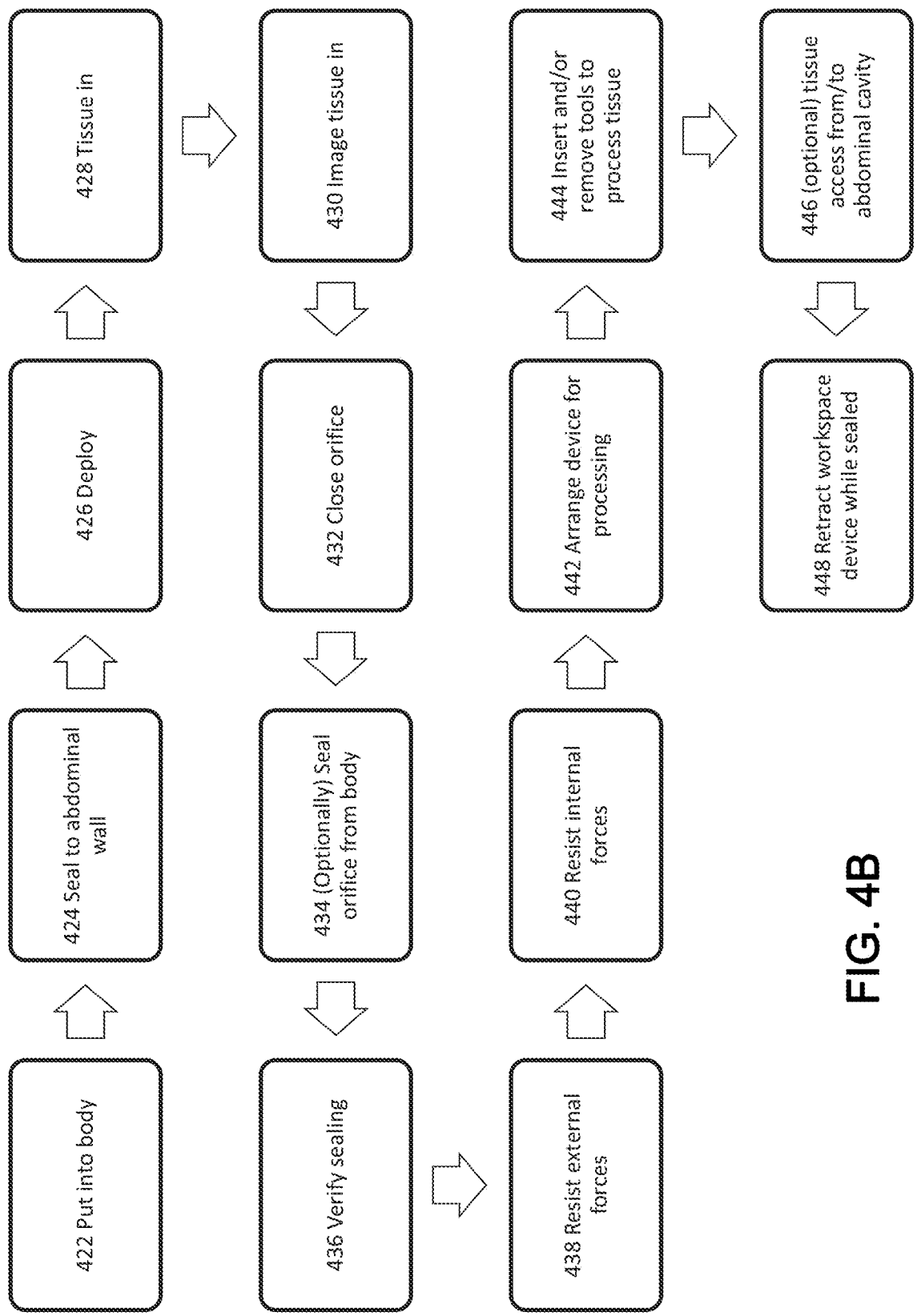
FIG. 4B is a detailed flowchart of a method of using a workspace device during a laparoscopic procedure, in accordance with some exemplary embodiments of the invention.

FIG. 4A is a top-level flowchart of a method of using a workspace device during a laparoscopic procedure, in accordance with some exemplary embodiments of the invention. FIG. 4B is a detailed flowchart of a method of using a workspace device during a laparoscopic procedure, in accordance with some exemplary embodiments of the invention. Referring first to FIG. 4A.

At 402, workspace device 220 is deployed, for example as will be detailed below;

At 404, tissue, for example, an organ or other tissue makes its way into working volume 234 of workspace device 200.

At 406, an orifice through which tissue entered volume 234 is closed.

At 410, the enclosed tissue is processed.

At 412 workspace 220 is removed from the body.

Referring now to FIG. 4B.

Figure 5:
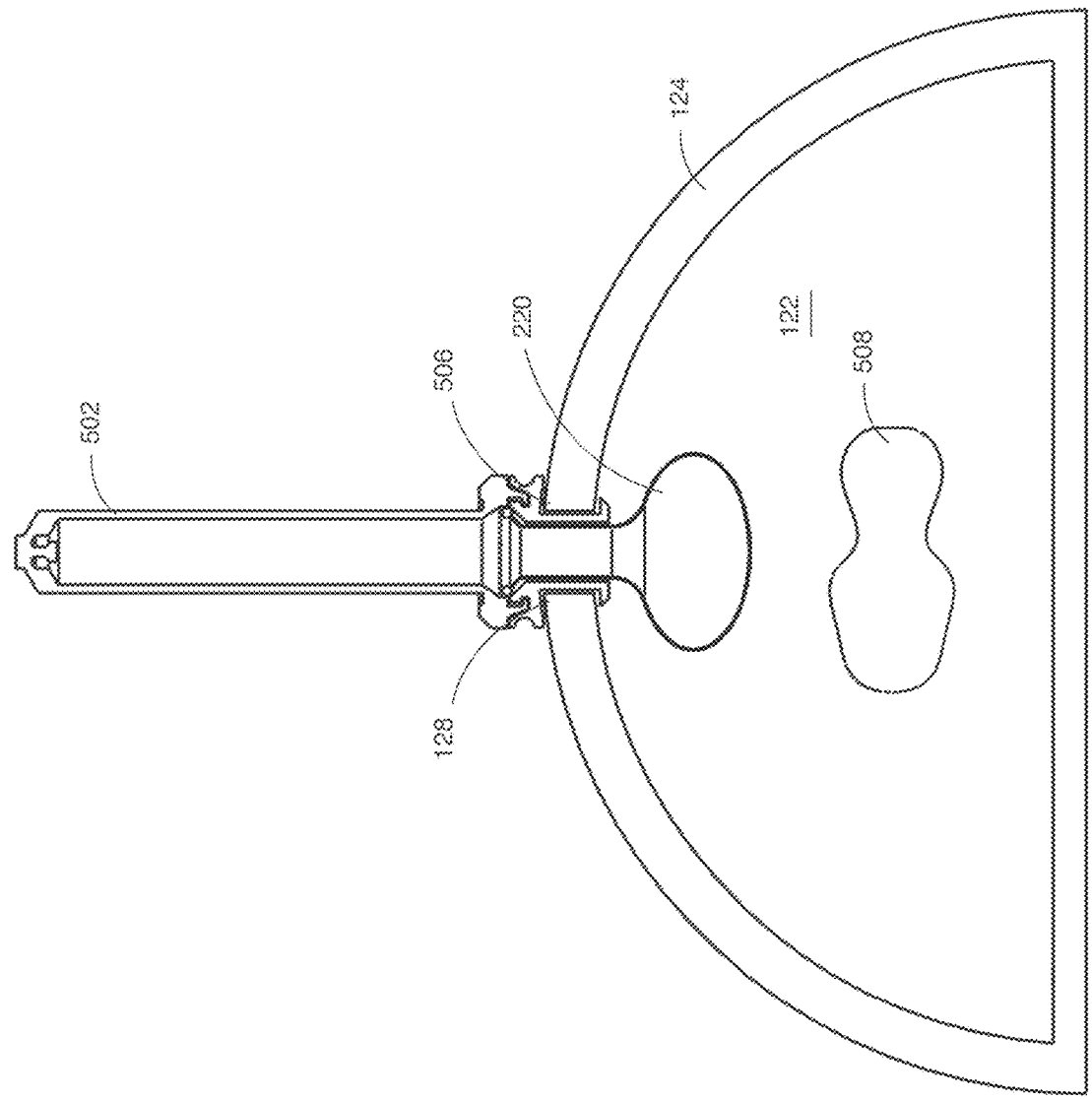
FIG. 5 is a schematic showing of the insertion of a workspace device into an abdominal cavity, in accordance with some exemplary embodiments of the invention.

At 422, device 220 is inserted into the body. FIG. 5 is a schematic showing of the insertion of workspace device 220 into abdominal cavity 122, in accordance with some exemplary embodiments of the invention. Tissue to be processed 508 is shown as being free in cavity 122, though it may be attached to tissue and/or may be held by a tool, such as a gripper (not shown). In the example shown, device 220 is mounted in a delivery system 502, for example, a plunger, which attaches to a port 506 or, alternatively is fit into opening 128 in abdominal wall 124. In some exemplary embodiments of the invention, delivery system 502 includes a dedicated insertion port (e.g., 506), which optionally detaches from device 502 after device 220 is inserted into abdominal cavity 122.

In some embodiments of the invention, opening 128 is a dedicated opening. Alternatively, it is an opening previously or later used for a different laparoscopic tool. Optionally, the opening is expanded if device 220 needs a larger opening than the tool. Optionally, the opening is in the umbilical region or from a side of the abdomen.

At 424, device 220 is sealed to opening 128. This may be needed, if device 220 does not include its own frame 242 for opening 128. It is noted that in some embodiments, parts of membrane 232 are pulled out of the body, while a frame portion of device 220, if any, and/or rigid portion 242, if any, may remain within. In some exemplary embodiments of the invention, device 220 is inserted through a laparoscopic port, which may include a seal. The term "laparoscopic channel" is used to generally describe any type of opening in the abdominal wall, through which device 220 may be inserted, for example, an incision, a wound, a cut and/or optionally including a separate port device. "Tool channel" relates to a part of the workspace device (e.g., device 220) through which a tool can be inserted into volume 234.

At 426, device 220 is deployed, e.g., made ready to receive tissue thereinto. It is noted that deployment may be delayed if workspace device 220 is not needed yet. Optionally, the orifice is oversized for the tissue to be received. For example, if a tissue is to be received, that tissue, when best oriented, has a maximal cross-sectional area which is desirably smaller than the cross-sectional area of the orifice. This is termed the tissue "minimal" cross-sectional area and is the smallest "maximal" cross-sectional area thereof. Optionally, there is a factor of at least 1.1, 2, 2.5, 4 or intermediate or greater factors, to assist in insertion. Optionally or alternatively, to defining by area, the orifice has a shape which is larger by at least 10%, at least 20%, at least 50%, or intermediate or more in all directions than a geometric projection of the tissue for which it is intended on a plane.

Figure 4C:
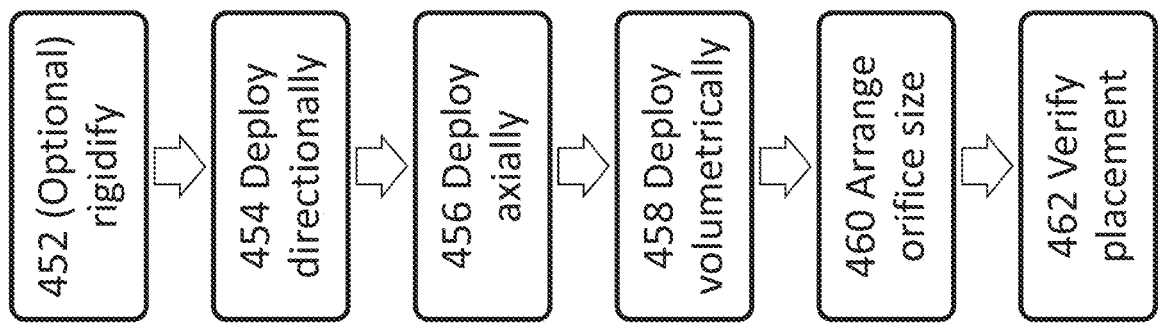
FIG. 4C is a detailed flowchart of a method of deploying a workspace device during a laparoscopic procedure, in accordance with some exemplary embodiments of the invention.

FIG. 4C is a detailed flowchart of a method of deploying a workspace device during a laparoscopic procedure, in accordance with some exemplary embodiments of the invention;

After insertion into the body (FIG. 5), the device is optionally rigidified, for example, by insertion of one or more rigid elements thereinto or by inflation thereof. Rigidization can also be carried out later in deployment. In some embodiments of the invention, rigidization comprises inflating one or more inflatable chamber therein. In some embodiments of the invention, rigidization comprises releasing the device to self-expand, for example, by retracting a sheath or an internal mandrel which holds the device in a closed condition. In some embodiments of the invention, rigidization comprises interlocking one or more rigid components. It is noted that in some embodiments the device already includes one or more rigid elements, but the device is not in a rigid deployed configuration. Expanding the device can accomplish this, for example, using one of the methods described herein. Rigidity of the device is optionally provided by a mechanical interaction between tensile properties of the thin membrane (232) and the rigidity of one or more rigid elements. The rigid elements are also termed herein "rigid struts". In a particular embodiment of the invention, the rigid struts are formed of plastic and are pre-deformed to expand device 220 by bending and stretching a thin membrane therebetween. In some embodiments of the invention, pre-deformation is provided using a spring or by positioning magnets with like poles that repel each other, the repelling occurring when a limiting force (e.g., a sheath) is removed.

In another particular embodiment of the invention, wall 232 is doubled layer (e.g., see FIGS. 8A-E below) and includes one or more inflatable chambers defined between the walls, so that inflation thereof causes the chambers to act as rigid struts.

In some embodiments of the invention, insertion and inflation are by a single step. For example, delivery system 502 may use air (or liquid) pressure to both advance device 220 and inflate it.

In another embodiment, the rigid elements extend out of the body and can each pivot about a point near or at opening 128 (e.g., may lie in channels or be attached to device 220 at or about opening 128). This allows the device to be laterally expanded by manipulating of the ends that are outside the body.

In some embodiments of the invention, deployment is by active mechanical manipulation, for example, (e.g., see FIG. 22A-22C) changing the relative position of two components of the device, for example, by rotation or a threaded element, insertion of an element or pulling of an element (e.g., a string 205 (FIG. 2) attached to a far side of device 220 or rigidifying element thereof, optionally manually activated).

In some embodiments of the invention, deployment is by insertion of elements and/or in stages. For example, an elongated element may be inserted into workspace device 220 to axially deploy device 220 and an inflatable element may be inserted to volumetrically deploy device 220 (or the same deployment element may be inflated or expanded). Optionally, the rigid struts of device 220 in such an embodiment are plastically deformable to maintain the shape after such inflation, or may mechanically interlock to maintain the shape.

At 454 device 220 is deployed directionally, such that orifice 230 is pointed in a direction from which tissue is to be provided into orifice 230. Optionally, the device is inserted in a directional manner. For example, a directional indicator, for example, 43, 43a (FIG. 11), may be used, which is visible outside the body. Optionally or additionally, frame 242 is rotated, rotating device 220 with it. Optionally, this is done under visualization, for example, using a previously intra-abdominally inserted imager. It is noted that some embodiments feature a workspace device which is thin walled and not amenable to manipulation. Optionally, this is avoided or reduced by inserting in a correct direction (e.g., and using a device with a laterally directed orifice 230) and/or by manipulating frame 242, rather than wall 232. Optionally, one or more gripping points 231, including stronger and/or stiffer material, are provided on wall 232, to enable gripping of those points and manipulating wall 232 thereby, without damaging the integrity of wall 232.

A potential advantage of some embodiments of the invention is prevention of damage to intra-abdominal organs during insertion and deployment. Optionally, this is facilitated by correct selection of device 200 and by insertion of rigid elements and/or expansion only after correct placement relative to intra-abdominal organs is noted.

At 456, device 220 is optionally deployed axially. In some embodiments of the invention, the size of volume 234 is determined, at least in part, by axial advance of wall 232 relative to frame 242 and/or opening 128. Optionally, advance is controlled by using an inner mandrel and/or by selecting rigidifying elements for insertion or inflation of a desired length and/or geometry (e.g., curvature).

At 458, device 458 is optionally deployed volumetrically, e.g., expanded to define a desired size and shape of workspace volume 234. Optionally, this is done by selective inflation or selective use of rigidifying elements. Optionally or additionally, this is done by selectively shortening one or more internal chords of device 220, for example, by pulling on one or more tensile elements 205 which interconnect a rigidifying element 218 or 222 to tube 246 or frame 242, thereby shortening the chord. Optionally, element 205 (for example a wire) includes one or more widened sections along its length which can lock into a notch formed in frame 242. Other interlocking mechanism can be used as well. Optionally or alternatively, element 205 lies (and slides) within a rigidifying element. Optionally or alternatively, element 205 is used for changing the shape of device 220, for example, after orifice closure. If multiple elements 205 are provided, then selective shortening of such elements can be used to provide asymmetric control of the shape of device 220.

FIG. 10D is a side view of a workspace device 1060 using tensile members 1066 optional within rigidifying members 1064 for controlling a geometry of a wall 1062 of device 1060, in accordance with some exemplary embodiments of the invention. Optionally, a plurality of members 1066 extend out of the body and may be, for example, individually and/or manually shortened to control said geometry. Optionally, as shown, members 1066 do not extend to a bottom of device 1060. Different members may extend different vertical amounts. Optionally, members 1066 are fixedly coupled to rigidifying members 1064 at ends of members 1066. Optionally, a lock, not shown, is used for fixing the relative lengths of members 1066. For example, a plurality of channels for members 1066 may be formed in a ring and a conical plug inserted into or retracted form the ring to lock the members in place. In another example, the members are attached to one or more rigid members which are lockable in place relative to a rigid portion of device 1060, extending out of the body.

In some embodiments of the invention, the volume of device 220 is selected according to need and this may set the shape and/or location of the deployment. This type of selection can be useful for tissue which is separated, because it may be easier to move the tissue than find an alternative location for device 220.

At 460, the geometry of orifice 230 is optionally arranged, for example, its shape and/or size. In one example, a normally closed orifice is opened. In another example, lips 202 are manipulated to partially close the orifice and/or change its shape. In another example, lips 202 close (or open) by inflation, and partial inflation is applied to shape them. Optionally or alternatively, orifice 230 is normally open.

At 462, correct placement of device 220 is optionally verified, for example, using an intra-abdominal imager and/or by imaging through device 220 from inside.

With regard to deployment it is noted that in some embodiments of the invention, contact with intra-abdominal tissue and organs is avoided. Optionally, deployment is manual, allowing potential such contact to be monitored during deployment. Optionally or additionally, some arts of deployment are automatic (self-deployment) and correct selection of device 220 may be used to avoid undesired contact. This may be in contrast to some existing retrieval bags, where the bag lies on intra-abdominal organs. In some embodiments of the invention, device 220 hangs from abdominal wall 124 and may be therefore suspended in space.

It is noted that contact, especially forceful contact, during usage are optionally avoided.

Referring back to FIG. 4B.

At 428, tissue to be process 508 is optionally inserted into workspace volume 234 via orifice 230. In some embodiments of the invention, such insertion is by grapping tissue 508 and pushing it into volume 234. Optionally, device 220 is stiff enough to avoid bending away if/when tissue 508 contacts wall 232 rather than pass smoothly through orifice 230.

In some embodiments of the invention, a tissue engaging tool, such as a grasper is inserted through tube 246 and out of orifice 230 to grab the tissue and pull the tissue into orifice 230.

In some embodiments of the invention, a grasper (e.g., laparoscopic inserted through a separate laparoscopic port and/or valved entry 248) is used to hold lips 202 of orifice 230 steady during such manipulations.

At 430, the correct placement of tissue 508 is optionally imaged, for example, using an intra-abdominal imager, and/or via an imager inserted through opening 128. In embodiments where wall 232 is transparent or includes one or more transparent areas, imaging may be through wall 232.

At 432 orifice 230 is closed and at 434, the orifice is optionally sealed and/or otherwise isolated from the intra-abdominal cavity. It is noted that in some embodiments, closing and sealing are two different acts. Sealing may allow the creation of a negative pressure differential between workspace volume 234 and intra-abdominal cavity 122.

Figure 19:
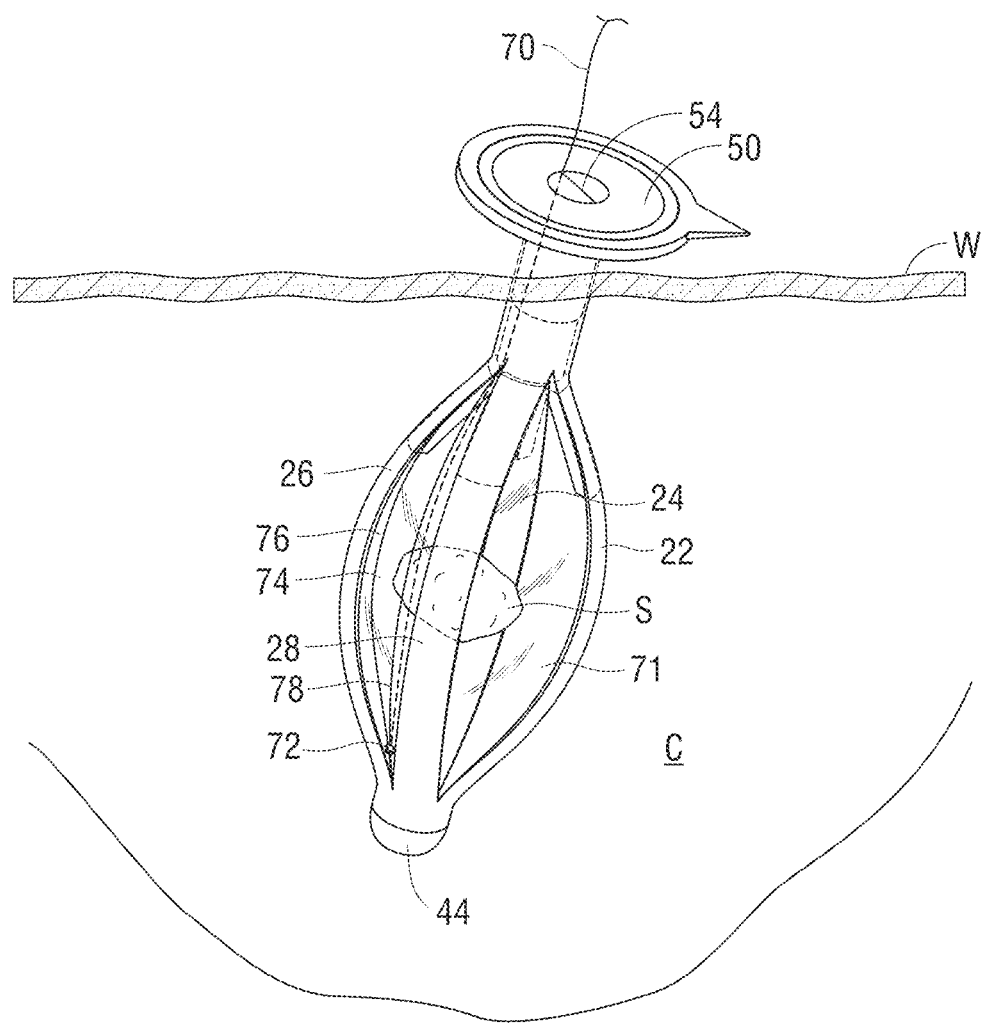
FIG. 19 is a perspective view of an alternate embodiment of the device having a string actuable for sealing the device.

As noted, in some embodiments of the invention orifice 230 is normally closed, so it can be released to close. In others, it may be normally open or neutral and be closed, optionally manually. It is noted that direct manual manipulation may not be easy. FIG. 18 shows an example of manual manipulation of a zipper 68 using a laparoscopic grasper 100. FIG. 19 shows an example of manual manipulation of a zipper using a drawstring 70. In some embodiments of the invention, such manipulations form outside the body are replaced by allowing a manipulation inside the body, for example, drawstring 70 or 204 may be used to activate a closing mechanism which brings lips 202 towards each other. In some embodiments of the invention, a grasper inserted through opening 248 or opening 244 is used to manipulate lips 202 to close orifice 230.

FIG. 10B shows an exemplary sliding closure.

In another example, deflation of inflatable chambers in lips 202 allows a pre-deformed element (or a magnetic seal) in lips 202 to assert itself, as it does not need to work against these chambers, and close orifice 230.

An example of a normally closed orifice is a valve, for example a one way valve (e.g., formed and/or supported by lips 202, for example, a flap valve or a duck valve or other type of vale optionally using flexible leaflets), which closes once all of tissue 508 passes therethrough. A tool may be needed to clean lips 202 so that they close against each other. In some embodiments, lips 202 seal to tissue (not tissue 508) rather than to each other. For example, if a cyst is to be drained, tissue 508 (the cyst) may be brought into volume 234 and lips 202 closed on tissue attached to the cyst. The point of drainage of the cyst is thus isolated from abdominal cavity 122 and may be more safely drained, for example, by lancing and suction. In some embodiments of the invention, lips 202 include a plurality of apertures and are attached to a source of suction (e.g., 204 being a tube connecting to suction source 210), so that lips 202 can attach and seal to tissue using suction forces. Optionally or additionally, lips 202 include a soft layer to provide compliance to contacted tissue geometry. In some exemplary embodiments of the invention, suction apertures along one or more lips 202 are used to seal lips 202 to each other and/or other parts of wall 232.

In some embodiments of the invention, orifice 230 is closed by covering with a flap, for example, folding a flap over the orifice. This is shown, for example, in FIG. 8B.

Figure 7A:
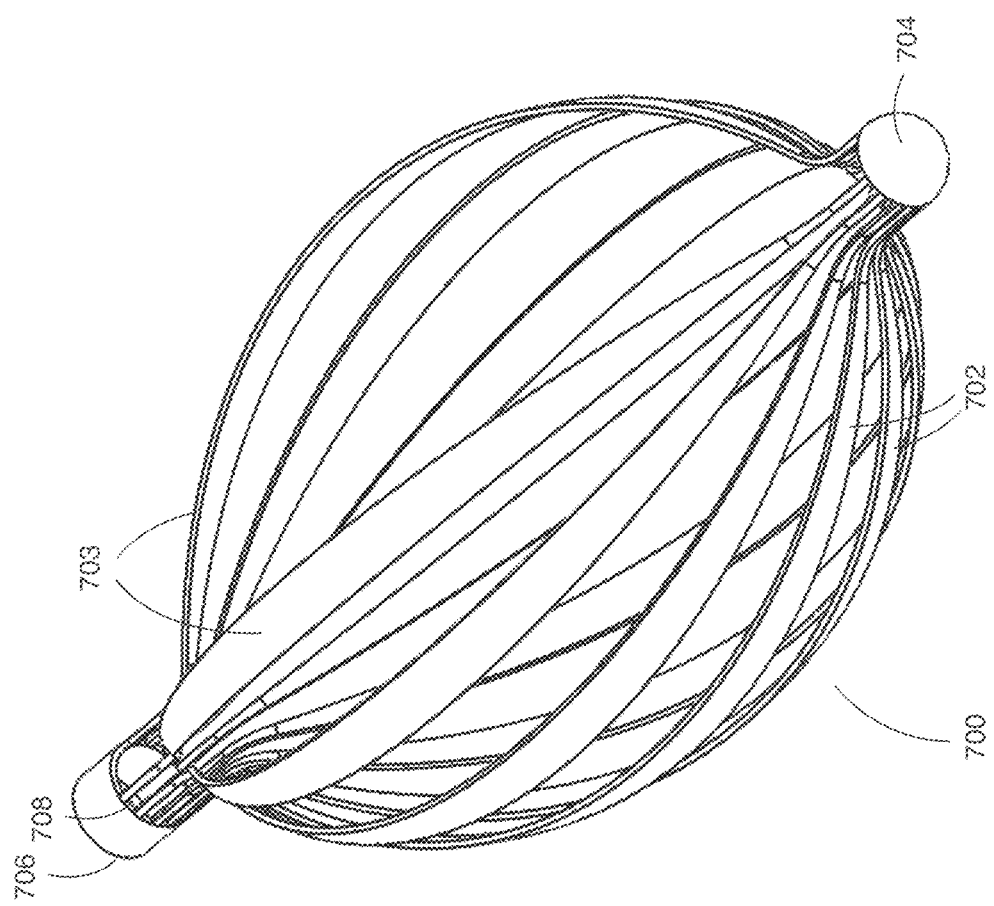
FIGS. 7A and 7B are schematic showings of the arrangement of ribs in a workspace device with permanent rigidifying elements, in accordance with some exemplary embodiments of the invention.
Figure 7B:
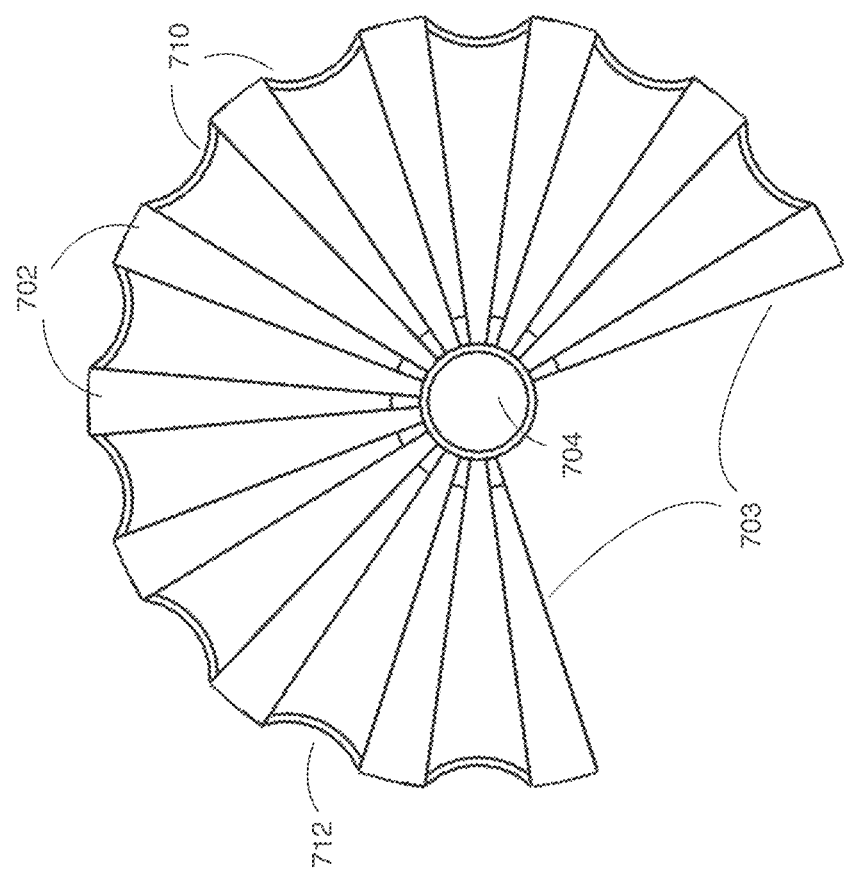
Figure 7C:
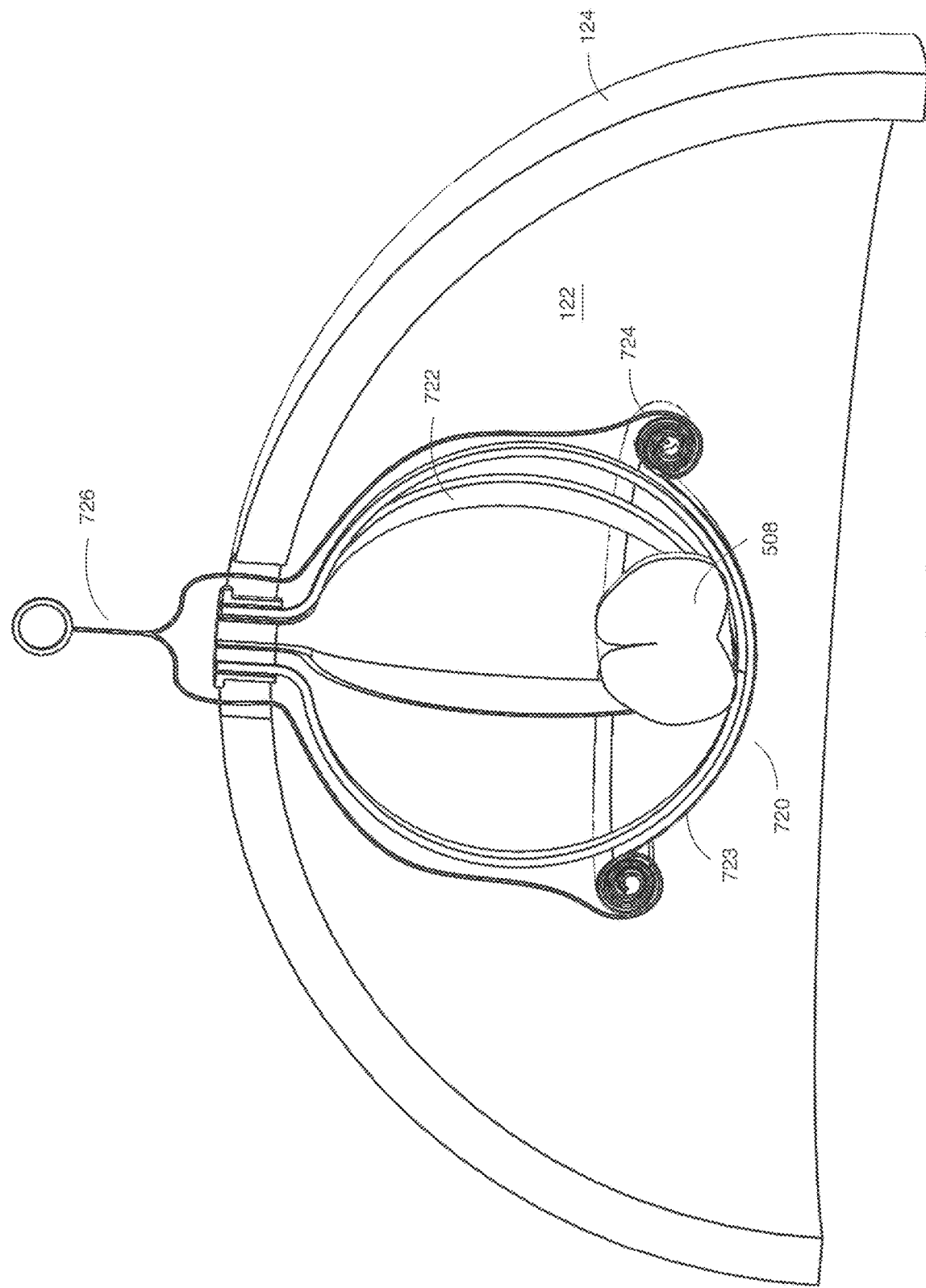
FIG. 7C is a schematic showing of a workspace device with permanent rigidifying elements and a movable membrane, in accordance with some exemplary embodiments of the invention.

In some embodiments of the invention, orifice 230 is closed by rolling up a sleeve, for example, as shown in FIG. 7C.

In some embodiments of the invention, a purse-string suture is provided in lips 202 and pulling on drawstring 204 or releasing the suture (or other self-contracting element in lips 202) to contract (if it is a self-contracting suture) closes orifice 230.

In some exemplary embodiments of the invention, closing is by advancing a suture over a drawstring to over an extension of the orifice lips (e.g., the sleeve).

In some embodiments of the invention, sealing (and optionally closing) includes applying adhesive or heating (e.g., using a grasper with a heating element) to weld together lips 202. (e.g., FIG. 10C).

In some embodiments of the invention, closing is by twisting lips 202, for example, if they extend in the form of a sleeve. Optionally or additionally, such lips may be brought into an apertured closure element and held therein by friction, optionally due to radial contraction of the element. (e.g., FIG. 9M).

In some embodiments of the invention, lips 202 overlap with each other in a circumferential direction, to provide closure. In one example, one of lips 202 is pre-disposed or otherwise has a stable state when it overlaps the other lip. For example, both the lips may be predisposed to extend convexly towards orifice 230, rather than concavely when the orifice is open, as shown. In another example, the lips extend away from device 220 and overlap, meeting to provide closure. Optionally, a drawstring 204 is used to approximate lips 202 and/or release or expose adhesive thereat.

Figure 9A:
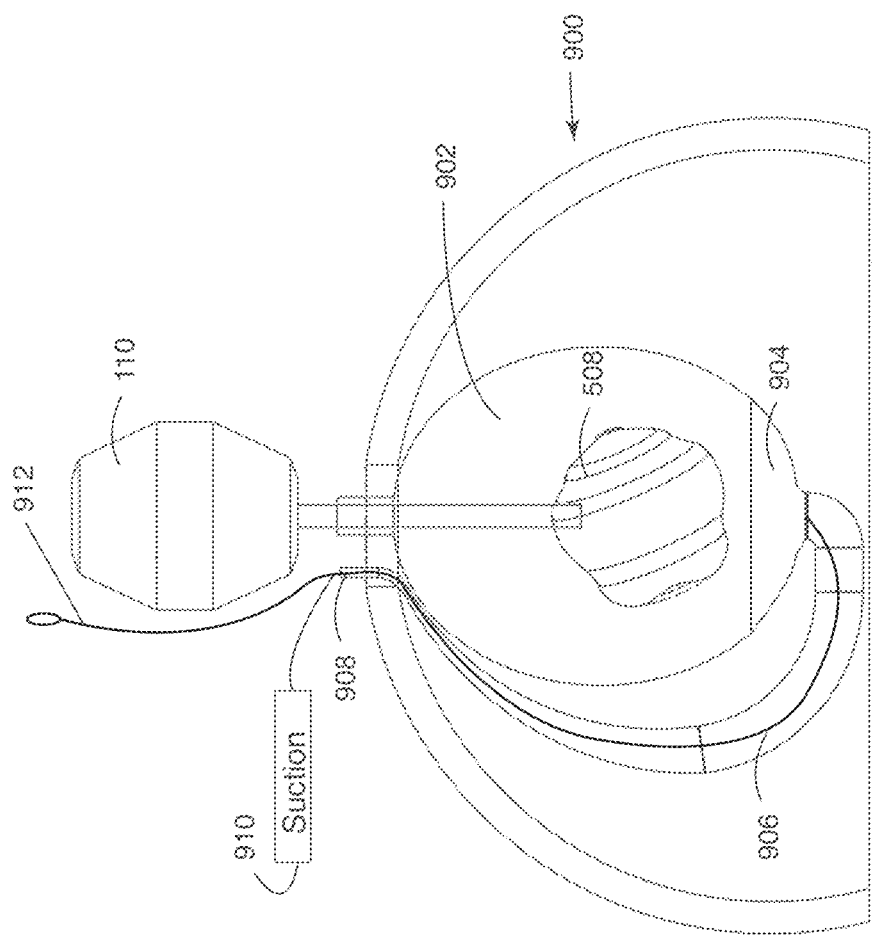
FIG. 9A is a schematic showing of a workspace device with a sleeve extendible out of the body, in accordance with some exemplary embodiments of the invention.

In some embodiments of the invention, closure and/or sealing is by bringing an extension of lips 202 outside of the body, for example, as shown in FIGS. 9A-N.

It is a particular feature of some embodiments of the invention that closing orifice 230 does not require tissue 508 to be moved (e.g., more than 4, 3, 2, 1 cm in any direction or smaller or intermediate amounts). This is in contrast to bags where the edges of the opening used to insert the tissue are then pulled out of the body, where the tissue will be jostled and moved, possibly falling out of the bag.

At 436, the quality of the sealing is optionally verified. In one example, verification is by filing workspace volume 234 with a fluid and seeing if any leaks into the abdominal cavity. In another example, verification is visual. In another example, de-pressuring workspace device 220 should cause some change in shape due to the larger intra-abdominal pressure and due to the flexibility of some parts of wall 232 (if any). This may be visually noted. Optionally or additionally, wall 232 includes a dedicated chamber or section which deforms due to the pressure difference, giving a visual indication that there is a seal. As an example, a small flexible wall section with a dome shape is expected to change its shape according to pressure differences thereon. Optionally, a tube extends from said dedicated chamber to outside the body to provide an indication of pressure, outside the body.

At 438 device 220 is already set up for resisting external forces, such as said pressure differential and/or contact by tools and/or tissue in the abdominal cavity. Such resistance is optionally ongoing to prevent leakage of contents of workspace volume 234 into intra-abdominal cavity 122.

As noted above, in some embodiments of the invention intra-abdominal pressure is not reduced and device 220 may be suspended from abdominal wall 124 so as to avoid contacting intra-abdominal organs or other tissue.

At 440 device 220 is already set up for resisting internal forces, such as may be applied by tools moving and/or operating in volume 234. Such resistance is optionally ongoing to prevent leakage of contents of workspace volume 234 into intra-abdominal cavity 122. In one example, vacuum is applied in volume 234. However, as wall 234 includes rigidifying elements, this optionally does not cause collapse (e.g., reduction in volume by 205, 30%, 40% or intermediate or greater amounts) and/or local collapse of wall 232, thereby avoiding damage to tissue outside wall 232.

At 442 workspace 220 is set up for tissue processing, for example, by changing a shape thereof, moving away from sensitive tissue (e.g., avoid keeping the aorta in a direct line of operation of tools) and/or changing orientation relative to gravity. Optionally, such changes are by manipulating frame 242 and/or pulling on wires 205 and/or inserting or removing rigidifiers and/or changing inflation pressures. In some exemplary embodiments of the invention, preparation comprises inserting a shield into volume 234, for example, to prevent accidental damaging of the wall and/or opening of orifice 230 by contact with a tool and/or other tissue processing activities. For example, the shield may be a self-expanding disc mounted on an arm, and held in place so the disc is between a sharp tool and wall 232.

At 444, tissue 508 is optionally processed, for example, by providing tools thereinto. For example, a lance may be used to lance a cyst; a morcellator may be used to reduce tissue dimension; a grasper or other tissue manipulator may be used to manipulate tissue and/or hold it in place for other tools; a transfection tool may be used to genetically alter tissue; a medicament applicator (e.g., by spray, needle injection and/or spreading) may be used to apply a pharmaceutical to tissue; an implant delivery tool may be used to deliver an implant such as an anastomosis device or a clip; a suturing tool may be used to suture tissue; an electro-ablation or electro-cutting tool may be used to heat tissue; a welder maybe used to weld tissue and/or blood vessels in a tissue; a therapy tool may be introduced to apply therapy, such as light therapy, to tissue; a suction tool may be used to extract fluid and/or small particles, an ablator may be used to ablate tissue and/or a cutter may be used to cut part of tissue.

It is noted that because treatment is inside workspace device 220, side effects, such as contaminating or inadvertently affecting other intra-abdominal tissue, may be reduced or avoided.

In some embodiments of the invention, the tool used is a morcellator, optionally a standard morcellator (e.g., which is sized to fit through tube 246). Optionally, rigidified wall 232 allows the use of a wider range of morcellators without worrying about inadvertently damaging intra-abdominal tissues.

At 446, access to intra-abdominal cavity is provided 122. This may be useful if a tool is inserted into device 220 from cavity 122. Optionally or additionally, this is used when intentionally releasing treated tissue (e.g., a treated tissue graft) from volume 234 back into cavity 122, for example, for implantation thereof. Optionally, such exchange is by reopening orifice 230 (e.g., deflating an inflatable orifice, unzipping a zipped orifice). Optionally, orifice 232 may be reclosed and/or resealed thereafter, one or more times.

At 448, device 220 is removed and if inserted through a port, the port is optionally reusable. In some embodiments of the invention, device 448 is integral with a port (e.g., frame 242 forming part of the port or attached thereto). Optionally, neck 246 can be separated from frame 242 (and valve 244 is optionally directly mounted on frame 242, as may be in other embodiments as well), leaving frame 242 to act as a laparoscopy port. Optionally, separation is by a tear string tearing a tear line in neck 246, which tear line lies, for example, outside of the body.

In some embodiments of the invention, it is important to maintain device 220 in a sealed configuration during removal. Optionally, volume 234 is optionally emptied first, for example, by suction. Following that, the workspace volume 234 is optionally collapsed. FIG. 21 shows an example of reducing the dimension of workspace device 10 by removing a workspace expanding insert 50.

In some embodiments of the invention, closure mechanism found in lips 202 is configured to not catch on frame 242 (if existing) and/or on intra-abdominal tissue and/or on a laparoscopy port during removal. Optionally, for example, if a zipper is used, the zipper or other sealing element seals when moved away from the abdominal wall, so if such catching occurs, it will not unseal device 220.

Exemplary Materials and Other Properties of Workspace Device

In some embodiments of the invention, wall 232 is formed of a membrane, for example, formed of a polymer, for example, polyurethane or other hydrocarbon, or a silicon-based polymer, for example, between 10 and 1000 microns thick, for example, between 20 and 400, for example, between 50 and 100 microns thick. Optionally, the wall is composed of two or more layers of such thickness. While in some embodiments wall 232 is gas impermeable, in some embodiments, wall 232 is gas permeable, for example, being formed of a woven fabric or apertured sheet. This may allow a less stiff and/or strong structure to be used, as resistance to intra-abdominal pressure differential will not be needed. Optionally, the wall is impermeable to cells, for example, passing only material smaller than 10 microns, 5 microns, 1 microns, 0.5 microns, 0.01 microns or intermediate or smaller, in their smallest dimension.

In some embodiments of the invention, device 220 includes one or more rigidifying elements (e.g., 218, 222). Optionally, they are all formed of a same material. Alternative, different ones are of different materials. In some embodiments of the invention, the material is shape memory and/or super elastic, for example, being formed of nitinol or a suitable polymer, for example, a silicon or hydrocarbon polymer. Optionally or additionally, the material is metal, for example stainless steel. In some exemplary embodiments of the invention, an element has a maximal cross-sectional diameter over most of its length of between 0.1 and 4 mm, for example, between 0.3 and 2 mm, for example, between 0.5 and 1.2 mm.

In some embodiments of the invention, channels in or on wall 232 are welded on patches or welds between two layers of wall 232. Optionally or additionally, such channels are formed by attaching a ready-made channel (or chamber) to wall 232.

In some embodiments of the invention, rigidifying elements are embedded in wall 232. Optionally or additionally, at least one such element is adhered to the inside, outside and/or between layers of, wall 232.

In some embodiments of the invention, the rigidifying elements are elastic, in that if deformed, they return to a desired resting state. This may assist in resisting the effect of momentary high forces, such as due to inadvertent tool contact with wall 232. It is noted that in other embodiments, workspace device 220 is plastically deformed, for example, using plastically deforming rigidifying elements. In some embodiments of the invention, this means that the elements can be plastically deformed without requiring a degree of deformation which would tear wall 232.

It is noted that the term "rigid" as used herein is relative and relates to the ability of the device and/or element to withstand deformation by expected forces after deployment, for example, due to pressure differentials, manipulation of tissue inside device 220 and/or contact with tools and/or abdominal tissue. For example, a thin nitinol wire may be sufficient to maintain the shape of device 220, but might be bendable by hand. Optionally, device 220 can resist collapse under a pressure difference of 15, 20, 25 or intermediate or greater pressures mmHg.

In some embodiments of the invention, while rigid, device 220 avoids parts with a high curvature, such as finger-like projections, which could apply undesired trauma to intra-abdominal tissue. For example, no intra-abdominal part with a radius of curvature smaller than 10 mm extends more than 4 mm from a general surface of device 220, unless it is soft enough to not cause trauma. In some embodiments, this property is true also during insertion (e.g., according to FIG. 5 example, where insertion is of a soft leading part, optionally using air pressure).

In some exemplary embodiments of the invention, the cross-section of the orifice is circular, ellipsoid and/or rectangular. In some exemplary embodiments of the invention, the cross-section of the device is circular, ellipsoid and/or rectangular. Other cross-sectional shaped may be used, for example, to fit a tissue and/or operation location. Furthermore, the device may have a non-uniform cross-section.

In some embodiments of the invention, the shape of device 220 is generally egg shaped, with the narrow dimension horizontal. Other shapes may be provided as well, for example, spherical, horn shaped and tubular. Optionally, the length of the device is between 0.75 and 3 times the maximum width of the device. In some exemplary embodiments of the invention, orifice diameter is between 10 and 110 mm, for example, between 20 and 70 mm, for example, between 30 and 50 mm or intermediate sizes. In some exemplary embodiments of the invention, optionally, device 220 is rotationally symmetric around a long axis thereof. In some embodiments, the axis bends, for example, in a horn-shaped device. A potential advantage of such shape is that even though insertion is at an umbilical area (or other convenient location), the tissue can be placed where convenient (e.g., side opening) and/or processed at a place and direction so the aorta is not along a direct line connecting opening 128 and the tissue. In some embodiments of the invention, other shapes are used, for example, to better match the shape of the expected available volume in intra-abdominal cavity 122. It is noted that the location of orifice 232 may also be selected according to need and be, for example, at a lateral side or at a distal side of device 220. Optionally, orifice 232 is round or ellipsoid, though other shapes may be provided as well. In some embodiments of the invention, orifice 232 extends between 20% and 80% of a projected length of the wall of device 220 on which it is found, such that there is wall material surrounding the orifice, for example, to an extent of between 10% and 30% of a diameter of the orifice.

In some embodiments of the invention, the intra-abdominal portion of device 220 is between 10 and 200 mm in length, for example, between 30 and 150 mm in length, for example, between 40 and 110 mm in length.

In some embodiments of the invention, device 220, when deployed, is between 10 and 200 mm in width, for example, between 30 and 150 mm in width, for example, between 40 and 110 mm in width.

In some embodiments of the invention, frame 242 is between 2 and 20 mm in outer diameter where entering abdominal wall 124, for example, between 3 and 15 mm. Optionally, the inner diameter (e.g., of tube 246) is between 0.5 and 3 mm smaller than the outer diameter. In some embodiments of the invention, when not deployed device 220 (other than any part intended to not pass through abdominal wall 124 is between 1 and 30 mm in maximal cross-sectional extent, for example, between 2 and 20 mm, for example, between 4 and 15 mm.

In some embodiments of the invention, when deployed, the width of device 220 expands by a factor of between 1.1 and 40, for example, between 3 and 20, for example, between 5 and 10. Optionally, the expending part extends past any outside rigid portions such as frame 242. In some embodiments of the invention, the volume of volume 234 is between 10 and 2000 cc, for example, between 50 and 1500 cc, for example, between 500 or 700 and 1000 cc.

For applications other than the abdominal cavity, other sized may be used, for example, insertion diameter of between 1 and 10 or 20 mm, and/or bag volume of between 1 and 100 cc.

Exemplary Use of Negative Pressure Difference

FIG. 6 is a schematic showing of the effect of negative pressure difference, on leakage, in accordance with some exemplary embodiments of the invention. In some embodiments of the invention, a pressure differential is maintained across wall 232 between intra-abdominal cavity 122 and workspace volume 234. In some embodiments of the invention, this is used to prevent or reduce leakage of material from volume 234 to cavity 122, due, for example, to damage or imperfect manufacture or sealing.

FIG. 6 shows an example where a tear 602 is formed in wall 232 (but it could also be an imperfect seal at orifice 230). Due to the pressure differences, fluid will tend to flow according to arrows 604 from intra-abdominal cavity 122 into workspace volume 234, and tissue 508 (shows as a sliver through opening 230 left a little open for exposition purposes) inside workspace volume 234 will not leak out. Excess pressure may bleed out of opening 126 to the operating room, if opening 126 is not sealed. Optionally, device 220 includes a sealed chamber at atmospheric (or other pressure lower than intra-abdominal pressure), which chamber can provide compliance, by collapsing if there is inflow through tear 602. Optionally, such a chamber (e.g., in the form of chamber 228) is vented to outside the body.

In some embodiments, no pressure differential is provided, rather a pressure equilibrium is provided. This will still avoid tissue flow out of volume 234 which would otherwise be due to excess pressure inside volume 234.

In some embodiments, volume 234 does have a higher pressure than cavity 122 and the above described mechanism is not available. Optionally, a valve 233 (FIG. 2) is provided to allow pressure differences to bleed through, so as to equalize pressure inside and outside of workspace device 220, without allowing passage of tissue therethrough. Optionally, valve 233 includes a filter (e.g., of tight mesh) to block cellular matter.

In some exemplary embodiments of the invention, volume 234 is inflated to have a pressure above ambient, but below intra-abdominal levels.

Exemplary Safety Features

Referring back to FIG. 2, device 200 can include one or more safety features, for example:

(a) a protective mesh 224, optionally spaced form wall 232 or a thickening 206 of wall 232 opposite opening 226 and/or at other locations where axial advance or other strong motions of an inserted tool are expected, for example, opposite orifice 232;

(b) rigidity defining a concave shape at a top side of device 220 and/or at other parts of wall 232, to prevent suction of wall 232 into a morcellizer tool;

(c) small enough distance between rigid elements to prevent parts of wall 232 from fitting into a tool such as a morcellizer and reaching a blade thereof;

(d) ongoing removal of blood, smoke and/or other debris from volume 234, for example, using suction 208, optionally from a bottom (gravitational) of volume 234;

(e) blood or tissue congealing and/or absorbing material 226, to reduce the amount of fluid present to leak out;

(f) the above negative pressure differential to prevent leakage;

(g) suspension of device 220 without leaning against intra-abdominal organs, optionally at a distance of, for example, 1 cm, 2 cm, 3 cm or more or intermediate distances from such organs or tissue;

(h) insertion to a direction (e.g., not of bladder, aorta, GI tract) and depth where there is no tissue to be damaged, which is made possible, in part, due to the maintaining of insufflation of the abdominal cavity during insertion and later manipulation of some embodiments of device 220.

(i) avoidance of sharp and/or hard edges, in some embodiments of the invention, to avoid tissue trauma;

(j) double layer walls (e.g., 206 and/or elsewhere), optionally filled with sponge or air, to avoid passing of forces across wall 232;

(k) optional provision of suction between walls to extract debris, at a breech if one of the walls is breached;

(l) a valve 244 on opening 226 to prevent uncontrolled exposure of the surrounding environment (and physician) to debris; and/or (m) providing a sensor 212 and/or 214 to detect pressure changes in volume 234 and/or strain on or treating of wall 232 and/or proximity of tools (or organs) thereto.

Exemplary Rib Arrangement

In some embodiments of the invention, device 220 has the form of metal ribs with a thin membrane stretched thereon. FIGS. 7A and 7B show one example of such a design, in accordance with an exemplary embodiment of the invention.

As shown, a device 700 includes a plurality of vertical ribs 702 which are optionally connected at a distal end of device 700, for example, at a cap 704 and/or optionally connected at a proximal side, for example at a ring 706 defining an aperture 708. The ribs may instead be continuous. It should be noted that ribs can optionally move towards each other and apart in a circumferential direction. Reference 703 indicates two ribs which are optionally spaced apart to define an orifice therebetween. Optionally, the ribs can move towards each other to close a gap therebetween. In some embodiments, the closure is by a membrane which selectively extends between ribs 703, for example, as described in FIG. 7C and/or in FIGS. 9A-N, or by ribs 703 moving enough to approximate each other.

FIG. 7B is a cross-sectional view of device 700, also showing a membrane 710 mounted on the ribs. Membrane 710 is shown concave, due to the pressure difference between intra-abdominal cavity 122 and the inside of device 700.

A reference 712 indicates an optional location for an orifice. Optionally, this location is a part of membrane 710 that is missing (e.g., a whole segment or part of one). The orifice is optionally closed by bring its two bordering ribs towards each other.

Other rib arrangements are possible, for example, ribs that also bend in a circumferential direction, for example, s-shaped ribs. Optionally or additionally, one or more helical ribs are provided.

Exemplary Roll-Up Device

FIG. 7C shows a device 720, possibly using the design of FIGS. 7A and 7B, in which a membrane 723 is deployed after tissue insertion. In device 720, a frame of ribs 722 is inserted into abdominal cavity 122, exposed at least in part. This means that any space between two ribs can serve as an orifice to provide tissue 508 into device 720. In the embodiment shown, the membrane is rolled up (724) at a bottom of device 720, such that when unrolled up, it will: (1) cover ribs 722; (2) separate tissue 508 from intra-abdominal cavity 122; an d(3), unrolled all the way past abdominal wall 124 or if sealed to a surface inside the abdominal cavity 122, for example at a top part of device 720, will provide sealing.

In some embodiments of the invention, unrolling uses one or more pullers 726, which act as tensile elements, such as straps or wires which are optionally rolled up with membrane 724, such that retraction thereof causes unrolling and vertical movement of rolled up membrane 724. Rather than rolling up, membrane 723 may be collected at 724 in other ways, for example, pleated.

A potential advantage of this design is ease of deployment, as there is no need to orient orifice 230. Another potential advantage is that membrane 724 can be inserted ahead of ribs 722, potentially reducing a cross-sectional diameter needed during insertion.

In some embodiments of the invention, device 720 comprises a frame which is then used with an existing retrieval bag (e.g., flexible membrane with one aperture formed in it), which is engaged by pullers 724. It should be noted that pullers 726 can be used to hold even a standard bag against a frame 722, possibly obviating the need to attach membrane 724 to a bottom of frame 722.

In some embodiments of the invention, frame 722 is open at a bottom thereof. Optionally, in use, membrane 724 is placed in the body and spread out (optionally using a self expanding ring attached thereto and with a diameter optionally similar to that of frame 722, or manually). Tissue 708 is then placed thereon. Then frame 722 is inserted into the abode and placed above tissue 508 and membrane 724.

Pullers 726 are used to pull membrane 724 up and towards frame 722. Once membrane 724 pushes against frame 722, the situation shown in the FIG. 7C is achieved and pulling back further on 726 causes sealing of device 720.

In some exemplary embodiments of the invention, the top of frame 722 includes a mesh or other space filling elements to reduce a distance between elements which support membrane 724 thereat. This may be useful if membrane 724 is more flaccid and therefore more liable to penetrate deeper into the inside of device 720, between ribs of frame 722, potentially getting caught in a morcellator or other tool.

Exemplary Single Opening Device

Figure 7D:
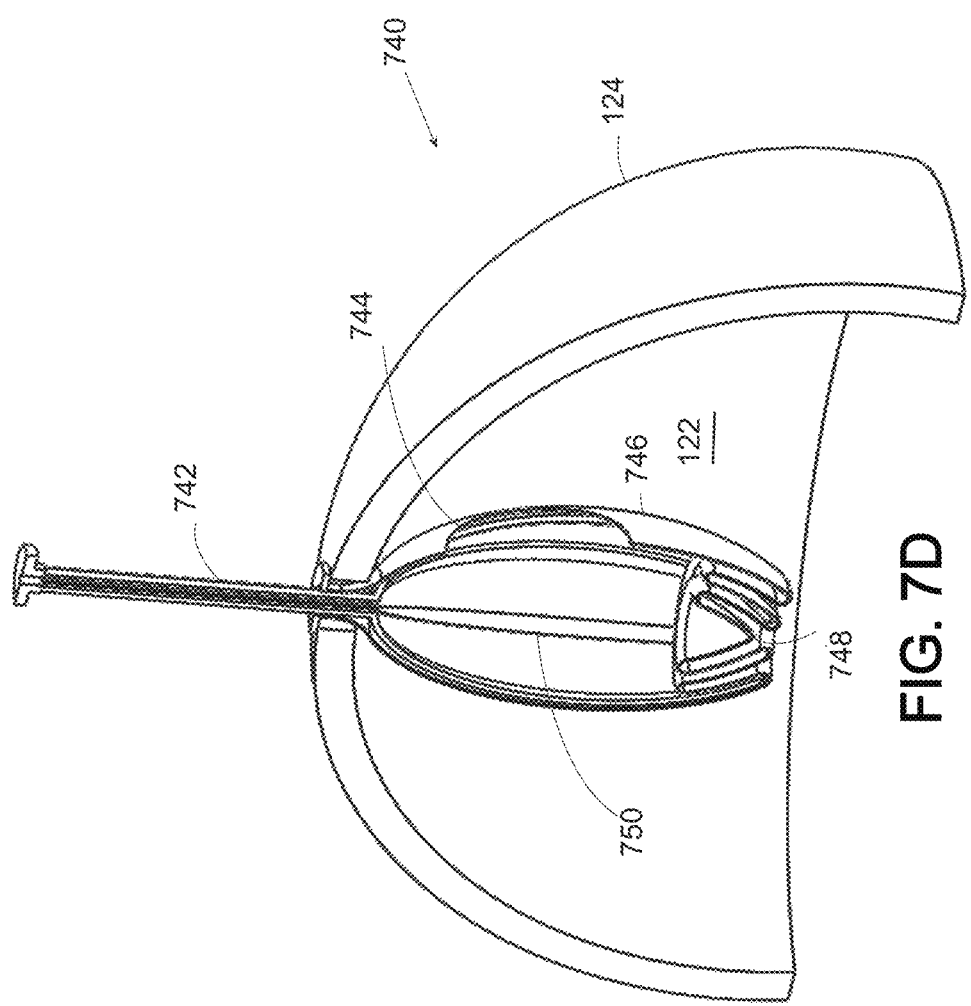
FIGS. 7D and 7E are side cross-sectional views of a workspace device with permanent rigidifying elements and a movable membrane with a movable orifice, in accordance with some exemplary embodiments of the invention.
Figure 7E:
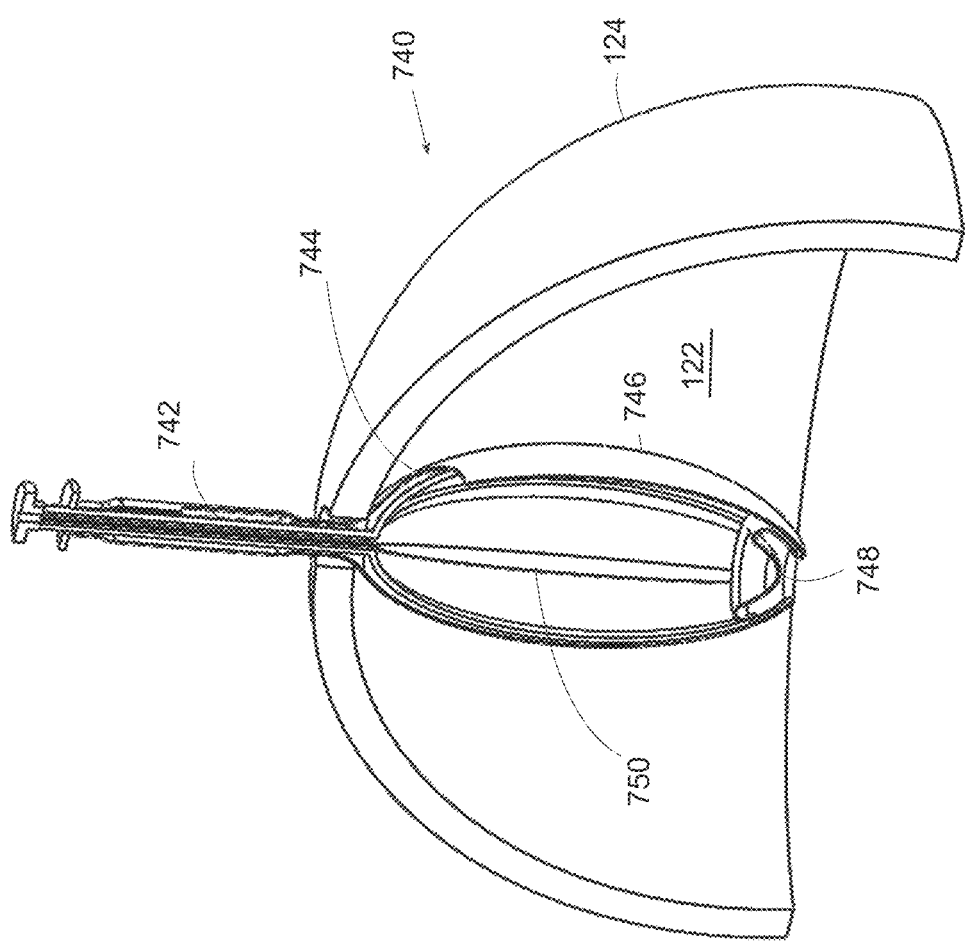

FIGS. 7D and 7E are side cross-sectional views of a workspace device 740 with permanent rigidifying elements 750 and a movable membrane 746 with a movable orifice 744, in accordance with some exemplary embodiments of the invention;

Device 720 is an example of a device with a single opening (in the membrane).

In a variation thereof, rather than membrane 724 being rolled up at a top thereof, a movable membrane 746 is provided with a collected section 748 that is, for example, rolled up or folded or otherwise collected at a lower portion thereof. In one example embodiment, membrane 746 has an orifice 744 for tissue ingress above the rolled up section thereof. FIG. 7E shows that after tissue (not shown) is brought into device 740, membrane 746 may be retracted out of the body, for example, using a tool 742. Optionally, membrane 746 is pulled up far enough that orifice 744 is now outside the body. This may require that the length of membrane 746 below orifice 744 is greater than the height of device 740 as a whole. This design can also be used if there is only the single opening shown in FIG. 7C (e.g., no separate orifice 744), except that membrane 724 is pulled up rather than unrolled.

Optionally, membrane 724 (or 746) is elastic so it can conform to frame 722 (or 750), whose cross-sectional diameter may change at different portions along device 720.

Exemplary Inflatable Device

Figure 8A:
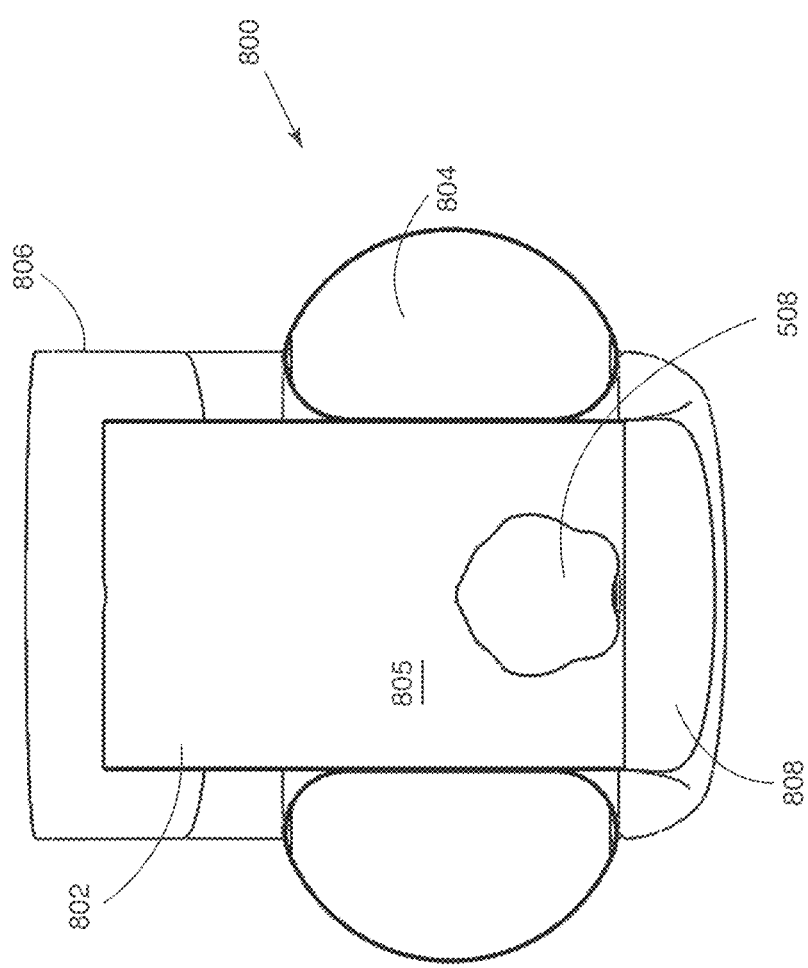
FIGS. 8A and 8B are a cross-sectional view and a side perspective view of an inflation based workspace device, in accordance with some exemplary embodiments of the invention.
Figure 8B:
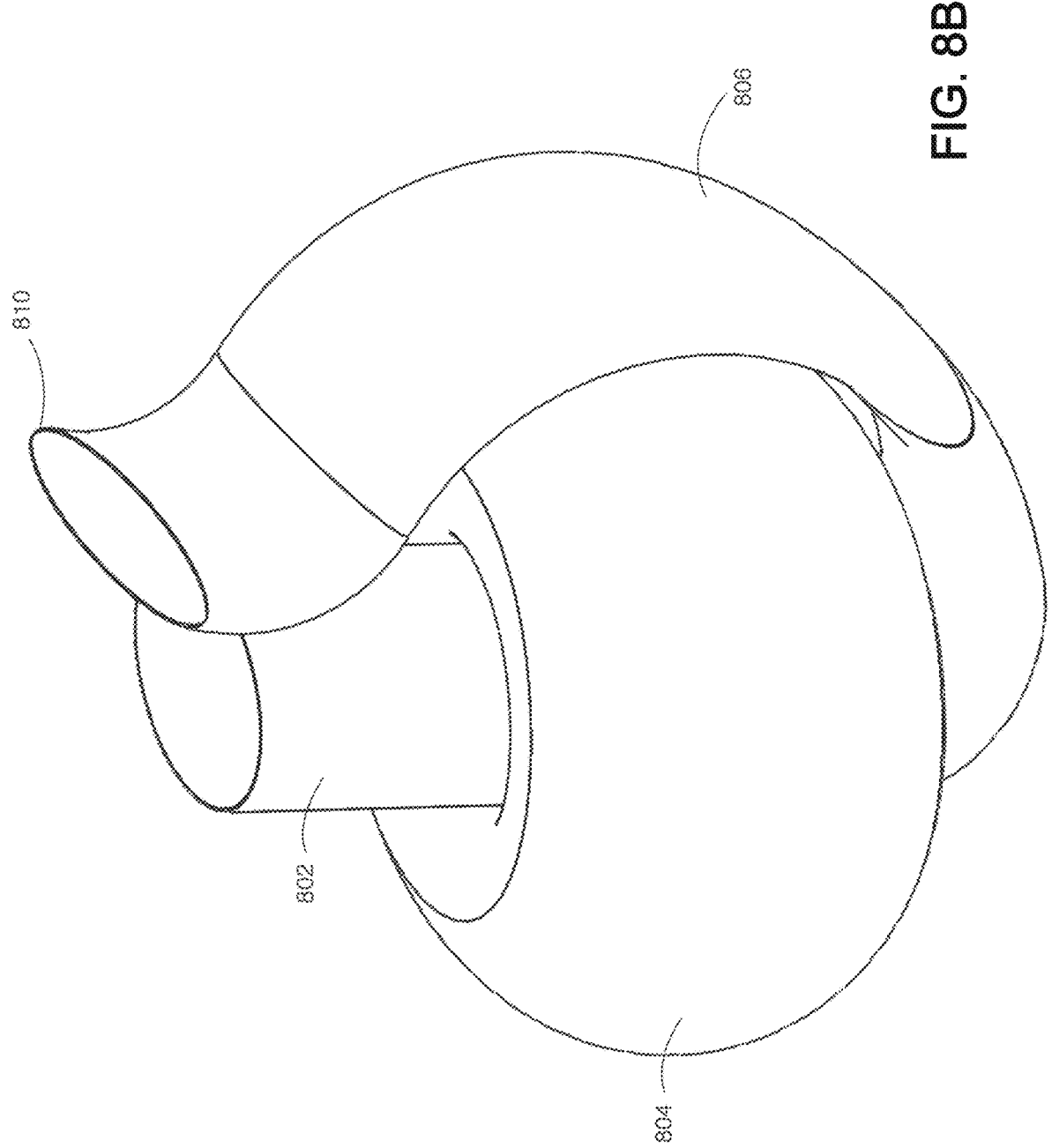

FIGS. 8A and 8B are schematic showings (cross-sectional and perspective) of an inflation based workspace device 800, in accordance with some exemplary embodiments of the invention.

In some embodiments of the invention, rigidifying is provided by inflation in addition to or instead of using naturally rigid elements. Device 800 has a double layer wall 804 which can be inflated (e.g., using saline or air, for example, using a syringe or a pump, not shown) to become taut and set the shape of device 800. A cross-abdominal wall section 802 fits in opening 128. Optionally, an orifice 808 for tissue ingress is provided below wall 804.

A flap 806 is optionally folded over orifice 808 to close it and/or seal it. Optionally, an end 810 or an extension thereof of flap 806 is pulled towards opening 128 and/or out of the body. This type of orifice closure may be used with non-inflating embodiments as well.

In some embodiments of the invention, the use of an inflatable wall allows a distance to be maintained between tools in device 800 and intra-abdominal walls, which may allow deflation of the intra-abdominal cavity before processing of tissue 508 in device 800. Optionally, such an inflatable chamber is provided with other designs of bags, for example, as known in the art where the same orifice is used for receiving tissue 508 and for receiving a morcellator.

In some embodiments of the invention, inflation is provided using a syringe coupled to wall 804 via a small diameter tube. Optionally, the tube is formed in neck 802.

A potential advantage of using a single circumferential chamber is that there is no inward sagging between rigid segments. In other embodiments, sagging is controlled by including both axial and circumferential rigidifying elements.

Figure 8C:
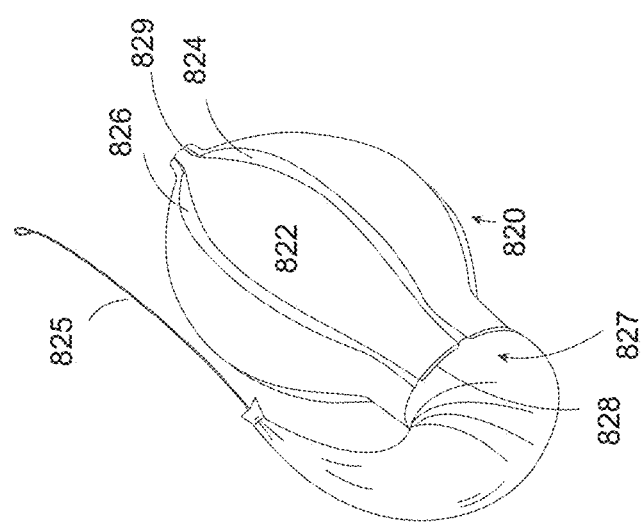

While the figure shows a single circumferential inflation chamber, other designs may be used. For example, FIG. 8C shows a device 820 having separate vertical inflatable segments 822 optionally separated by spaces 824 and 826 (which are optionally bridged by a thin membrane, not shown). Reference 828 indicates a hollow region within wall 822. Optionally, an orifice is formed between two segments 822, for example, at 826. When both such segments are inflated, the opening at 826 closes. Alternatively an orifice 827 at a bottom of the device is provided (here shown closed by a flap, which flap is optionally drawable towards opening 128 by a puller 825. Reference 829 indicates the opening which crosses the abdominal wall, for example, for insertion of a morcellator therethrough.

FIG. 8D shows a device 840, where inner volume 234 is surrounded by a wall with a plurality of circumferential segments/chambers 846, located between and optionally formed from two wall surfaces 848 and 850. An orifice 844 for tissue ingress is optionally at a bottom of device 840 and an aperture for a morcellator and for crossing the abdominal wall is provided at 842. One or more air channels (not shown) may be provided at the walls surrounding 842 for conveying air or other fluid to chambers 846. Various mechanisms, for example, as describe herein may be used for closing orifice 874.

In alternative designs both one or more vertical and one or more circumferential segments are used and/or others shapes of segments, such as helical and/or diagonal, maybe provided. In some embodiments of the invention, the size and/or shape of the device can be set based on which segments are expanded. In some exemplary embodiments of the invention, inflating only some of the chambers (e.g., if there are 2, 3, 4, 5, 8 or intermediate or greater numbers of chambers) of device 840 can be used to set a shape and/or size thereof.

It is noted that failure of a single segment 846 or 822 need not cause a catastrophic failure of the device, though it may allow some leakage.

In some embodiments of the invention, inflation is used for device deployment. For example, for device 820, inflation of a single vertical segment may provide the device with axial rigidity so it is easier to push into the body. In device 840, inflation of a circumferential chamber can encourage a device to extend away from an insertion hole without immediately volume filling.

One consideration of some embodiments of the invention is avoiding tissue damage if the outer wall of device 800 breeches and high pressure fluid or air hits intra-abdominal organs. In some embodiments of the invention, the inflatable chambers include a foam, which slows down such flow. Optionally or additionally, a low enough pressure is sued. Optionally, a liquid is used, as then lower pressures may be suitable due to the incompressibility of liquid.

Figure 8E:
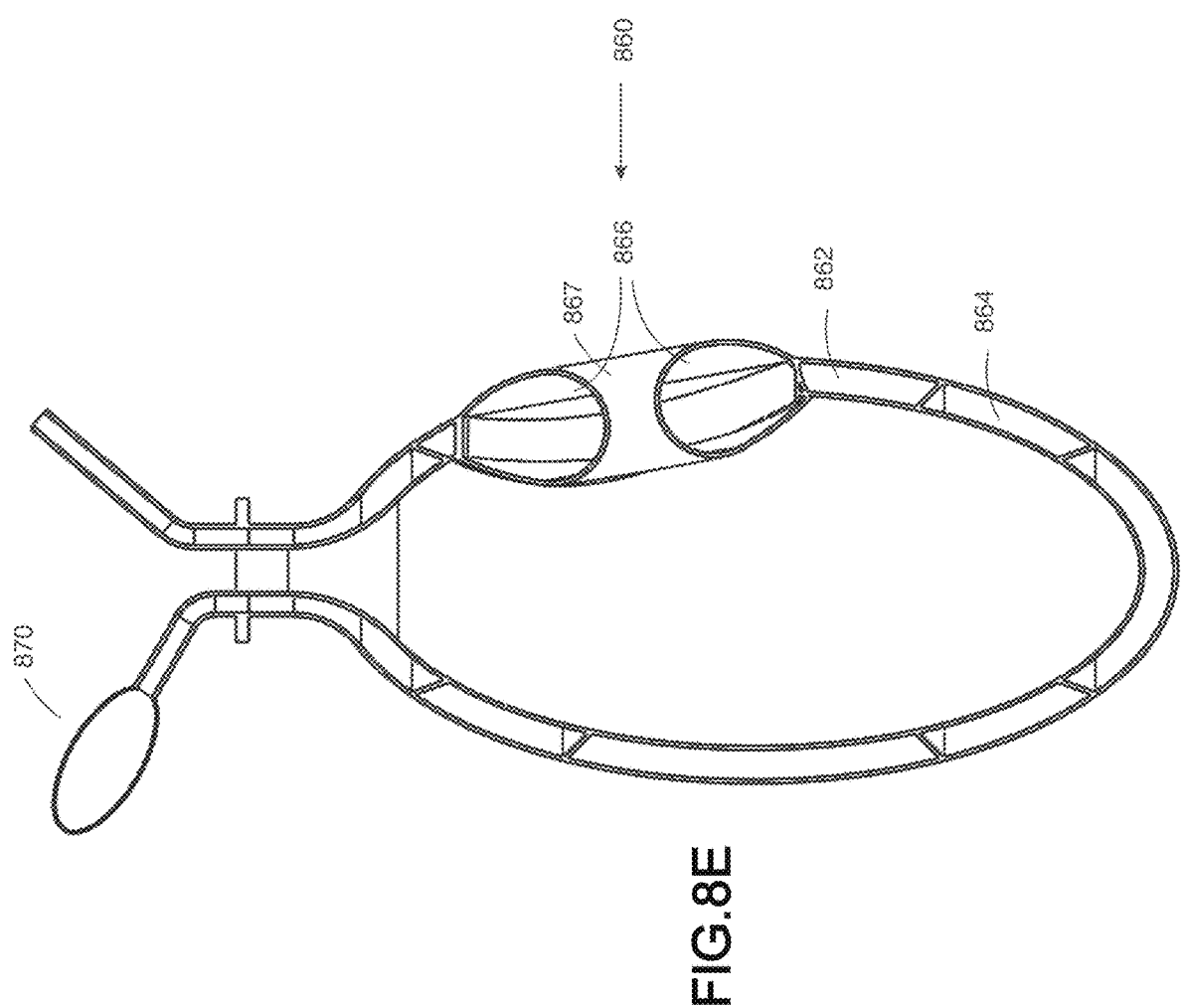
FIG. 8E is a side cross-sectional view of an inflation based workspace device illustration optional breech detection and optional orifice closure by inflation, in accordance with some exemplary embodiments of the invention.

FIG. 8E is a cross-sectional view of an inflatable workspace device 860 showing various optional features, in accordance with some embodiments of the invention. A first optional feature is the provision of one or more inflatable chambers 866 near an orifice 867 thereof. Inflation of chambers 866 may be used to close and/or seal orifice 867. A second optional feature is the provision of multiple contiguous chambers 862, 764, (e.g., no membrane) which may not share a same inflation port and/or valve.

A third optional feature is a breech indicator 870, configured to lie outside the body. In an exemplary use, pressure in chambers 862, 864 is different (typically higher) from the ambient pressure within device 860 and/or pressure in the abdominal cavity. If a tool, for example, a morcellator damages an inside wall of device 860, this will cause a reduction in pressure and thereby collapse or other change in indicator 870. Damage to the outer wall, can also be expected to generate such an indication. In some exemplary embodiments of the invention, damage to a wall will cause blood to enter indicator 870.

It is noted that this type of indicator can be used also if device 860 is a non-rigidified specimen retrieval bag and indicator 870 is open to a volume of the bag. As long as such bag is inflated, indicator 870 will show one indication. Damage to the bag wall, will cause deflation and indication 870 can show it.

It is noted that an inflatable rigidifier can also be used with a one one-hole bag. For example, the bag being inserted into the abdominal cavity as in the art. After the tissue is placed in the bag through the one opening, the edges of the opening are retracted out of the body and the bag is rigidified by inflation.

Exemplary Sleeve Devices

FIG. 9A is a schematic showing of a workspace device 900 with a sleeve 906 extendible out of the body, in accordance with some exemplary embodiments of the invention.

Device 900 has a body 902 with an orifice 904 at a bottom thereof, with sleeve 806 extension from orifice 904 alongside body 902 to outside of the body. Also shown is a morcellator 110 processing tissue 508. Optionally, a puller 912, for example, a string, wire, cable, strap or other elongate flexible tensile member can be used to pull sleeve 906 out of the body. Optionally, suction 910 is provided to an end 908 of sleeve 910, for example, to remove blood from body 902.

In some exemplary embodiments of the invention, (e.g., FIG. 8A, 8B), sleeve 906 does not exit the body, but it still isolates tissue 508 due to a fold formed therein by the extension and retraction thereof.

FIGS. 9B-9F are a series showing a workspace device 920 with an internal sleeve extendible out of the body, at various stages of use, in accordance with some exemplary embodiments of the invention.

At FIG. 9B, a tissue receiving orifice 922 is defined at a bottom thereof and a grasper 923 is optionally passed through device 920 to pull tissue 508 into device 920.

At FIG. 9C, orifice 922 is closed, for example, by advancing or bending a frame of device 920 or by pulling on a puller 926 which closes orifice 924 to an end 924. It is noted that while the frame is meant to provide rigidity, it can still be bent by suitable forces.

At FIGS. 9D, 9E, puller 926 is retracted, moving end 924 in a direction of the abdominal wall.

At FIG. 9F, puller 926 is retracted enough to bring end 924 outside of the abdominal cavity, thereby effectively sealing orifice 922.

Figure 9G:
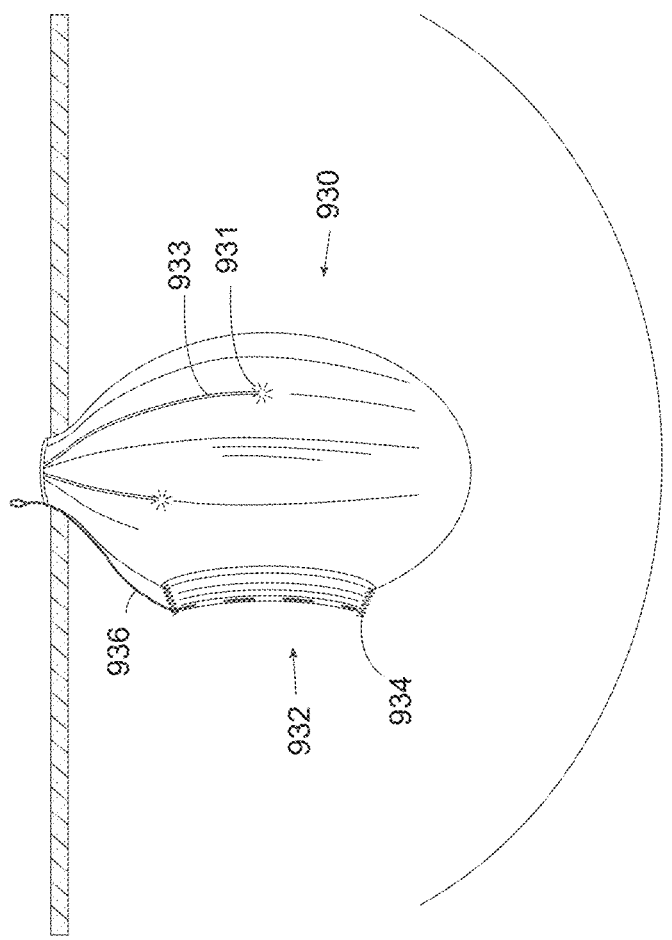
FIG. 9G is a side view of a workspace device with a lateral orifice having extendible lips, in accordance with some exemplary embodiments of the invention.

FIG. 9G is a side view of a workspace device 930 with a lateral orifice 932 having extendible lips 934, in accordance with some exemplary embodiments of the invention. FIG. 9G shows one way of collecting the sleeve that may, after tissue 508 is moved into device 920, be extended to outside of the body using a puller 936.

Also shown in FIG. 9G is a feature usable with other embodiments, of one or more light sources 931, which may be mounted on, for example, wires 933 or be exposed ends of optical fibers, and provide light inside device 930. Optionally, sources 931 are passed into chamber 228 and/or other channels predefined in or on the wall of device 930.

FIGS. 9H and 9I are views of a curved workspace device 940 with a lateral orifice 946 having extendible lips 944, in accordance with some exemplary embodiments of the invention.

FIG. 9H is a perspective view and FIG. 9I is a cross-sectional view. The shape of device 940 is optionally chosen for one or both of two reasons. First, to allow the orifice to be closer to where the tissue to be processed originates. Second, so that when processed, the morcellator is inserted at an angle, reducing the chance of damaging the aorta, which is under the umbilical region.

Lips 944 are shown to be a sleeve pleated around orifice 946. Device 940 is also shown as being an inflatable device, with chambers 954 and optional non-inflatable sections 942 setting a shape thereof. A puller 948 is shown as extending 950 through a channel 952 to engage pleated section 944. As noted herein, collection methods other than pleating can be used for sleeve 944.

Optionally, not shown, a restrictor such as adhesive or a tearable suture are provided to maintain sleeve 944 in the collected configuration thereof. Optionally, the restrictor is selectively applied so as to set which parts of sleeve 944 will open first.

FIG. 9J shows device 940, if puller 948 and extension 950 thereof is attached as a purse-string 945 to sleeve 944. Pulling on puller 948 will close orifice 469. Optionally, this is a first step in pulling sleeve 944 out of the body. For clarity, channel 952 is not shown.

FIG. 9K shows curved workspace device 940 with an extended lip 952 of orifice 944 collapsed radially and passing through channel 952 on the inside of the body in accordance with some exemplary embodiments of the invention.

FIG. 9L shows a curved workspace device 960 with an extended lip/sleeve 964 of an orifice 966 configured for passing through a closure channel 972 on an outside of device 960, when pulled by a puller 970, in accordance with some exemplary embodiments of the invention. An optional feature is a strengthening 974 at an entrance to channel 972 (which may also be provided in other embodiments herein), to guide the collapse of sleeve 964 and/or prevent tearing of channel 972 by resistance thereof.

FIG. 9M shows a workspace device 980 with an extended lip 988 of an orifice in a membrane 982 configured for passing through a restrictor 986, for closure of the orifice, in accordance with some exemplary embodiments of the invention. Optionally, puller 984 is coupled to a part 990 of lip 988 and guides part 990 through restrictor 986, pulling more of lip 988 along with it to close and seal the orifice.

FIG. 9N shows a workspace device 992 with an extended lip 996 of an orifice 994 configured for being pulled outside the device and out of the body, by a puller 948, for closure of the orifice, in accordance with some exemplary embodiments of the invention.

Exemplary Side Access Device

Figure 10A:
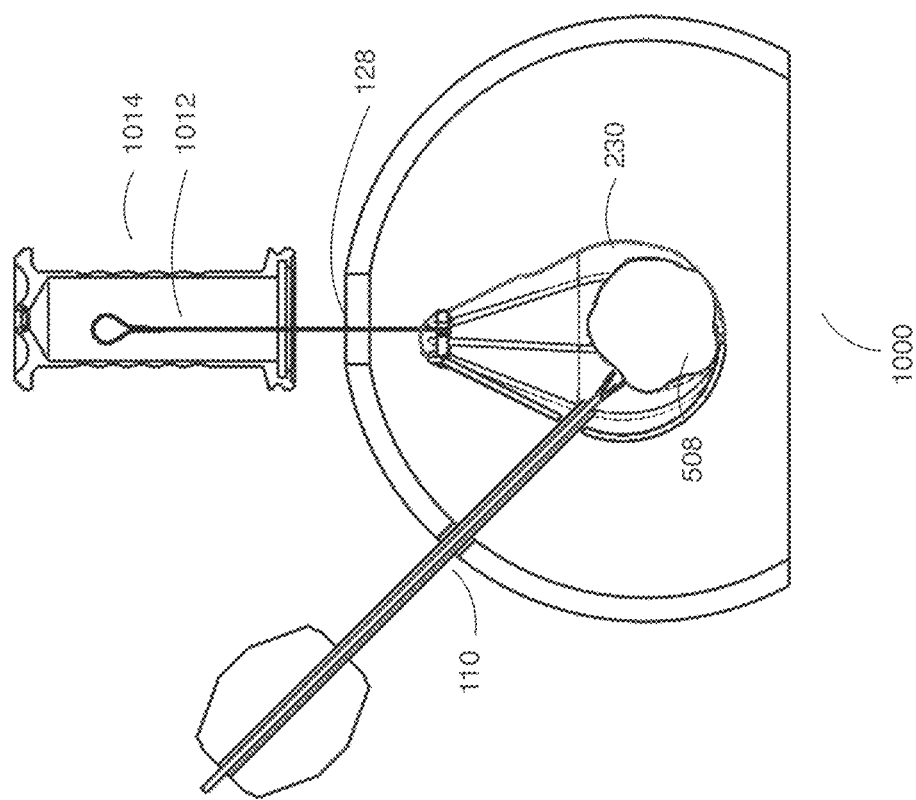
FIG. 10A is a side cross-sectional view of a workspace device having a side opening for tool insertion, in accordance with some exemplary embodiments of the invention.

FIG. 10A is a schematic showing of a workspace device 1000 where access to a morcellizer 110 or other tube is via an opening between the workspace device and the abdominal cavity, in accordance with some exemplary embodiments of the invention.

As shown, morcellizer 110 accesses tissue 508 via a first orifice, optionally including a valve for sealing, in device 1000, separate from an orifice 230 for tissue ingress. In some embodiments of the invention, the openings and orifice are opposite each other, for example, substantially diametrically opposite each other, or at least 90 or 120 degrees apart around the circumference of device 1000.

As can be seen, device 1000 does not cross the abdominal wall and is wholly within the abdominal cavity. For example, an inserter 1014 is used to insert device 1000 past opening 128 in the abdominal wall. A safety cable 1012, for example, a wire or a strap is optionally provided to assist in removing device 1000 and/or maintain it suspended in space and/or otherwise apply a positioning force to it. It is noted that such a safety cable may be provided with any of the other embodiments described herein.

Exemplary Reduced Curvature Orifice

It is noted that closing and/or sealing a curved orifice, especially with curvature in two dimensions may be difficult. In some exemplary embodiments of the invention, the orifice is designed so there is only one dimension of curvature. Optionally, such design may also prevent catching of the closure mechanism on tissue or tools, when the workspace device is retracted from the body.

FIG. 10B shows a workspace device 1020 with a sliding closure 1030, in accordance with some exemplary embodiments of the invention. It is noted that the sliding closure is just one way of closing a linear orifice. Others, for example, being described in this document.

As shown, an orifice 1026 has two lips 1028 which lie in a same plane, and when closed, optionally lie along a straight line. This may be achieved, for example, by lips 1028 being stiff and/or by suitable geometries for a membrane 1022 and one or more stiffener ribs 1024. Lips 1028 are optionally elastically predisposed to be normally open.

Reference 1034 indicates a device neck for a morcellator entrance. Slider 1030, which optionally slides into the body along a rail (not shown) on neck 1034 is a slotted elongated beam, optionally a slotted two, which pinches lips 1028 within its slot.

Figure 10C:
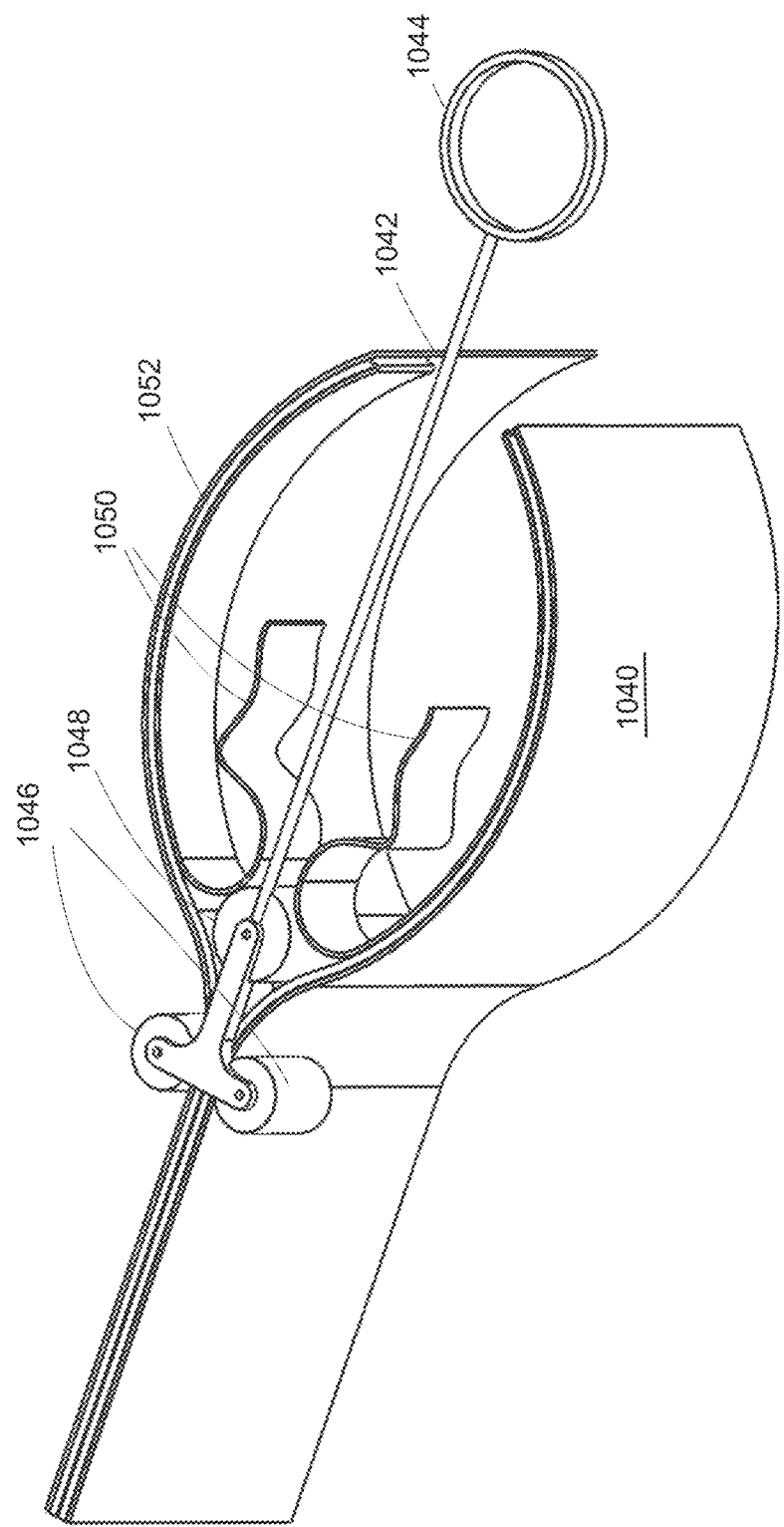
FIG. 10C is a detail view of an adhesive sealing mechanism, in accordance with some exemplary embodiments of the invention.
Figures 11, 11A:
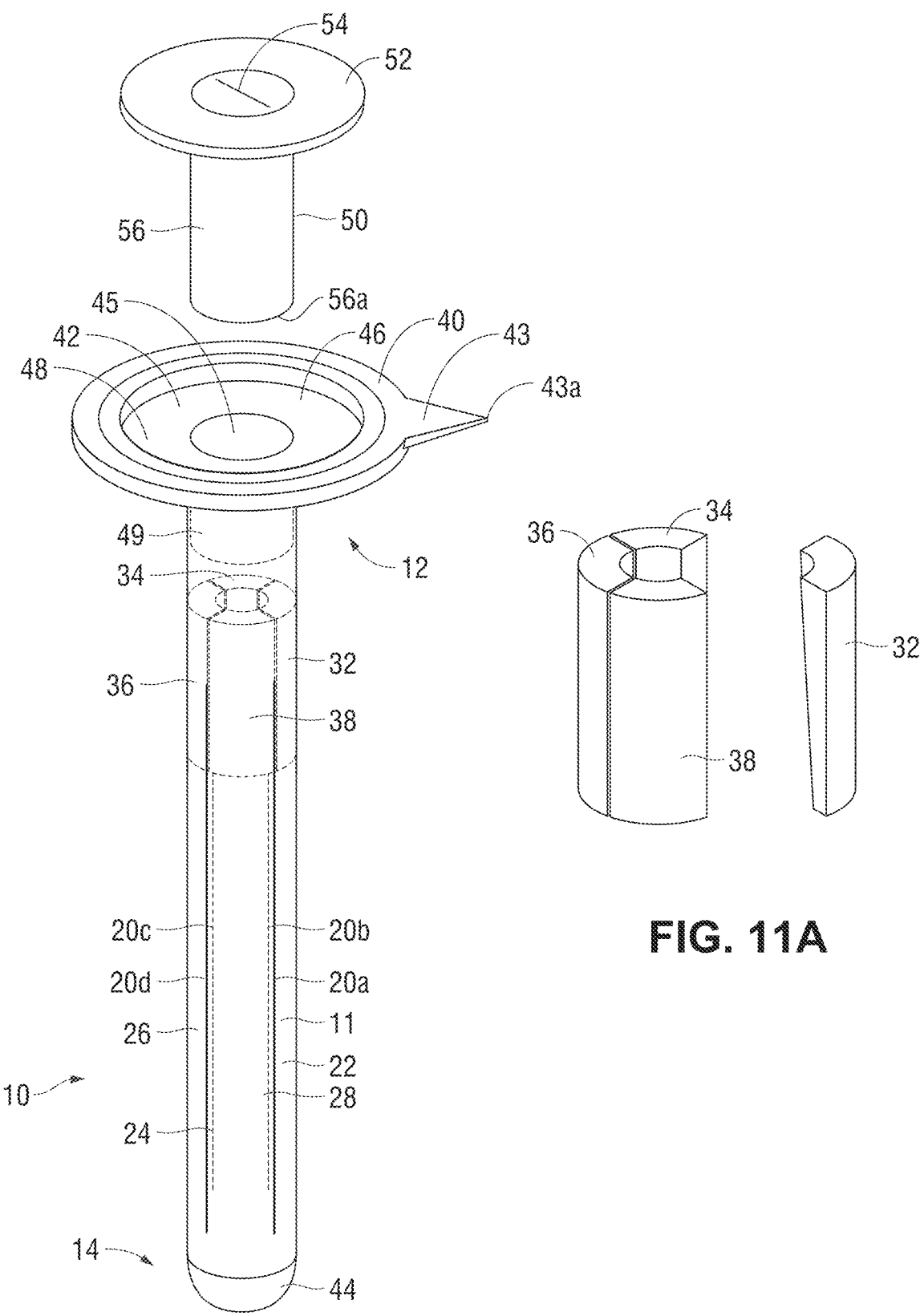
FIG. 11 is a perspective view of an embodiment of the device of the present invention, the device shown in the collapsed position.
FIG. 11A is an exploded view of the projections of FIG. 11.

FIG. 10C is a detail view of an adhesive sealing mechanism, in accordance with some exemplary embodiments of the invention. This mechanism may be used with closure 1030, or with a zipper like device as shown in FIG. 11 below or also for curved lips of an orifice.

A first lip 1040 and a second lip 1042 are attached by an adhesive layer 1052 (on one or both lips). This layer is optionally exposed when protective covers 1050 are removed therefrom. Optionally, a single mechanism is used to approximate, expose and attach the two lips. In one example, a peeler 1048, for example, a roller or a wedge, removes protective layer(s) 1050. A pair of rollers or other sliding elements 1046 press together parts of lips 1040 and 1042 which feed into the mechanism. Optionally, a puller 1044 is provided for moving the mechanism.

Exemplary Workspace Device with Zipper-Like Mechanism

Turning now to an exemplary embodiment of the device and with initial reference to FIGS. 11-18, the specimen retrieval (removal) device is designated generally by reference numeral 10 and includes a proximal portion 12 and a distal portion 14. As used herein, proximal refers to the portion or region closer to the user and distal refers to the portion or region further from the user. The device 10 has a tube (tubular portion) 11 made of an elastic material and has an outer wall 16, an inner wall 18 and a plurality of longitudinal slits 20a, 20b, 20c, and 20d which are formed through the full thickness of the wall to thereby form four separable arms or leaves 22, 24, 26, 28. In the illustrated embodiment, the four slits 20a-20d are equidistantly spaced, although varied spacing is also contemplated. Note that although four slits are shown, it is contemplated that a fewer number of slits or a greater number of slits can be provided to form a different number of arms (leaves) with the number of arms corresponding to the number of slits. The number of slits/arms will affect the shape of the device. The slits 20a-20d enable the leaves 22-28 to move from a non-spread (collapsed) insertion position to a spread or expanded position forming arch-shaped leaves. This is achieved by an expander member 50 discussed in detail below. The slits 20a-20d do not extend the full length of the tube 11 so the leaves 22-28 remain attached at a proximal end and at a distal end. The tube 11 has an opening at a proximal end and a cap 44 closes off the distal end. The cap 44 can be a separate component or integrally (monolithically) formed with the tube 11. The cap can be dome shaped or other shapes.

Attached to an internal surface of each of the leaves 22-28 is a projection or knob, also referred to herein as a rigidifying or reinforcing member, which can be made of a plastic material. More specifically, projection 32 is attached to the internal surface of leaf 22, projection 34 is attached to the internal surface of leaf 24, projection 36 is attached to the internal surface of leaf 26 and projection 38 is attached to the internal surface leaf 28. The projections 32-38 are preferably positioned only in a proximal region of the leaves 22-28, i.e., at the base portion of the leaves, as shown. The projections are preferably composed of a material having a rigidity greater than the rigidity of the tube 11 to maintain it in an expanded position. The proximal edges of projections 32, 34, 36, 38 have a proximal engaging or abutment surface (see e.g., surfaces 32a, 36a of FIGS. 12A and 12B) to receive the engaging member (expander) 50 which applies a radial force on the projections 32-38 to force them radially outwardly to expand the leaves 21 of tube 11 radially outwardly. In the illustrated embodiment, the projections 32-38 can have a wedge shape so that the outer wall angles inwardly in a distal direction. Stated another way, the projections 32-38 each taper in a distal direction so that the proximal region has a larger cross-sectional dimension than the distal region. This provides a larger engaging surface for the engaging member (expander) 50. However, it should be appreciated that other shaped projections are also contemplated to perform the function of expanding the tube 11 in response to engagement by the expander 50. It is noted that in some embodiments a rigidifying member includes also the leaf (arm).

The expander 50 optionally has a flange 52 to restrict axial movement of the expander 50 within tube 11, i.e., prevent the expander 50 from slipping into the tube 1. Expander 54 also has a slit valve 54. Tubular portion 56 extending distally from flange 52 slides through tubular portion 49 of mounting tube 48, and beyond its distal end so edge 56a can engage projections 32-38.

The tube 11 is movable (expandable) by the expander 50 from the collapsed position of FIGS. 12A, 13 and 14 to the expanded position of FIGS. 12B and 15. In the expanded position, the device 10, i.e., the tube 11, forms a box-like structure in the shape somewhat resembling a football with each of the leaves 22-28 forming an arch shape as its distal edges are connected, although other expanded shapes are also contemplated. As shown in FIG. 12A, the tube 11 in its collapsed position has an internal diameter (transverse dimension) designated by D1 which is substantially constant along a length of the tube 11. In the expanded position, the device 10, i.e. tube 11, has a larger internal diameter (transverse dimension), with D2 designating the largest diameter (transverse dimension) region.

The tube 11 can be made of transparent material to enable viewing inside the tube 11 by a laparoscope positioned in the body cavity adjacent to and outside the tube 11. The laparoscope can be inserted through another trocar port or body opening. Alternatively, the tube 11 can be composed of non-transparent material while the covering of the leaves (discussed below) and spaces between the leaves is composed of transparent material so visualization can occur between the leaves 22-28.

A material 60 covers the leaves, i.e., spans the space between the leaves 21 to form an enclosed internal space within the tube 11, designated by reference numeral 27 in FIG. 12B. In other words, the cover (or sheet(s)) creates the four walls (sides) of the device, e.g., of the somewhat football shape. The sheets or covers can be made of a transparent plastic material. A single material can be placed over the leaves 22-28 or alternatively separate sheets or covers of covering material can be placed to span adjacent leaves. In either case, an enclosed space is formed except for longitudinally extending side opening 62 between two adjacent leaves (see FIG. 5). In the illustrated embodiment, the opening 62 is shown between leaves 26 and 28 by way of example and is defined between edges 64, 66 of covering 60. The opening 62 will preferably be kept by the clinician facing the patient's anterior abdominal wall. A locking or sealing mechanism can be provided to close the opening 62, In one embodiment, shown in FIGS. 16 and 17, the locking (sealing) mechanism includes a zip-lock mechanism 68 which is slid proximally (or alternatively distally) to close the opening 62 by bringing edges 64 and 66 together. This fully encloses the specimen within the device 10 to block leakage of fluid. A double layer of zip-lock mechanisms can also be provided. In some exemplary embodiments of the invention, the zip-lock mechanism is a mechanism which brings together and interlocks two lips which have a spatially interfering design and/or which include adhesive.

Optionally, zip lock mechanism 68 is provided after deployment, from outside the body, for example, using a grasper 100. Optionally, for example, if the mechanism of FIG. 10D is used, zip-lock mechanism 68 may be removed after edges 64 and 66 are brought together.

Exemplary Draw String Closure

In the alternate embodiment of FIG. 19, the device has an opening 74 formed between leaves 26 and 28 which is closable by a string 70 (or other puller) attached to sliding mechanism 72 which is in the form of a zip-lock. More specifically, pulling of the string 70 proximally, which extends outside the patient, pulls the locking (sealing) mechanism proximally to bring together edges 76, 78 in the same manner as edges 64, 66 described above. This seals the device to prevent leakage of fluids. Note in all other respects, the device of FIG. 19 is identical to device 10 of FIG. 15, e.g., leaves 22-28, projections, distal end cap 44, expander 50, etc. so for brevity, further details will not be discussed since the configuration and function of the components of FIG. 15 are fully applicable to the embodiment of FIG. 19.

The device 10 also includes a proximal base 40 (see e.g., FIG. 11) forming a flange to engage the trocar or skin of the patient to provide a stop to prevent the entire device 10 slipping into the body cavity. The base 40 has an opening 42 to receive mounting tube 46 which has a flange 48 seated within the base 40 and a tubular portion 49 which extends into the proximal opening of tube 11 of device 10. A marker 43 has a triangular pointed tip 43a to provide a directional marker for the user which can be configured to indicate the direction of the abdominal wall, or the direction of the opening between the leaves, or other direction. Preferably, the device 10 with base 40 and tube 46 are formed integrally (monolithically) as one piece, although it is also contemplated that they can be formed as separate components.

Exemplary Usage of Zipper Device

Turning now to the method of use, and with reference to FIGS. 13-18, one method of using the device of FIG. 11 is illustrated. Note FIGS. 13-18 shown the device inserted through a trocar into the abdominal cavity, however, alternatively the device can be inserted into other regions of the body, such as the joint space or pleural cavity, and can alternatively be inserted through a natural body opening instead of through a trocar.

As shown in FIGS. 13 and 14, device 10 is inserted through a conventional trocar T1 (shown generically), through the abdominal wall W and into the insufflated abdominal cavity C. The device 10 is inserted in the low profile collapsed position as shown with the tube 11 in a cylindrical configuration to facilitate insertion. The device 10 can be inserted with the expander 50 within the device but out of engagement with the projections or, alternatively, the expander 50 can be inserted after the device 10 is inserted through the trocar as shown in FIG. 14. After positioning of the device 10 within the abdominal cavity, the tube 11 optionally can be locked in place to restrict axial movement. Next, the expander 50 is advanced distally so that its engaging surface applies a force to the projections 32-38, forcing the projections 32-38 outwardly to move the tube 11 to the expanded configuration of FIG. 15, i.e., to separate the leaves 22-28 to form the box-like structure. Next a grasper is inserted through another trocar T2 (shown generically) to grasp the specimen S and move it through opening 62 in cover 60 for placement in space 27 within tube 11. The same grasper (or a different grasper 100) then grips lock 68 (FIG. 17) and slides it proximally to bring edges 64, 66 of cover 60 together to seal the space 27 containing the specimen S as shown in FIG. 18. If the device of FIG. 19 is used, once the specimen is placed within the tube 11 by a grasper, the user pulls string 70 proximally to move the lock 72 to bring edges 74 and 76 together to seal the space 27 containing the specimen S.

Optionally, a morcellator can be inserted through the valve 54 of expander 50 and through the trocar T1 to access the interior of the tube 11. The morcellator can be a power morcellator or a non-powered morcellator such as coring tube to break up the specimen into smaller particles to facilitate removal through the laparoscopic port. FIG. 20 illustrates a power morcellator 110 with handle 112 inserted into the device to access the specimen S within space 27 of tube 11. After morcellation of the specimen S, the morcellator is removed from the body.

At the end of the procedure the expander 50 is removed or retracted from tube 11, allowing the outer tube 11 to return to the collapsed low profile configuration, e.g., its previous cylindrical shape, as shown in FIG. 21, and the device 10 can then be removed from the patient's body. The sheets of material covering the gaps between the leaves will also collapse either because of inherent elasticity or because of the pressure gradient between the peritoneal cavity and the inside of the device.

It should be noted that grasper (or other tool) 100 and/or drawstring 70 may also be used to deploy and/or reveal adhesive. Optionally, if a zipper 68 is used to bring edges 64 and 66 together, once they interlock and/or adhere, zipper 68 may be removed.

Exemplary Threaded Rigidifying Member

Figure 22C:
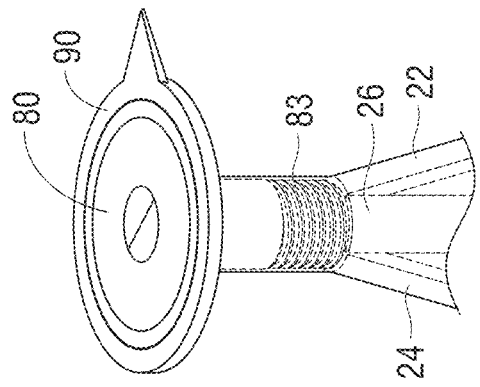
FIGS. 22A-22C are perspective views of an alternate embodiment of the device having a rotatable expander for expanding the device.
Figure 22B:
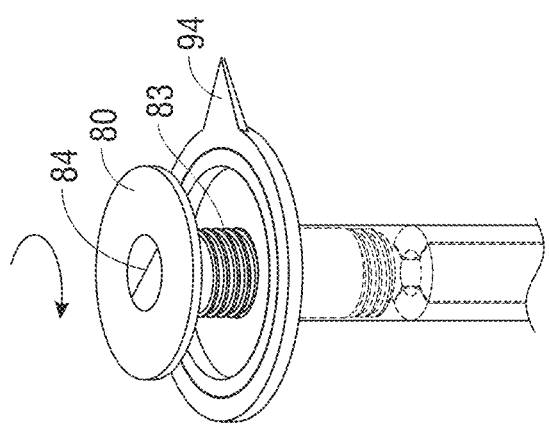
Figure 22A:
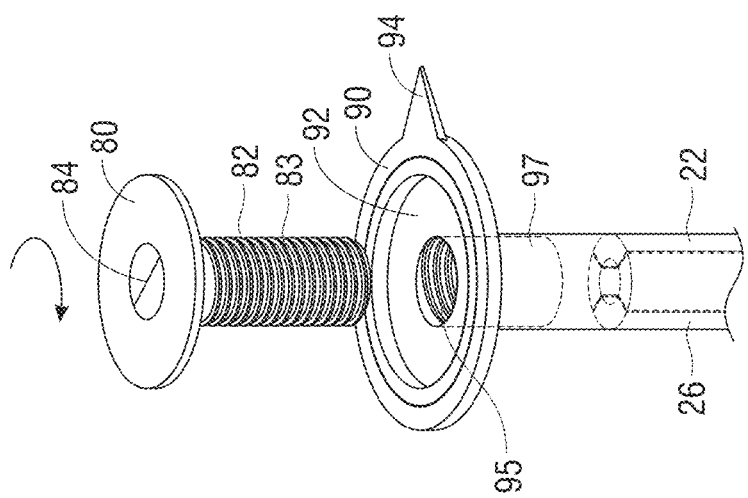

In the alternate embodiment of FIGS. 22A-22C, the expander 80 has an external screw thread 83 on the tubular portion 82 engageable with an internal screw thread 95 within mounting tubular portion 97 of tube 92. The expander 80 can be a separate component insertable into tube 92 or alternatively be provided as a unit attached to tube 92. In use, the expander 80 is rotated to advance it into tube 92 as shown in FIG. 22B. Upon sufficient advancement, the distal end of tubular portion 82 of expander 80 engages the internal projections of the leaves 22, 24, 26 and 28 to force them outwardly as shown in FIG. 22C.

Exemplary Hinged Workspace Device

Figure 23A:
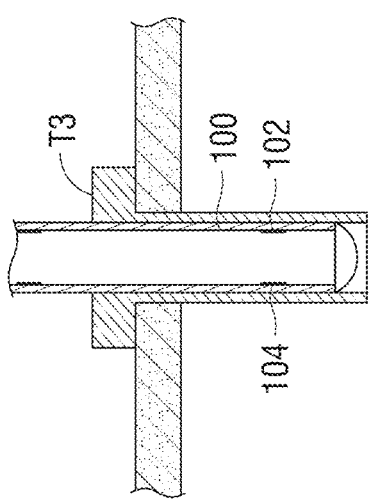
FIGS. 23A-23C are perspective views of another alternate embodiment of the device of the present invention.
Figure 23B:
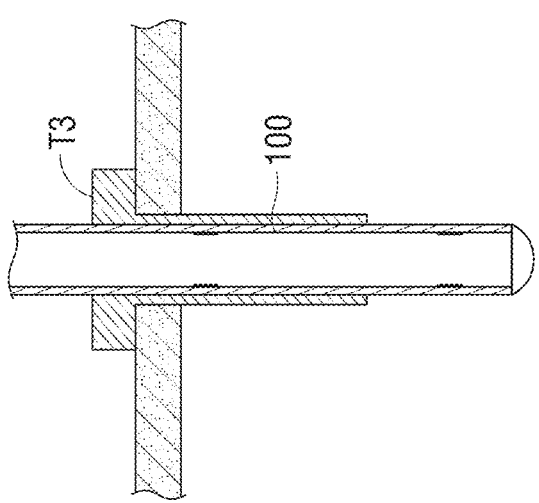
Figure 23C:
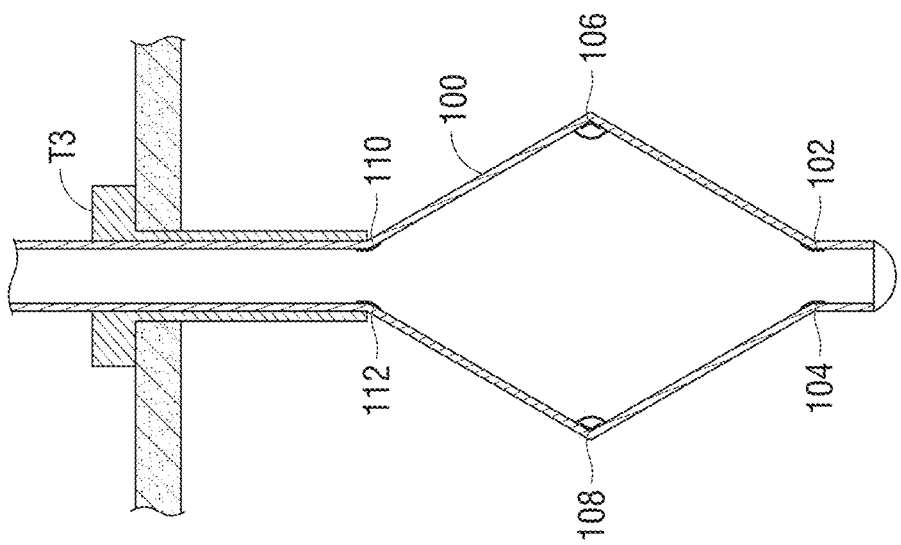

In the alternate embodiment of FIGS. 23A-23C, the specimen retrieval device is in the form of a hinged box 100. Box 100 has hinges 106, 108 having springs to enable box 100 to spring outwardly when advanced from the trocar T3. Additional hinges 102, 104 and 110, 112 are provided at the distal and proximal portions and can also have springs. As shown in FIG. 23A, the box 100 is maintained in the collapsed position by the tubular portion of trocar T3. The box 100 is advanced beyond the tubular portion of the trocar T3 into the body cavity (FIG. 23B). When sufficiently advanced into the body cavity, it will spring out into the football shaped configuration of FIG. 23C. After positioning of a specimen therein, the box 100 is retracted through the trocar T3, with the wall of the tubular portion of trocar T3 collapsing the box 100 to its cylindrical shape for withdrawal.

Some Exemplary Potential Advantages of Some Embodiments of the Invention

As can be appreciated, the device of some embodiments of the present invention can, if desired, often be used with a morcellator without at least some of the risks associated with current morcellators for several reasons. First, the device, in some embodiments thereof, creates a protected space (the "box") within the patient's body where tissue particles for removal can be isolated and morcellated without fear of scattering the tissue inside the patient's body. That is, it could allow power morcellation even when the risk of neoplasm cannot be ruled out (fibroids) because the box's walls are kept away from the morcellator and the risk of their rupture is very small. This may be useful inside the uterus.

Second, because the device, in some embodiments thereof, has semi-rigid edges it holds its shape by itself (keeps it in the expanded form) and there is no need for insufflation inside the bag. Insufflation of the body cavity is outside the box and it separates the bowel loops from the walls of the box for added safety. Since the device forms a box with sufficiently rigid walls and not a bag, the walls of the device stay away from the morcellator and are less likely to be cut by it. This not only prevents scattering of tissue but also reduces the chance of injury to the patient's organs.

Additionally, in some exemplary embodiments of the invention, the device maintains the pressure within its space below the pressure inside the peritoneal cavity so that if a hole in its wall occurs the airflow will be from the peritoneal cavity into the box and not the other way so there is no spraying of tissue particles into the peritoneal cavity. As the insufflation is outside the box, there is a pressure gradient between the peritoneal cavity and the inside of the box, i.e., the pressure inside the device is lower than the pressure in the surrounding peritoneal cavity. Therefore, if small holes occur in the cover, then the airflow will go into the box and not outside, i.e., the pressure gradient will hinder the morcellated tissue from spilling outside the device. Moreover, since insufflation goes into the peritoneal cavity, the bowel loops are kept away from the device (box), thereby allowing direct visualization of the device with a laparoscope from outside the box inserted through another port or body opening, while the morcellation of the mass or the drainage of the cyst takes place inside the box that has transparent walls. The scope is placed outside the box to monitor the morcellation through the box's transparent walls.

In some exemplary embodiments of the invention, the device can provide tissue removal in one step which is quicker that tissue removal with a bag.

Note that the device, in some embodiments thereof, can be introduced to the peritoneum through a laparoscopy port or through an opening in the cul-de-sac (colpotomy) or through the vaginal cuff after a laparoscopic hysterectomy.

The device, in some embodiments thereof, can be composed of disposable materials or reusable sterilizable materials.

Note the device, in some embodiments, prevents dissemination of tissue material during power morcellation, however, it can be used also for removal of specimens that need drainage without spillage to the peritoneal cavity (a mucinous ovarian cyst or a dermoid cyst) and whenever a specimen has to be removed from the peritoneal cavity.

A potential problem with the art which may be solved by some embodiments of the invention is as follows and relates to a desire to use power morcellation fast and safely.

Several safety issues arose over the years regarding the use of power morcellators including: 1) potential injury to the patient's internal organs including injuries to the small and large bowels, vascular system, kidney, ureter, bladder and diaphragm; 2) possible dissemination of benign tissue such as fibroids, endometriosis and adenomyosis which can lead to "parasitic growth" of the disseminated tissue, peritonitis and abscess formation; 3) possible dissemination of malignant tissue which can cause cancer upstaging and worsen the prognosis (unsuspected endometrial carcinoma could be disseminated in the same manner); and 4) potential disruption of malignant tissue pathologic architecture, which could hinder correct pathologic diagnosis or grading. Due to the risk of the dissemination of unsuspected uterine sarcoma, the FDA issued a safety communication on April 2014 (which was updated on November 2014) recommending against using power morcellation in the majority of women undergoing myomectomy or hysterectomy for uterine fibroids. This has led to a sharp decline in the use of power morcellators in the U.S.

In attempts to prevent the dissemination of morcellated tissue inside the peritoneal cavity, special specimen bags have been used in several techniques. One technique involves placing the specimen in a bag, bringing the free edges of the bag through a laparoscopy port that has been extended (in essence turning the procedure to a minilaparotomy) and morcellating the specimen manually. This has the potential disadvantage of having larger incisions of open surgery and of extending the time of the operation. Another technique is placing the specimen in a bag, bringing the free edges of the bag through a culdotomy (or through the open vagina in case of a total laparoscopic hysterectomy) and manually morcellating the specimen. This has the potential disadvantage of extending the time of the operation.

Another problem relates to where an imaging device is placed for imaging the morcellation. It may be difficult to visualize the morcellation from outside the bag unless another insufflation source is connected to keep the pneumoperitoneum outside the bag. Such a scope can view the morcellation from inside the bag, however, in this technique the integrity of the bag may be compromised and leakage of tissue might occur during the morcellation or when the bag is removed after the morcellation.

There are several potential disadvantages to the use of a bag during morcellation. First, there could be leakage from the bag. The bag could be defective as a result of the manufacturing process or as a result of the manipulation of the bag during the procedure, i.e., due to insertion and removal of the bag, inadvertent laceration by the tenaculum or by the morcellating device. Also, pulling the tissue towards the morcellator can pull with it the bag wall that might be cut inadvertently by the morcellator. Second, in the technique where the bag is insufflated, the pressure inside the bag is higher than the pressure in the surrounding peritoneal cavity. Thus, even a small defect in the bag can lead to spraying of tissue containing fluid (blood, irrigation fluid) to the surrounding environment. Third, the process of setting up the bag for morcellation is time consuming, and in some cases up to twenty minutes could be spent on this step.

It is noted that devices as described in accordance with some embodiments of the invention can work with a range of different morecellators, including, potentially morecellators with a potential to damage retrieval bags and/or spray tissue. Possibly, even an exposed blade may be used, if restrained in movement by the frame of the device.

Exemplary Use of Exemplary Workspace Device/s

Figure 24:
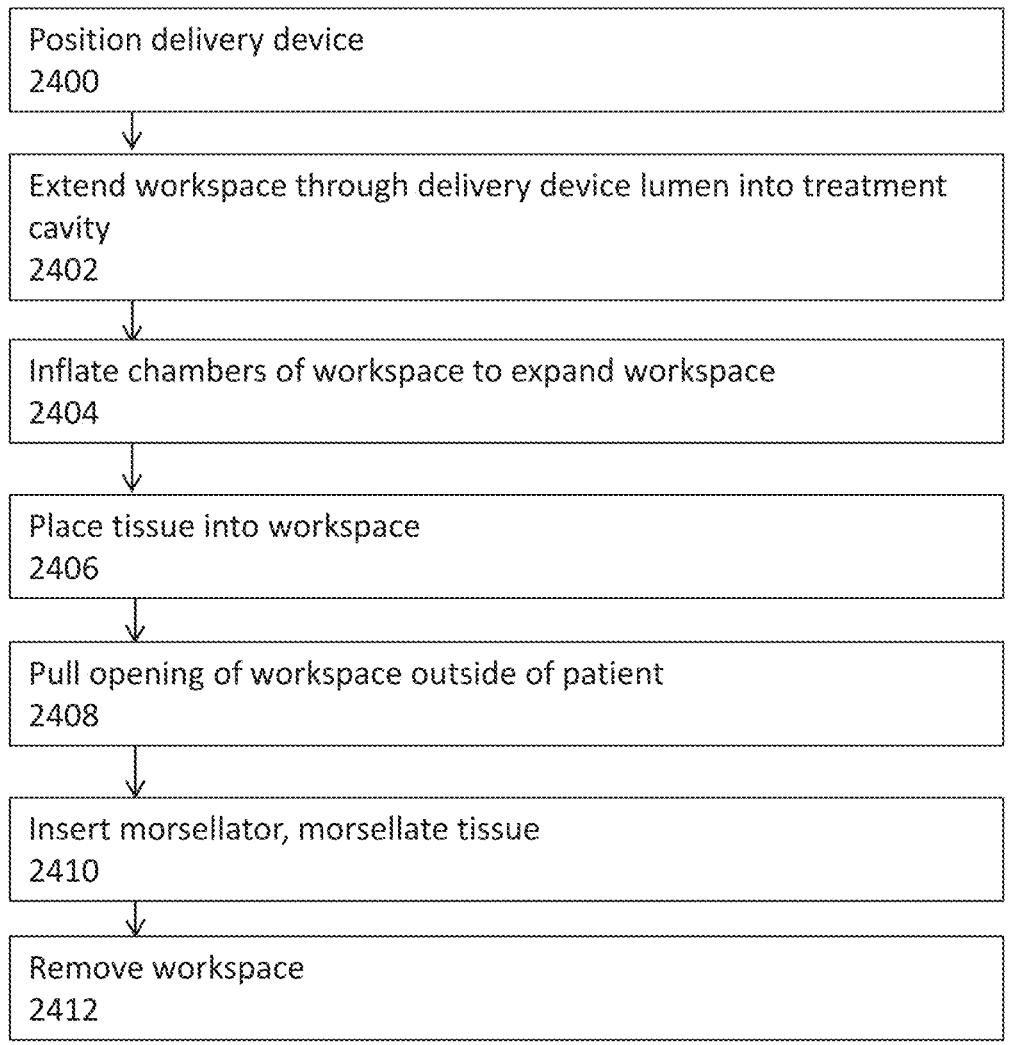
FIG. 24 is a method of use of a workspace device, according to some embodiments of the invention.

FIG. 24 is a method of use of a workspace device, according to some embodiments of the invention.

At 2400, in some embodiments, a delivery device is positioned. In some embodiments, positioning of the delivery device includes inserting at least a portion of the delivery device through an incision into a patient cavity. In some embodiments, the cavity is an insufflated abdominal cavity. In some embodiments, once the delivery device is inserted a user manipulates a portion of the delivery device remaining outside the patient, for example, to place the portion of the delivery device within the cavity in a desired position. In some embodiments, one or more type of imaging (e.g. a camera located within the cavity) is viewed by the user to position the delivery device in the desired position.

At 2402, in some embodiments, a workspace device is delivered to the cavity. In some embodiments, the workspace device is delivered through a delivery device lumen, which, in some embodiments, extending from outside the patient to the cavity. In some embodiments, the collapsed workspace device is advanced through the delivery device lumen. In some embodiments, the collapsed workspace device, is inserted in a collapsed configuration into the lumen. Alternatively or additionally, in some embodiments, the delivery device is provided with a collapsed workspace device pre-loaded within the lumen.

At 2404, in some embodiments, chambers of the workspace device are inflated. In some embodiments, inflation of the workspace devices acts to expand the workspace from the collapsed configuration to an open configuration. For example, including one or more feature as described regarding step FIG. 25.

In some embodiments, the workspace device is fully delivered into the cavity (e.g. fully outside the delivery device lumen) before inflation is initiated. Alternatively, in some embodiments, inflation begins when the workspace device is within the delivery device lumen or at least partially extended out of the delivery device lumen. In some embodiments, inflation of the workspace device moves the delivery device out of the lumen into the cavity.

At 2406, in some embodiments, tissue is placed into the workspace. Optionally, in some embodiments, the workspace is further expanded around the tissue.

In some embodiments, the order of steps 2404 and 2406 are reversed, with the tissue being place in and/or on and/or in close proximity to the collapsed workspace device and the workspace device is then expanded around the tissue. In some embodiments, the workspace is collapsed in one direction but expanded in a second direction, the workspace is the positioned near and/or in contact with the tissue to be removed and/or the tissue is at least partially inserted into the workspace. In some embodiments, the workspace is then expanded around the tissue, for example, where chambers (e.g. circumferential chambers) are expanded sequentially and/or in a predefined order.

In some embodiments, the workspace device is opened before inflation and/or full inflation of the workspace device, for example, enabling tissue to be placed within the workspace device before inflation (and/or full inflation) of the device. In some embodiments, a workspace device is expanded, at least partially, by an additional element. For example, in some embodiments, an element (e.g. a rigid element) is contacted to the workspace device to position and/or open and/or expand it (e.g. a handle inserted into the cavity which hooks onto the device and a user pulls on the handle to open the workspace device). In some embodiments, the workspace device is opened by an additional inflatable element, e.g. balloon, which for example, placed within the device expanded and then removed e.g. before use of the workspace device.

At 2408, in some embodiments, the workspace opening is pulled out of the patient, e.g. through an incision and/or port through which the workspace was inserted.

At 2410, in some embodiments, a morsellator is inserted through the workspace opening outside the patient and into a body of the workspace within the patient cavity. In some embodiments, the morsellator then morsellates and/or extracts the tissue within the cavity.

At 2412, in some embodiments, once the morcellization process is finished, the workspace is removed from the patient cavity. In some embodiments, the workspace is collapsed in one or more direction during and/or before removal.

Figure 25:
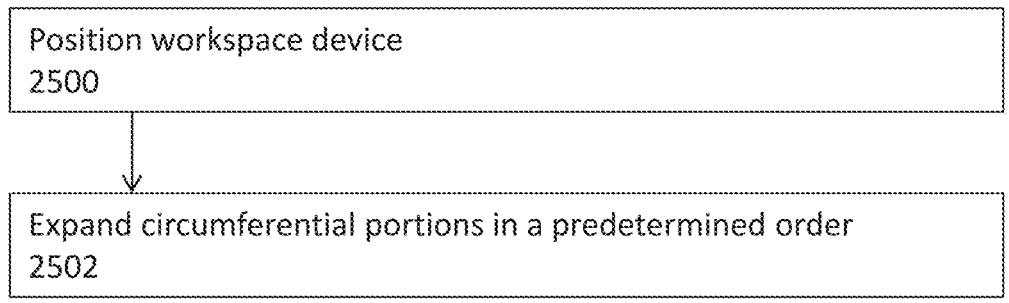
FIG. 25 is a method of using a workspace device, according to some embodiments of the invention.

FIG. 25 is a method of using a workspace device, according to some embodiments of the invention.

At 2500, in some embodiments, an at least partially collapsed workspace device is positioned within a patient cavity. For example, in proximity and/or in contact with tissue to be removed and/or treated.

At 2502, in some embodiments, the workspace device is expanded, by inflation of inflatable compartment/s. For example, in some embodiments, an at least partially inflated compartment pushes against adjacent compartment/s (and/or adjacent circumferential segments of the same compartment e.g. in the case of a helical compartment) the pressure acting to expand the workspace device. In some embodiments, inflation actus to unfold and/or unroll portions of the workspace device to transfer the workspace device from a collapsed configuration to an expanded configuration.

In some embodiments, expansion includes expansion of is of circumferential segments of the workspace device, in a predetermined order. In some embodiments, expansion is by inflation of the circumferential segments, which include, in some embodiments, a plurality of inflatable chambers.

In some embodiments, inflation expands the workspace device in a pre-determined direction and/or sequence of chamber expansion. For example, from a bottom to a top of the device, vice versa or from the middle of the device outwards. In some embodiments, a user selects a direction of expansion, for example, by selecting a tube (e.g. from a plurality of tubes) through which to inflate the device, each tube, in some embodiments, providing a different predetermined direction and/or sequence of expansion.

In some embodiments, inflation opens a workspace opening and/or increases a length of the workspace (where, in some embodiments, the length is 60-120° or perpendicular, or lower or higher or intermediate ranges or angles to a plane of the opening).

Alternatively or additionally, in some embodiments, a workspace includes an opening which is elastically compressed within the lumen of the deployment device and, in some embodiments, as the workspace is expelled from the lumen the opening elastically opens. Where inflation expands the workspace by increasing a length of the workspace and/or increasing a size of the opening beyond the extent of opening associated with elastic relaxation of the opening.

In some embodiments, inflation of the chambers rigidizes the workspace, for example, sufficiently so that the workspace is able to maintain its shape under pressure of the cavity e.g. cavity insufflation.

FIGS. 26A-D are simplified schematics of use of a workspace device 2602 within a patient cavity 2642, according to some embodiments of the invention.

In some embodiments, FIG. 26A shows workspace 2602 in a deployed configuration, where, for example, in some embodiments, the workspace is collapsed onto a base portion of the workspace. In some embodiments, the deployed (also termed "partially collapsed") or a fully collapsed (collapsed in both axial and radial directions) workspace is positioned in proximity and/or in contact with tissue 2640 (e.g. an organ, a portion of an organ) to be removed. In some embodiments, the workspace is then expanded by being inflated, by introduction of fluid (e.g. saline, e.g. air, e.g. $CO_2$) through a tube 2616. In an exemplary embodiment, inflation is effected manually by a user at a hand pump 2618. FIG. 26B, in some embodiments, shows the workspace device 2502 partially extended and, in the illustration, partially containing tissue 2640. In some embodiments, workspace chambers are inflated sequentially, from a top (most removed from the base of the device) downwards. Alternatively, in some embodiments, inflation starts with a chamber adjacent to the base, the chambers inflated sequentially upwards.

FIG. 26C, in some embodiments, shows a sectional view of workspace device 2602 expanded to fully contain tissue 2640. In some embodiments, a workspace device 2602 is expanded to a dimension which contains tissue 2640, where, in some embodiments, the expansion is less than a full expansion of the workspace device. In some embodiments, a rim portion at a top of the workspace device is pulled through a laparoscopic opening e.g. through a port 2644, the port, in some embodiments, being a portion of delivery device (e.g. including one or more feature as described and/or illustrated regarding delivery device 200 FIGS. 28A-D).

FIG. 26E is a simplified schematic of a workspace device 2602 within a cavity 2642, according to some embodiments of the invention.

In some embodiments, FIG. 26E illustrates a workspace device 2602 as the workspace device is positioned within patient cavity 2642 in a collapsed (or partially collapsed e.g. deployed configuration) configuration, for example, by a user manipulating a delivery device 2600. FIG. 26E illustrates, in some embodiments, a partially expanded device where the device has been opened, e.g. by elastic relaxation of rim reinforcement portion/s 2628.

FIGS. 40A-G are simplified schematic cross sections showing expansion of a workspace device, according to some embodiments of the invention.

Figure 40A:
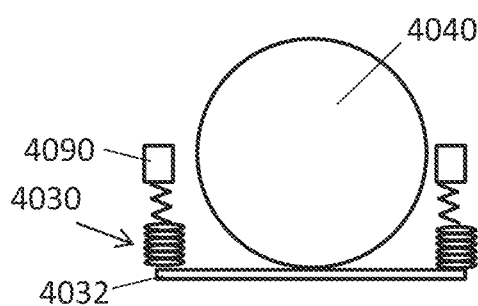
FIGS. 40A-G are simplified schematic cross sections showing expansion of a workspace device, according to some embodiments of the invention.
Figure 40B:
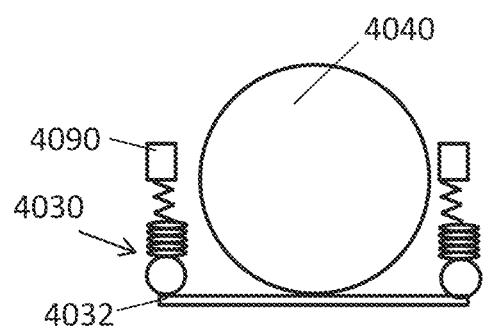
Figure 40C:
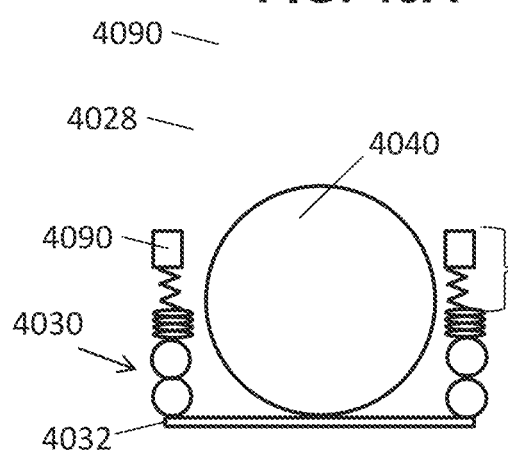
Figure 40D:
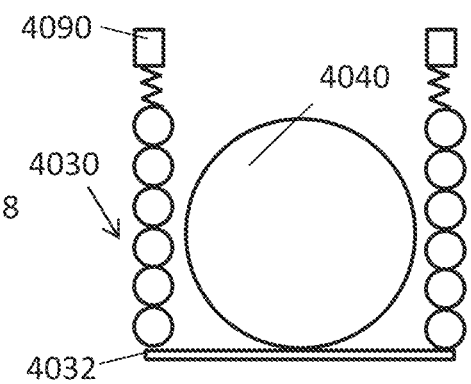
Figure 40E:
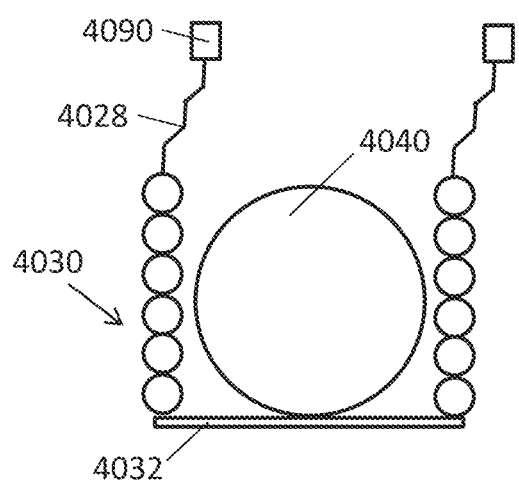

In some embodiments, FIGS. 40A-G shows an at least partially collapsed workspace device (e.g. including one or more feature as illustrated and/or described regarding workspace device 2602 FIG. 26A and/or 2702 FIGS. 27A-F). In some embodiments, the device is opened, e.g. by elastic relaxation of reinforcement portion/s 4090 and/or of a base portion 4023. FIG. 40B illustrates inflation of walls 4030 by inflation of a segment at one end of the device, e.g. at a base of the device, where, FIGS. 40C-D illustrate sequentially inflation of adjacent inflatable segments until full inflation illustrated by FIG. 40D. In some embodiments, a rim portion 4028 is then expanded and/or extended (e.g. when the opening of the device is pulled towards and/or through an opening in the patient wall) e.g. by unfolding as illustrated and/or by one or other method e.g. unrolling, inflation, elastic deformation, plastic deformation.

Figure 40F:
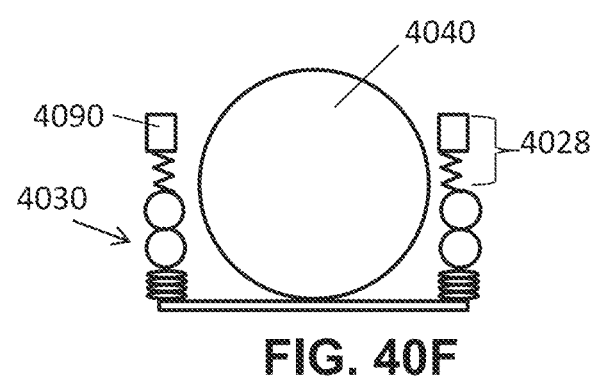

FIG. 40F illustrates an embodiment where expansion from the configuration of FIG. 40A to that illustrated in FIG. 40D, is where the segments inflate sequentially starting from a top of the device, proximal to a rim portion 4028.

Figure 40G:
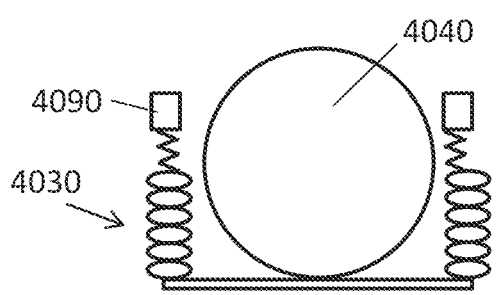

FIG. 40G illustrates an embodiment, where expansion from the configuration of FIG. 40A to that illustrated in FIG. 40D, is where a plurality (e.g. all) of the wall segments 4030 inflate simultaneously.

FIGS. 27A-F are simplified schematic views of use a deployment device 2700 and a workspace device 2702, according to some embodiments of the invention.

In some embodiments, FIGS. 27A-F illustrate use deployment and/or use of a workspace device 2702 within a patient cavity 2742 (which is, e.g. a patient abdominal cavity).

Figure 27A:
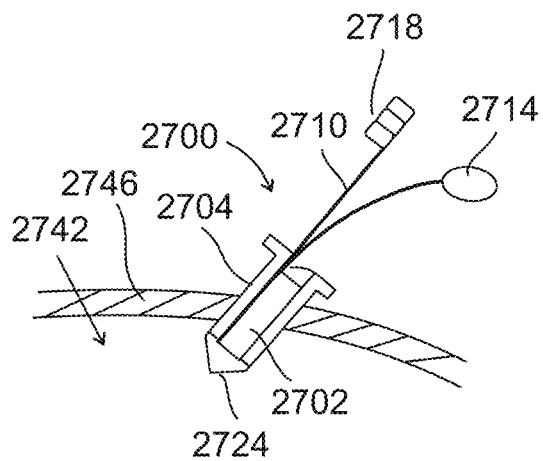
FIGS. 27A-F are simplified schematic views of use a deployment device and a workspace device, according to some embodiments of the invention.

FIG. 27A illustrates, in some embodiments, positioning of deployment device 2700 (e.g. including one or more feature as described with respect to step 2400 FIG. 25). For example, deployment device 2700 is inserted through a cavity wall 2746 (e.g. abdominal wall) e.g. through an incision in wall 2746. In some embodiments, delivery device includes a tip 2724 which includes one or more feature as illustrated in and/or described regarding tip 2824 FIGS. 28A-D.

In some embodiments, deployment device 2704 includes one or more lock which prevents the workspace from being discharged from the deployment device, for example, before the deployment device is in position. In some embodiments, the one or more lock includes a manual lock (e.g. pin connecting the handle 2718 to the deployment device body 2704) which a user disengages, for example, once maneuvering the deployment device into a desired position (e.g. pin is removed). In some embodiments, the one or more lock includes a lock which releases automatically, for example, when pressure between the deployment device and patient surface 2746 is sufficiently high.

Figure 27B:
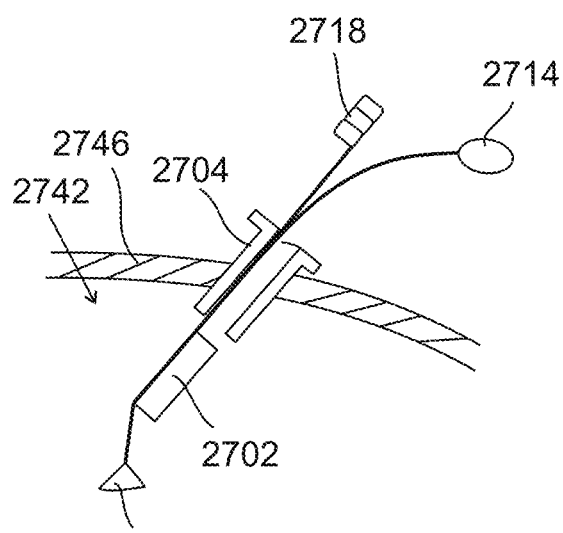

FIG. 27B illustrates, in some embodiments, workspace device 2700 extended through a lumen of the delivery device into cavity 2742 (where extending the workspace, in some embodiments, includes one or more feature as described with respect to step 2402 FIG. 25). In some embodiments, workspace 2702 is extended by a user pushing on and/or increasing a length of a handle 2718. In some embodiments, the workspace is positioned within the cavity by a user manipulating the handle e.g. from outside the patient.

Figure 27C:
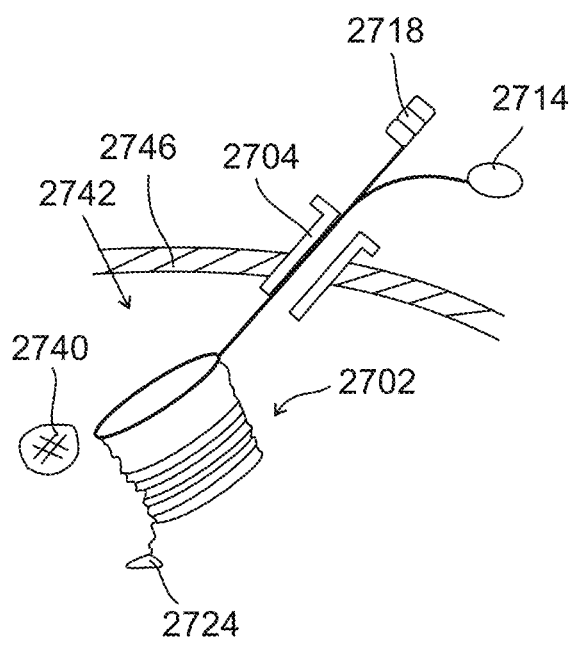

FIG. 27C illustrates, in some embodiments, positioning workspace device 2724 with respect to tissue 2740 to be treated and/or partial inflation and/or expansion of the workspace device (e.g. including one or more feature as described with respect to step 2404 FIG. 25).

Figure 27D:
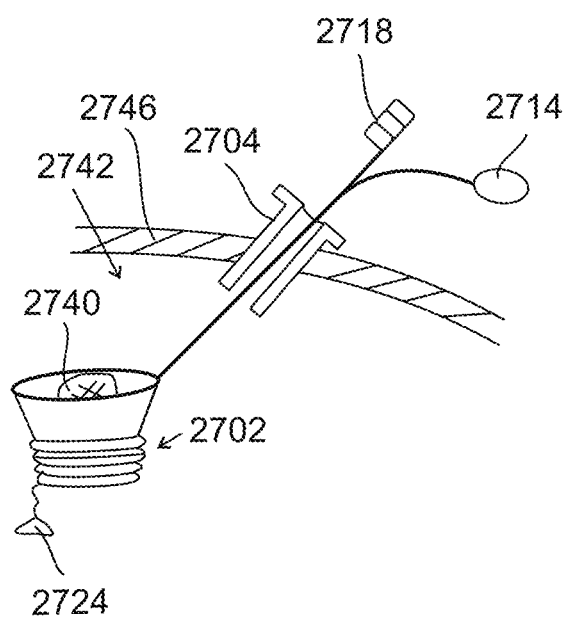

FIG. 27D illustrates, in some embodiments, insertion of issue into a lumen of workspace device 2702 (e.g. including one or more feature as described with respect to step 2406 FIG. 25). In some embodiments, tissue 2740 is manipulated and/or workspace is manipulated (e.g. by user movements of handle 2718) to place tissue 2740 into a lumen of workspace device 2702. In some embodiments, (e.g. as illustrated in FIGS. 26A-C), workspace device is pulled around and/or expanded (e.g. by inflation and/or other means) around tissue 2740.

Figure 27E:
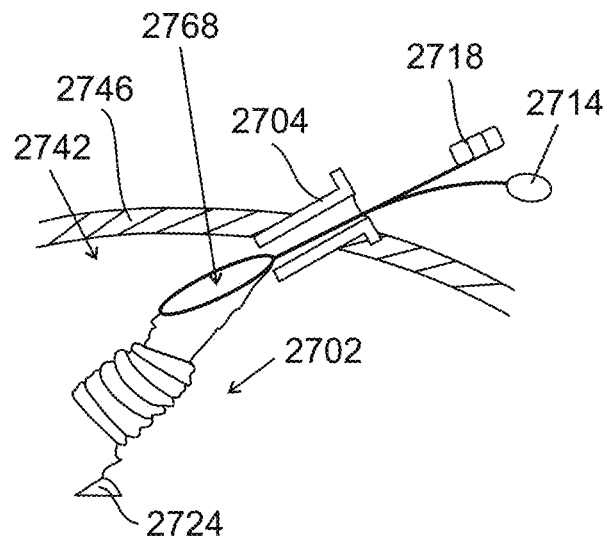

FIG. 27E illustrates, in some embodiments, pulling an opening 2768 of the workspace device outside of patient, (e.g. including one or more feature as described with respect to step 2408 FIG. 25). In some embodiments, opening (which in some embodiments, includes a rim with one or more feature as illustrated and/or described regarding rim 2828 FIGS. 28B-D) is extracted by pulling on handle 2718. In some embodiments, the delivery device 2704 is also removed from the opening into the cavity before, during or after extraction of the workspace device opening. In some embodiments, the workspace device is extracted through the lumen of the delivery device, which, in some embodiments, remains in situ e.g. a morcellator is inserted into the cavity through the delivery device lumen.

Figure 27F:
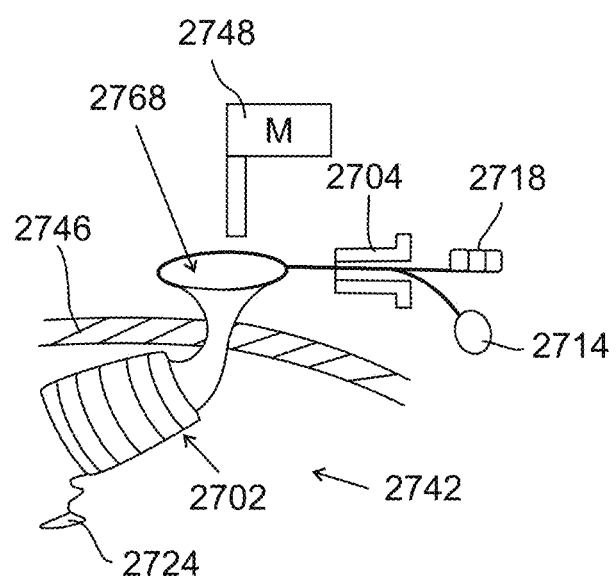

FIG. 27F, in some embodiments, illustrates positioning of a morsellator for insertion into the workspace device and cavity, where insertion of the morcellator e.g. includes one or more feature as described with respect to step 2410 FIG. 25.

In some embodiments, workspace 2702 is removed e.g. by pulling on handle 2718, where removal, in some embodiments, includes one or more feature as described with respect to step 2412 FIG. 25)

Exemplary Inflatable Workspace Devices

Figure 28A:
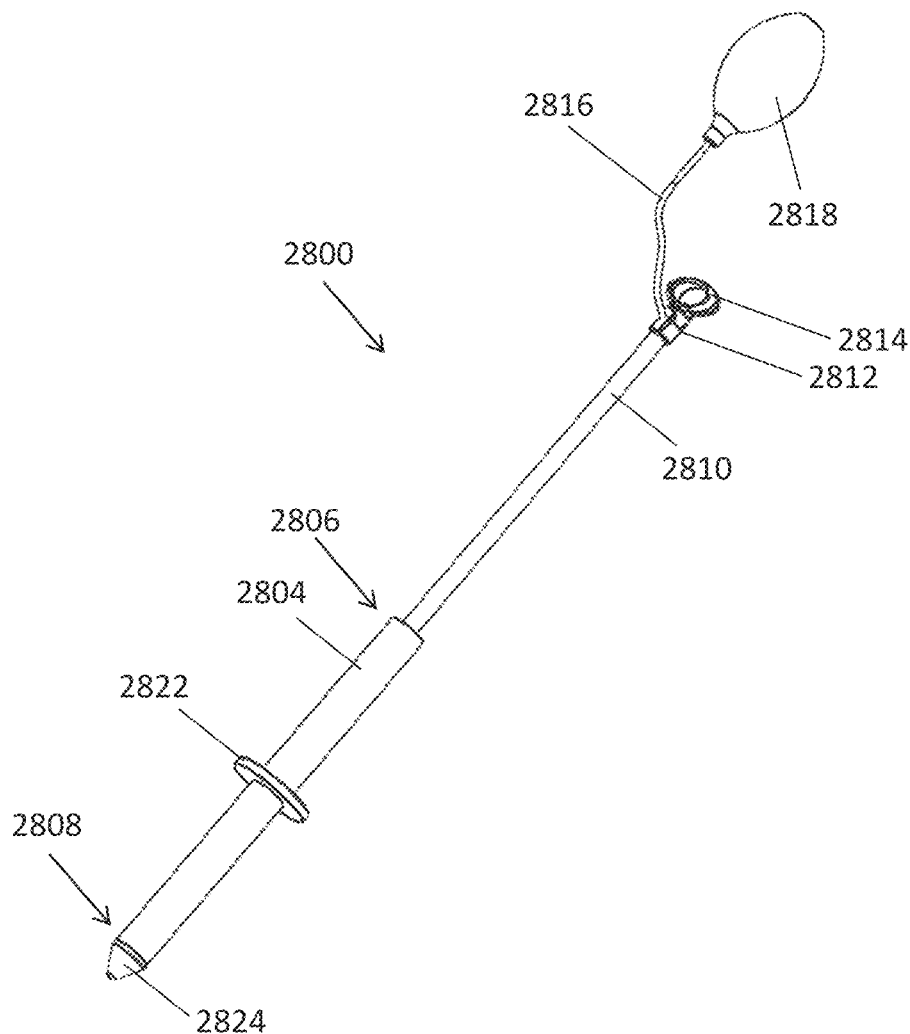
FIG. 28A is a simplified schematic perspective view of a deployment device 2800, according to some embodiments of the invention.

FIG. 28A is a simplified schematic perspective view of a deployment device 2800, according to some embodiments of the invention.

Figure 28B:
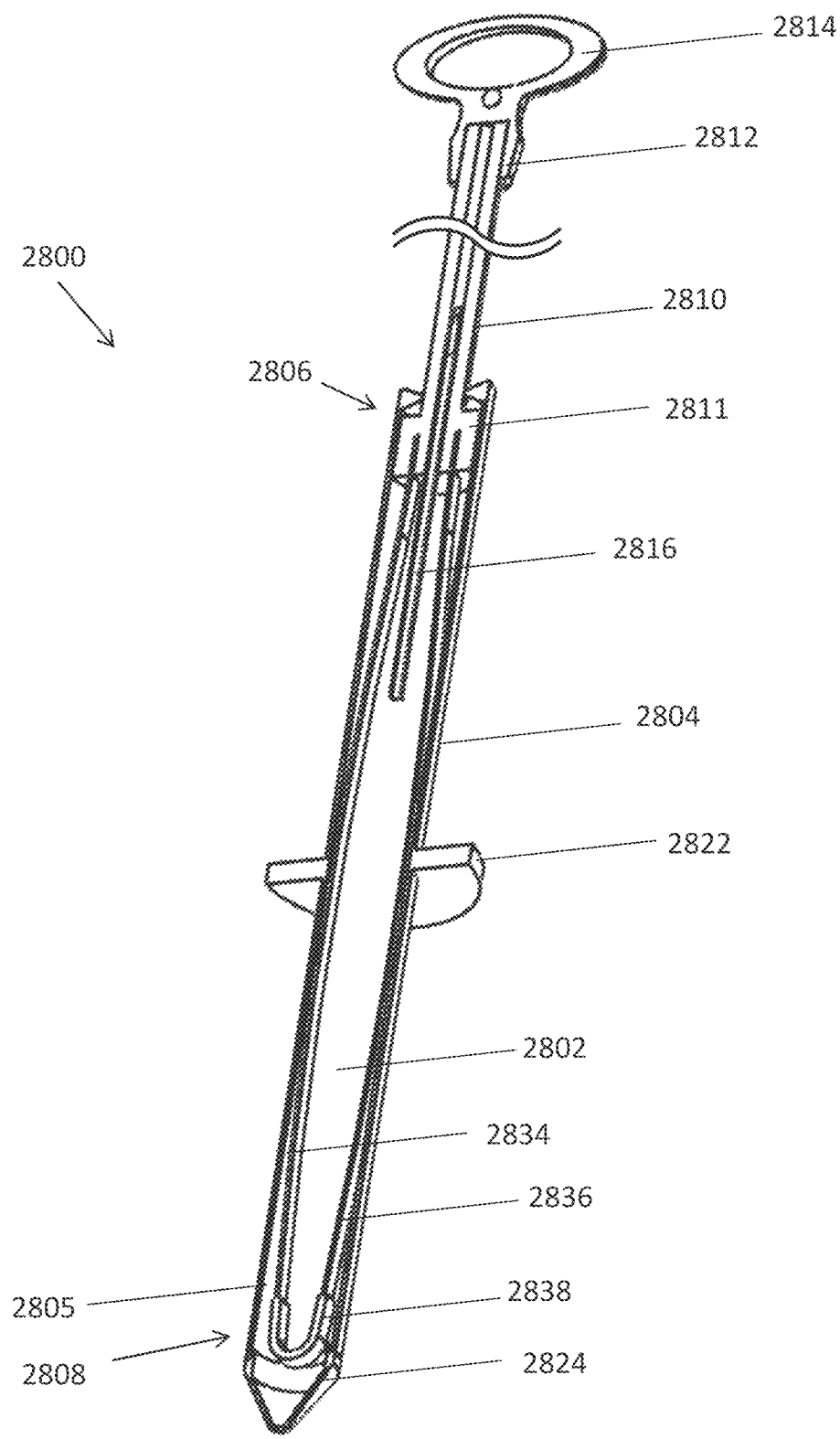
FIG. 28B is a simplified schematic section view of a deployment device, according to some embodiments of the invention.

FIG. 28B is a simplified schematic section view of a deployment device 2800, according to some embodiments of the invention.

Figure 28C:
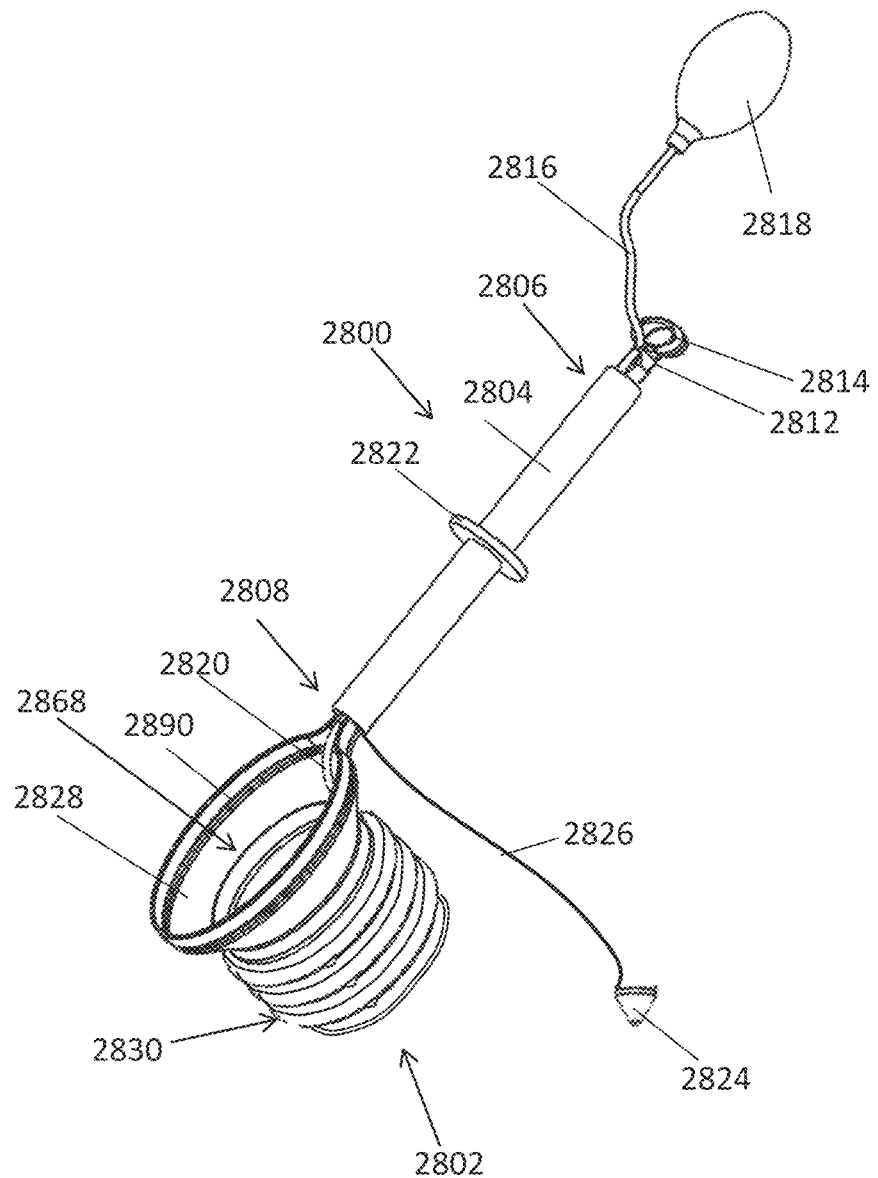
FIGS. 28C-D are simplified schematic perspective view of a deployment device, after extension of a workspace device, according to some embodiments of the invention.
Figure 28D:
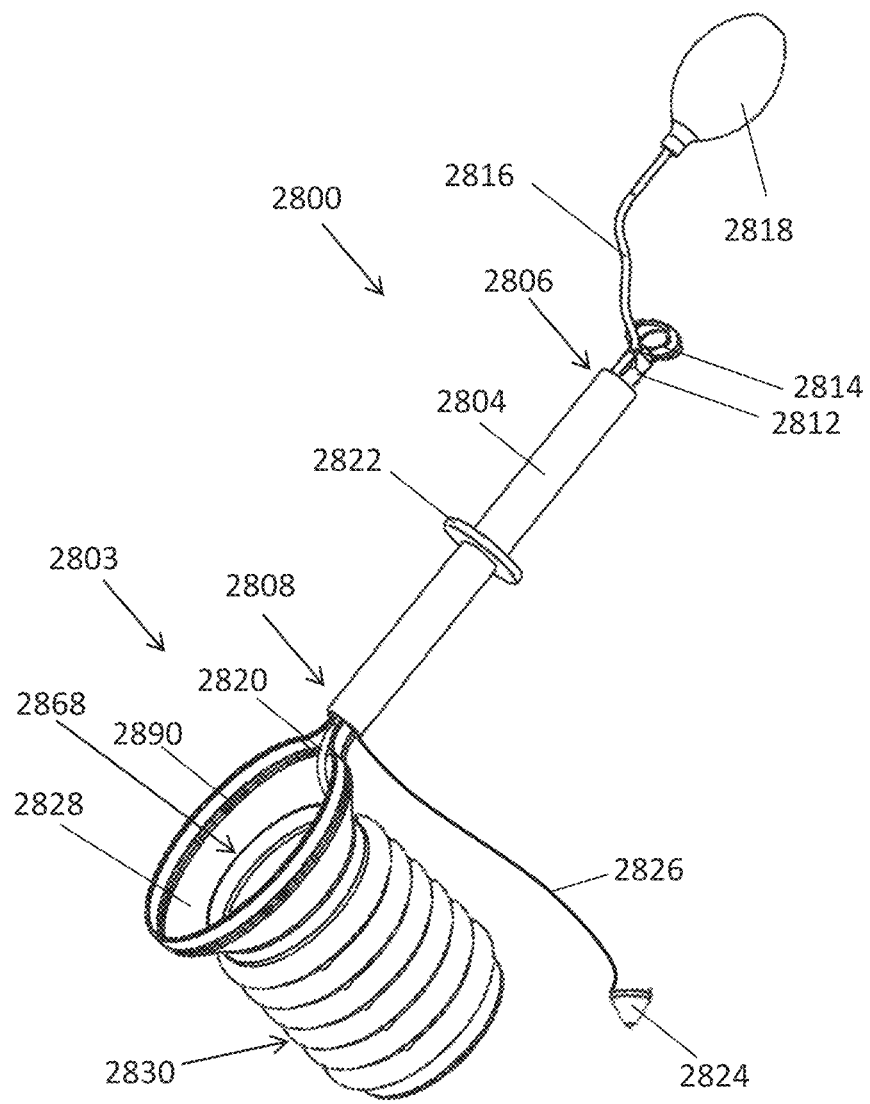

FIGS. 28C-D are simplified schematic perspective view of a deployment device 2800, after extension of a workspace device, according to some embodiments of the invention.

In some embodiments, FIG. 28C shows a partially inflated workspace device 2802 and FIG. 28D shows a fully inflated workspace device 2803. In some embodiments, the deployment devices of FIG. 28C and/or FIG. 28D are the same deployment device as illustrated in FIG. 28A and/or FIG. 28B.

In some embodiments, e.g. as described regarding step 2502 FIG. 25, the workspace circumferential segments 2830 are expanded sequentially, e.g. as illustrated in FIGS. 26A-C. Alternatively, e.g. as illustrated in FIGS. 28C-D, expansion of two or more (e.g. all) of the circumferential segments is simultaneous.

In some embodiments, a delivery device 2800 includes a delivery device body 2804.

Referring now to FIG. 28B, which, in some embodiments, is a sectional view of deployment device 2800 illustrated in FIG. 28A. In some embodiments, body 2804 includes a lumen 2805 which extends from a proximal end 2806 to a distal end 2808 of body 2804. In some embodiments, body 2800 is elongated. In some embodiments, body 2800 is tubular, for example, where one or more of an outer contour of body 2804 and an inner surface of the lumen within the body having circular cross section.

In some embodiments, a workspace device 2802 (e.g. in a collapsed configuration) is located within the lumen. In some embodiments, a cross sectional area of the collapsed device is 1 mm$^2$-10 cm$^2$, or 1 mm$^2$-5 cm$^2$, or 1 mm$^2$-3 cm$^2$ or 1 mm$^2$-2 cm$^2$, or 2 mm$^2$-2 cm$^2$, or lower or higher or intermediate ranges or areas. In some embodiments, a workspace device in a collapsed configuration is smaller in one direction or, in some embodiments, in more than one direction (e.g. axially and radially compressed) than the device in an expanded configuration. In some embodiments, delivery device 2800 includes a plunger 2810 which is sized and/or shaped to be inserted into the lumen of body 2803 displacing workspace device 2802 pushing it towards (e.g. through) a distal outlet of the delivery device body 2804.

In some embodiments, workspace device 2802 is folded and/or rolled to fit within the delivery device. In some embodiments, optionally after folding and/or rolling, the delivery device is subjected to a low pressure environment (e.g. vacuum packed and/or optionally restrained by additional element/s).

In some embodiments, material of the workspace device is selected to be thin enough and/or flexible enough so that the device can be fit into the delivery device body. In some embodiments, wall thickness (e.g. average wall thickness) of the device (when uninflated and/or a thickness of one wall of one or more inflatable segment) is 0.005-1 mm, or 0.01-1 mm, or 0.01-0.1 mm or lower or higher or intermediate thicknesses or ranges.

In some embodiments, a long axis length of plunger 2810 is as long as or is longer than that of body 2804, for example, so that when plunger 2810 is fully inserted into body 2804. In some embodiments, a cross sectional dimensions of plunger 2810 are sufficiently large with comparison to cross sectional dimensions of the lumen and/or of the collapsed workspace device so that when plunger 2810 is inserted into the lumen the collapsed workspace device is pushed out of the lumen.

In some embodiments, plunger 2810 includes a stopper 2412, which, in some embodiments, is sized to have one or more cross sectional dimension larger than that of the lumen of body 2804, which, in some embodiments, prevents plunger 2810 from being inserted into the lumen past the stopper. In some embodiments, stopper 2412 includes and/or is attached to a handle 2814, which, in some embodiments, the user holds to manipulate the plunger (e.g. insert and/or extract the plunger from the deployment device lumen). In some embodiments, handle 2814 includes a finger loop, which, in some embodiments, is sized and/or shaped for a human adult user to insert one or more finger into. In some embodiments, handle 2814 includes more than one finger loop, e.g. two finger loops, three finger loops (e.g. as illustrated on handle 2718 FIGS. 27A-F), four finger loops.

Referring back now to FIG. 28A, in some embodiments, delivery device 2800 includes a connector 2816 for one or more inflation device 2818. In some embodiments, connector 2816 includes a tube 2816 (and/or a connector to the tube) which tube is fluidly connected to a tube 2820 fluidly connected to the workspace device 2802, where, for example, fluid inserted into tube 2816 travels to tube 2820 and then, in some embodiments, to inflatable chamber/s 2822 of workspace device 2803. In some embodiments, tubes 2816, 2820 are a single tube extending from inflation device 2818 through the lumen of body 2804 to workspace device 2803. For example, referring now to FIG. 28B, in some embodiments, tube 2816 extends from a coupling to plunger 2810 through to workspace device 2802. In some embodiments, tube 2816 is supported by a plunger head 2811. Alternatively or additionally, in some embodiments, plunger head 2811 provides coupling and/or attachment between portion/s of workspace device 2802 and plunger 2810.

Referring back to FIG. 28A. In some embodiments, inflation device 2818 is a hand pump (e.g. hand-air pump) including, for example, a compressible air pouch 2818 and a one-way valve connecting the air pouch to tube 2816 (and e.g. letting air into tube 2816 and not out of tube 2816) and, in some embodiments, a second one-way valve, allowing air into the pouch but not out of the pouch.

Alternatively or additionally, in some embodiments, inflation device is a liquid hand pump e.g. including a liquid filled compressible pouch 2818. Alternatively or additionally, in some embodiments, inflation device 2818 includes a fluid (e.g. liquid) filled syringe.

In some embodiments, body 2804 includes one or more stopper 2822. In some embodiments, stopper 2822 extends in a direction perpendicular to a long axis of body 2804. In some embodiments, stopper 2822 is sized and/or shaped to prevent body 2804 from being inserted into a patient beyond stopper 2822. In some embodiments, a longitudinal position of stopper 2822 on body is adjustable (e.g. stopper including a lock which is configured to lock stopper 2822 onto body 2804 at a plurality of positions). A potential benefit of an adjustable position of stopper is the ability to insert delivery device is the ability to tailor depth of insertion for a particular patient and/or surgical site within a patient e.g. deeper, e.g. for access to a deeper surgical site, e.g. for larger and/or obese patients. In some embodiments, stopper 2822 is sized and/or shaped to make a seal with patient tissue, e.g. preventing escape of insufflation gas from the cavity through the incision through which body 2804 is inserted. Alternatively or additionally, in some embodiments, deployment device 2800 includes additional sealing device/s.

In some embodiments, deployment device 2800 includes a tip 2824. In some embodiments, tip 2824 has a tapered shape, where, for example, in some embodiments, tip 2824 tapers in a distal direction. In some embodiments, deployment device 2800 is inserted through an incision, a tapered tip 2824 eases insertion of the deployment device, e.g. through a small incision a potential benefit being a good seal between patient tissue and the deployment device. In some embodiments, tip 2824 is sufficiently rigid and/or sharp (e.g. in some embodiments, tip includes a sharpened edge and/or point e.g. includes a blade), that, in some embodiments, the deployment device is used to make the incision.

Referring now to FIGS. 28C-D. In some embodiments, tip 2824 is attached to body 2804 of deployment device 2800 e.g. by an elongated element 2826 (e.g. a string). In some embodiments, elongated element 2826 is attached to body 2804. Alternatively or additionally, in some embodiments, elongated element is attached to plunger 2810. Alternatively or additionally, in some embodiments, tip 2824 is attached to body 2804 by another attachment means, for example, in some embodiments, tip 2824 is hingedly attached to a distal end of body 2840.

In some embodiments, workspace device 2802 includes a rim portion 2828. For example, in some embodiments, rim portion 2828 includes flexible material which, in some embodiments, is reinforced by reinforcement 2890. In some embodiments, the reinforced material makes a ring. In some embodiments, the reinforcement is elastically compressed to fit within the lumen of body 2804. In some embodiments, rim portion 2828 is connected to plunger 2810 (e.g. a distal end of plunger 2810). In an exemplary embodiment, the reinforcement includes a first and a second elongated element 2834, 2836, which are connected at a distal end by a connector 2838. In some embodiments, connector 2838 is elastically compressed within the deployment device lumen. Exemplary materials for connector 2838 include metal (e.g. stainless steel e.g. crimped around and/or welded to elongated elements 2834, 2836) and/or plastic. In some embodiments, first and second elongated elements are a single component, for example, an arc or ring of material which is e.g. elastically compressed within the delivery device lumen. In some embodiments, elongated elements 2834, 2836 are coupled to plunger head 2811, for example, glued and/or welded and/or crimped and/or pinned (e.g. by one or more metal and/or plastic pin). In some embodiments, one or both of elongated elements are stainless steel.

In some embodiments, rim is pulled through an opening in the patient wall (e.g. abdominal wall), for example as illustrated in FIG. 27F, the flexible material of rim, in some embodiments, conforming and/or being pinched by the patient wall opening. In some embodiments, the rim is expandable, for example, by unfolding and/or unrolling. A potential benefit being the ability to leave the body of the workspace in situ while extracting an opening (e.g. opening 2768 FIG. 27F, 2868 FIGS. 28C-D) of the workspace device e.g. to outside of the patient.

In some embodiments, the flexible material of rim portion 2828 is attached to or is part of a double sheet of material which forms the body of the workspace device including inflatable chambers 2830.

In some embodiments, reinforced rim portion 2828 is attached to a body 2830 of workspace device 2802, 2803 where, in some embodiments, body 2830 includes a plurality of inflatable compartments, where, the workspace device includes one or more feature as illustrated and/or described regarding one or more of workspaces 2902 FIGS. 29A-B, 3002 FIG. 30, 3102 FIG. 31, 3203 FIGS. 32A-B, 3302 FIGS. 33A-C, 3402 FIGS. 34A-C, 3502 FIG. 35, 3602 FIGS. 36A-B, 3702 FIG. 37, 3802 FIG. 38, 3902 FIG. 39.

Figure 29A:
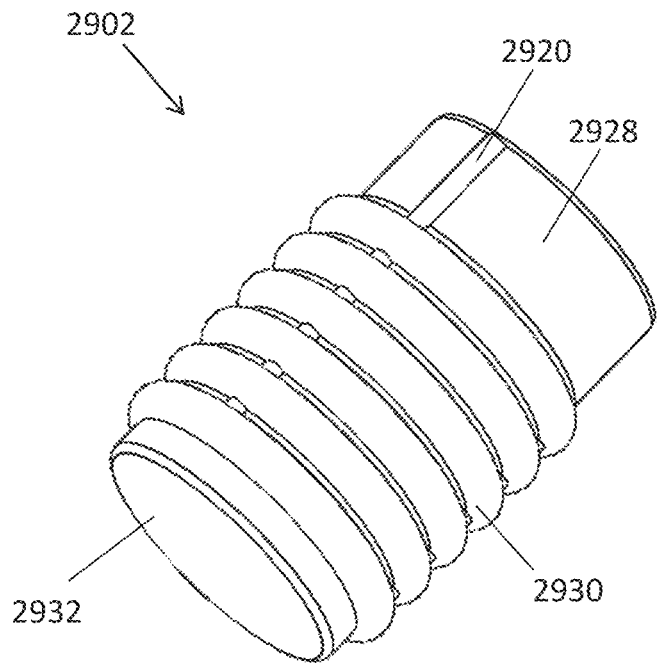
FIG. 29A is a simplified schematic perspective view of a workspace device, according to some embodiments of the invention.

FIG. 29A is a simplified schematic perspective view of a workspace device 2900, according to some embodiments of the invention.

Figure 29B:
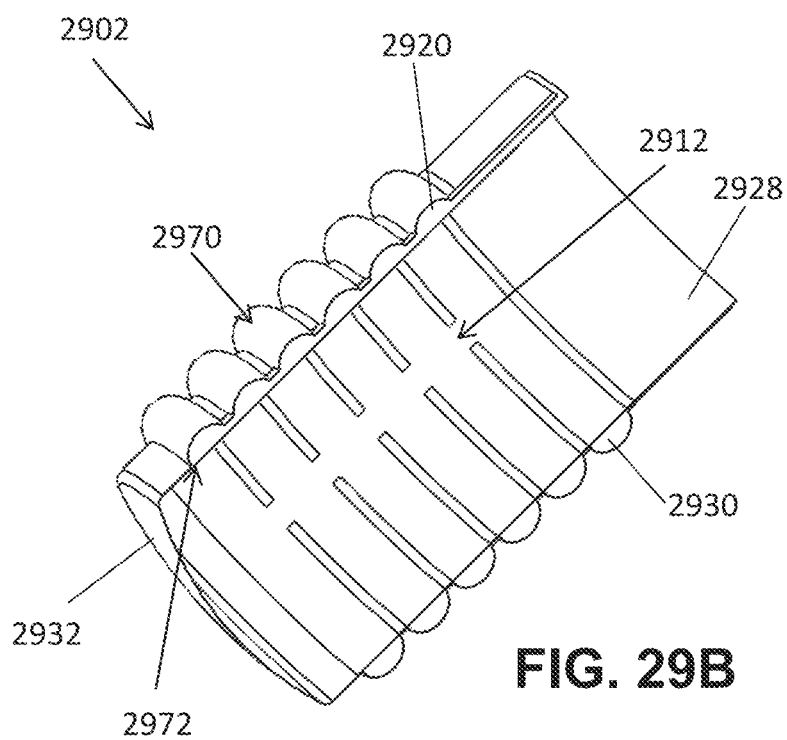
FIG. 29B is a simplified schematic section view of a workspace device, according to some embodiments of the invention.

FIG. 29B is a simplified schematic section view of a workspace device 2900, according to some embodiments of the invention.

In some embodiments, FIG. 29B illustrates a section view of the workspace illustrated in FIG. 29A.

In some embodiments, workspace 2900 includes a plurality of inflatable compartments 2902. In some embodiments, one or more of compartments 2902 (e.g. all of compartments 2902) are ring-shaped. In some embodiments, when inflated (e.g. as illustrated in FIGS. 28C, 29A-B) the compartments press against each other, which, in some embodiments, makes workspace walls which are sufficiently rigid to withstand pressures of an insufflated patient cavity. In some embodiments, the inflated compartments provide rigidity against radial and/or axial forces acting on the workspace.

For example, in some embodiments, to withstand a 17 mmHg pressure in a cavity (e.g. insufflated abdominal cavity) a workspace with an inner diameter of about 100 mm has toroidal shaped compartments where a torus cross sectional diameter is 10 mm (in some embodiments, a largest cross sectional of a segment is 1-30 mm, or 5-25 mm, or 5-15 mm, or lower or higher or intermediate sizes or ranges and the compartments are inflated to an internal pressure of 100-200 mmHg.

In some embodiments, an inner diameter and/or a maximum and/or average cross sectional (perpendicular to a long axis) of a workspace inner lumen is 10-500 mm, or 50-200 mm, or 50-150 mm, or lower or higher or intermediate sizes or ranges. In some embodiments, a range of size workspace devices are provided, each workspace device designated for a different organ and/or procedure and/or patient (e.g. adult, child, obese, underweight).

Generally, the cross sectional area of circumferential segments (e.g. ring shaped chambers) is dependent on the elasticity of the material of the workspace device, the material thickness, the hardness of the material where higher elasticity means that the chambers may be inflated with lower pressure to achieve the same rigidity.

In some embodiments, workspace device 2902 is constructed from a double tubular sheet of material. In some embodiments, the double sheets are connected at portions (e.g. by glue and/or heat and/or pressure treatment) to make the inflatable compartments 2930. In some embodiments, one or both of the sheets are flat sheets. In some embodiments, one or both of the sheets are shaped. For example, in the embodiment illustrated in FIG. 29B, inner sheet 2972 is planar, having a smooth generally cylindrical shape and outer sheet 2970 is shaped to provide a curved outer shape to the rings 2930. In some embodiments, the workspace is constructed from a single tubular sheath which is folded inside itself to form the double layer.

In some embodiments, a passageway fluidly connects the compartments, the passageway, in some embodiments, fluidly connected to passageway 2920 for inflation of the workspace device. Alternatively, in some embodiments, a separate tube structure is connected to the workspace device. In some embodiments, passageway 2920 is formed by connections of the double sheet. In some embodiments, workspace device 2902 includes more than one inflation tube and/or passageway and/or channel (e.g. 2912 FIG. 29B indicates a region where the circumferential segments are not connected forming a passageway). In some embodiments, passageways are fluidly connected and, for example, are filled by a single tube extending from the device. Alternatively, in some embodiments, more than one tube extending from the workspace device fluidly connects to one or more passageway.

In some embodiments, the channels are fluidly connected and, for example, supplied with inflation fluid by a single supply channel extending to the workspace e.g. from outside the patient. Alternatively, one or more channel has a separate supply channel. In some embodiments, there is one or more valve within the workspace channel/s and/or segments, e.g. to control flow of inflation fluid. In some embodiments, workspace device includes a rim 2928, which in some embodiments, is not inflatable. In some embodiments, rim 2928 is reinforced (e.g. including one or more feature as illustrated and/or described regarding rim portion 2828 FIGS. 28C-D).

In some embodiments workspace device includes a base 2932. In some embodiments, base includes a double layer of material, for example, a double layer of sheet material e.g. the same sheet material from which inner and outer surfaces 2972, 2970 are made. In some embodiments, base 2932 is reinforce, for example, by one or more of; made using additional layer/s, including reinforcing material, e.g. reinforcing elements, e.g. sheet/s reinforced with fibers. For example, in some embodiments, in inner surface and the outer surface are constructed from TPU (thermoplastic polyurethane) and/or another plastic and/or polymer known in the art of inflatable structures, where the base portion includes reinforcing fibers, e.g. nylon fiber reinforcement.

In some embodiments, base 2932 is reinforced by inflation, for example including one or more inflatable chamber.

In some embodiments, base 2932 is compressed and/or folded and/or rolled (e.g. to fit through the opening in the patient, e.g. to fit through laparoscopic opening, e.g. to fit through a lumen of a delivery device). In some embodiments, base 2932 is elastically compressed (e.g. to fit), for example, expanding by elastic relaxation upon deployment within the patient cavity.

A potential benefit of a reinforced base is reduced risk of puncture of the workspace device as, in some embodiments, morcellization (e.g. with a morcellator grasper) and/or manipulation (e.g. using one or more grasper) and/or treatment of tissue within the workspace applies forces on the workspace in a direction towards the base.

Figure 30:
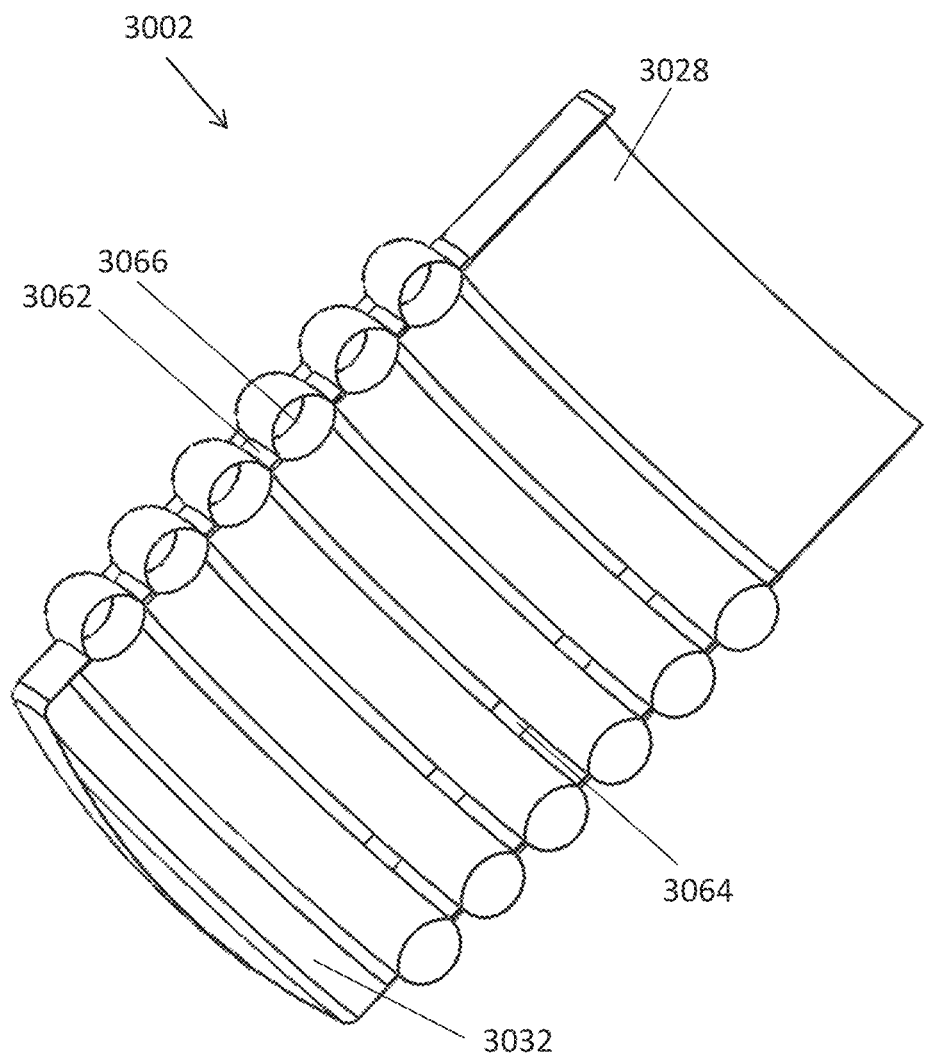
FIG. 30 is a simplified schematic section view of a workspace device, according to some embodiments of the invention.

FIG. 30 is a simplified schematic section view of a workspace device 3002, according to some embodiments of the invention.

In some embodiments, FIG. 30 illustrates a sectional view of workspace device 2902 FIG. 29A. In the embodiment illustrated by FIG. 30, both an inner surface and an outer surface of the workspace device are shaped. In some embodiments, a cross section 3066 of one or more of the circumferential chambers is circular, one or more compartments (e.g. all compartments) having a torus shaped when inflated.

In some embodiments, shaped workspace surfaces are manufactured by molding. For example, by one or more of inflation molding, vacuum, molding and dip molding where, for example, a sheet of material is manufactured so that the sheet is shaped when relaxed e.g. not inflated and/or compressed.

In some embodiments, circumferential inflatable compartments press against each other in an axial direction e.g. direction of extension of the workspace device e.g. as illustrated in FIGS. 26B-C. Alternatively, in some embodiments, one or more compartment is separated from one or more adjacent compartment by a membrane 3062. It is to be understood that embodiments illustrated in this application including separating membranes may be adjusted to lack these membranes and/or have thin membranes, such that when the workspace device is expanded the inflatable compartments press against each other e.g. in an axial direction e.g. in a direction of expansion of the workspace device.

In some embodiments, workspace device includes a rim 3028, which in some embodiments, is not inflatable. In some embodiments, rim 3028 is reinforced (e.g. including one or more feature as illustrated and/or described regarding rim portion 2828 FIGS. 28C-D).

Figure 31:
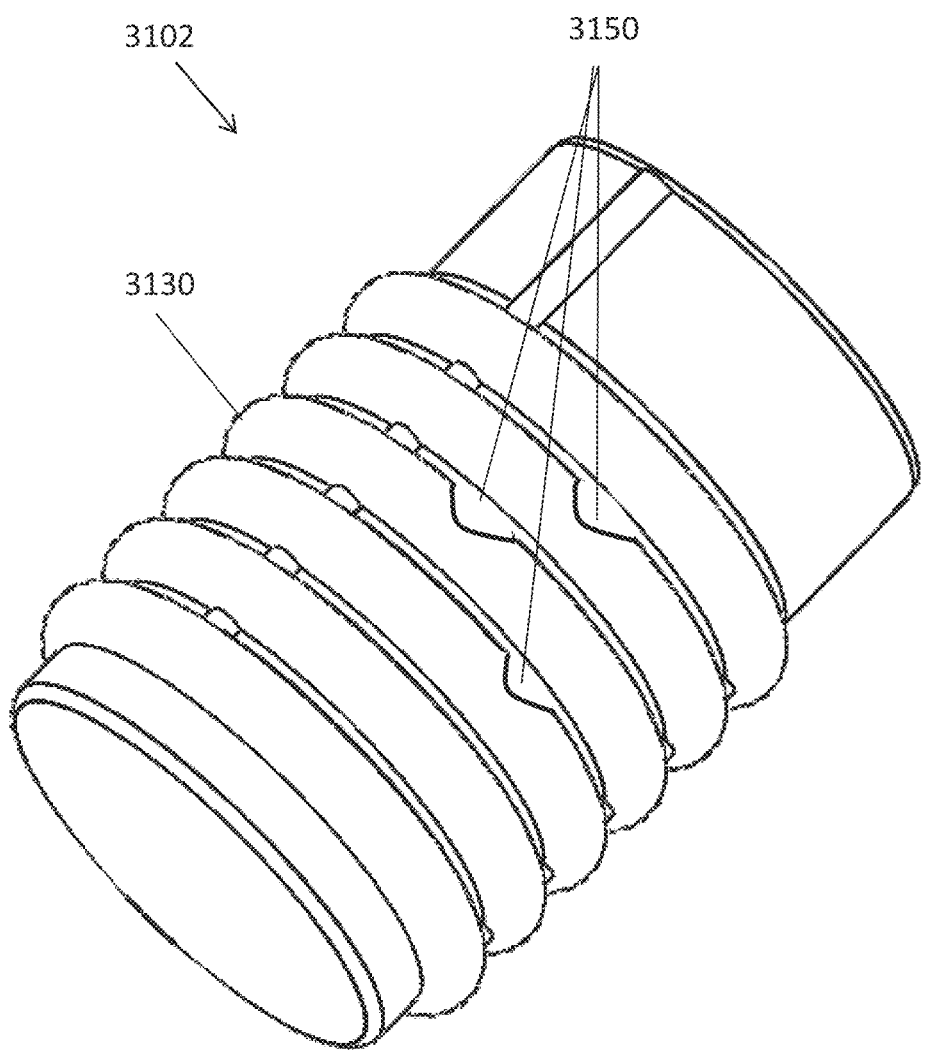
FIG. 31 is a simplified schematic perspective view of a workspace including windows, according to some embodiments of the invention.

FIG. 31 is a simplified schematic perspective view of a workspace including windows 3150, according to some embodiments of the invention.

In some embodiments, one or more circumferential chamber 3130 has a varying cross section. In some embodiments, reduced cross section (e.g. in an axial direction) at point/s makes gaps 3150 which form windows in the workspace device. A potential advantage being visualization of tissue outside the workspace device from inside the device. It is to be understood that, in some embodiments, each embodiment described in this document includes one or more window. In some embodiments, windows between circumferential chambers are bridged by a membrane (e.g. the double layer sheet connected at this point). Alternatively, in some embodiments, the windows are gaps, and the workspace device is used within an outer sheath which provides containment.

In some embodiments, gaps 3150 are small with respect to a surface are of the workspace device, for example, gaps 3150 (and/or windows) forming 1-40%, or 1-30%, or 1-20%, or lower or higher or intermediate ranges or percentages of a surface area of the walls of the workspace device (the percentage, in some embodiments, excluding the area of the base and/or opening). A potential benefit being maintained structural strength of the workspace device.

In some embodiments, a ring (e.g. each ring) contacts adjacent ring/s (between the window regions) for 10-95%, or 20-95%, or 30-80%, or lower or higher or intermediate ranges or percentages.

In some embodiments there is at least three contact areas between a ring (e.g. each ring) between the ring and adjacent ring/s.

Figure 32A:
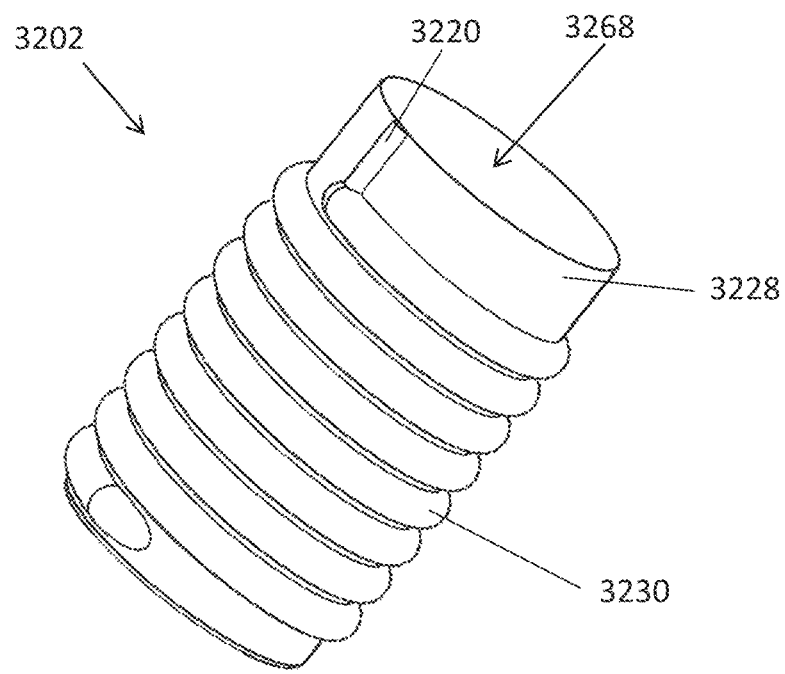
FIG. 32A is a simplified schematic perspective view of a workspace device 3202, according to some embodiments of the invention.

FIG. 32A is a simplified schematic perspective view of a workspace device 3202, according to some embodiments of the invention.

Figure 32B:
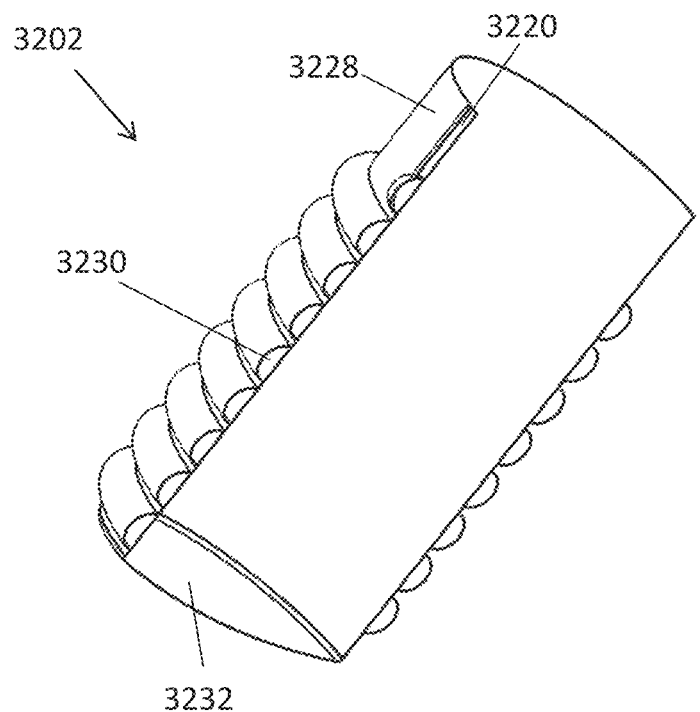
FIG. 32B is a simplified schematic section view of a workspace device, according to some embodiments of the invention.

FIG. 32B is a simplified schematic section view of a workspace device 3202, according to some embodiments of the invention.

In some embodiments, workspace device 3202 includes a single inflatable chamber which has a plurality of circumferential portions (also herein termed segments). In some embodiments, chamber 3230 is inflated through a channel 3220 fluidly coupled to a top of the workspace device (top being adjacent to a rim 3228 and/or opening 3258 of the device), the chamber in some embodiments, inflating from the top of the device downwards, inflating circumferential portions of the chamber in a downwards direction sequentially. Alternatively, in some embodiments, channel 3220 is fluidly coupled to a different portion of the chamber, inflating that portion first and then other adjacent regions sequentially.

In some embodiments, workspace device 3202 is formed from an inner tubular sheet which is connected, at portions to an outer tubular sheet.

Alternatively, in some embodiments, manufacture includes construction of one or more chamber which is then connected to itself. For example, in some embodiments, a single chamber is connected to itself, for example, an elongate chamber is wound and connected to form the helical chamber e.g. of FIGS. 32A-B.

Figure 33A:
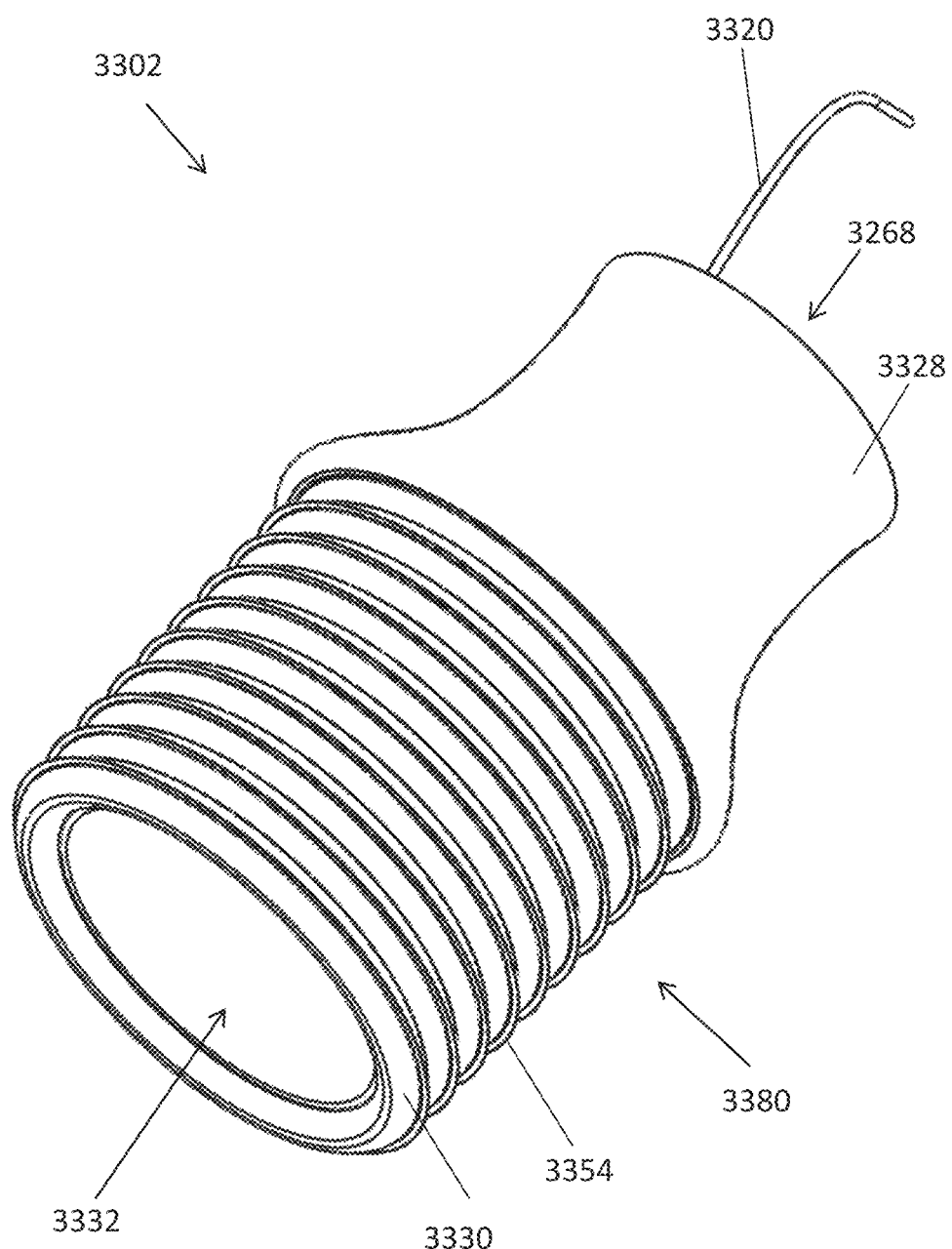
FIG. 33A is a simplified schematic perspective view of a workspace device, according to some embodiments of the invention.

FIG. 33A is a simplified schematic perspective view of a workspace device 3302, according to some embodiments of the invention.

Figure 33B:
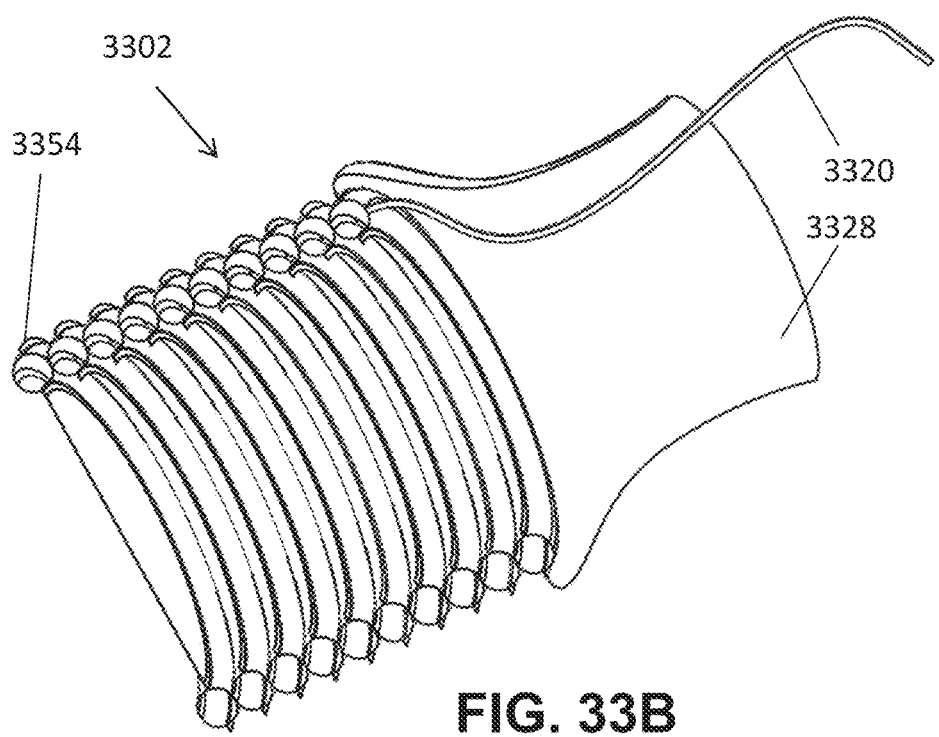
FIG. 33B is a simplified schematic section view of a workspace device, according to some embodiments of the invention.

FIG. 33B is a simplified schematic section view of a workspace device 3302, according to some embodiments of the invention.

Figure 33C:
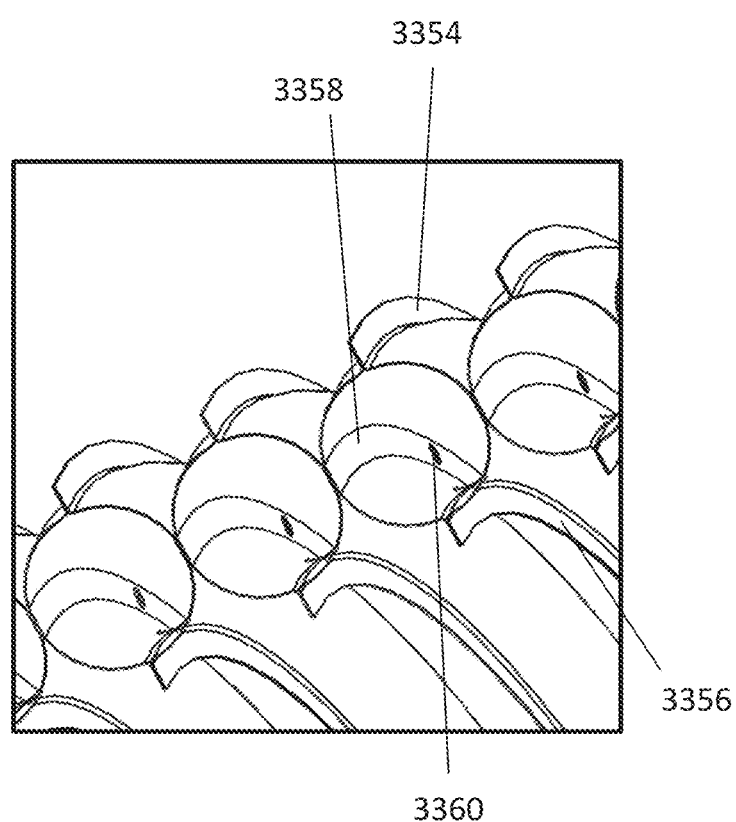
FIG. 33C is a zoomed in portion of FIG. 33B, according to some embodiments of the invention.

FIG. 33C is a zoomed in portion of FIG. 33B, according to some embodiments of the invention.

In some embodiments, workspace device 3302 has rim 3328 with a tapered shape where the rim tapers from connection to a body 3380 of the workspace device in a direction towards an opening 3268 of the workspace device. A potential benefit of a tapered rim is ease of pulling the rim portion through an opening in the patient and/or inserting a morscellator through the rim portion at the patient opening.

In some embodiments, one or more tube 3320 which provides fluid for inflation of the workspace device chambers 3330 is a separate element (e.g. as opposed to being a chamber defined by double walls of the workspace device e.g. as illustrated in FIGS. 29A-B, 30).

In some embodiments, the workspace device includes one or more reinforcement, for example, on a body of the device. In some embodiments, one or more circumferential inflatable portion includes a reinforcing fin 3354. In some embodiments, each ring shaped inflatable chamber includes a fin located on an outside surface of the inflatable portion.

In some embodiments, a workspace device is manufactured by constructing the inflatable chambers and then connecting the chambers. For example, in some embodiments, a plurality of rings are first constructed e.g. by joining edges of two ring-shaped sheets of material (e.g. the joined edges, in some embodiments, forming fins e.g. fin 3354). In some embodiments, the chambers are connected by one or more of welding (e.g. one or more of heat welding, RF welding, ultrasonic welding, laser welding) adhering by application of glue and/or solvent. In some embodiments, channel/s between the chambers (e.g. holes 3360) are made before the chambers are connected. Referring now to FIG. 33C, in some embodiments, one or more circumferential inflatable portion includes a reinforcing fin 3360 located on an inside surface of the inflatable portion (the inside surface, in some embodiments, being the surface of the lumen of the workspace device).

A potential benefit of fins and/or other elements which extend from an inner surface of the inflatable portions of the wall into the inner lumen of the workspace is that collisions between instrument/s (e.g. a morcellator) and the workspace device may be cushioned by the fins and/or elements and/or prevent and/or reduce contact between inflatable portion/s and the associated risk of rupture.

In some embodiments, holes 3360 between inflatable chambers allow inflation fluid to pass from one chamber to adjacent chamber/s.

Figure 33D:
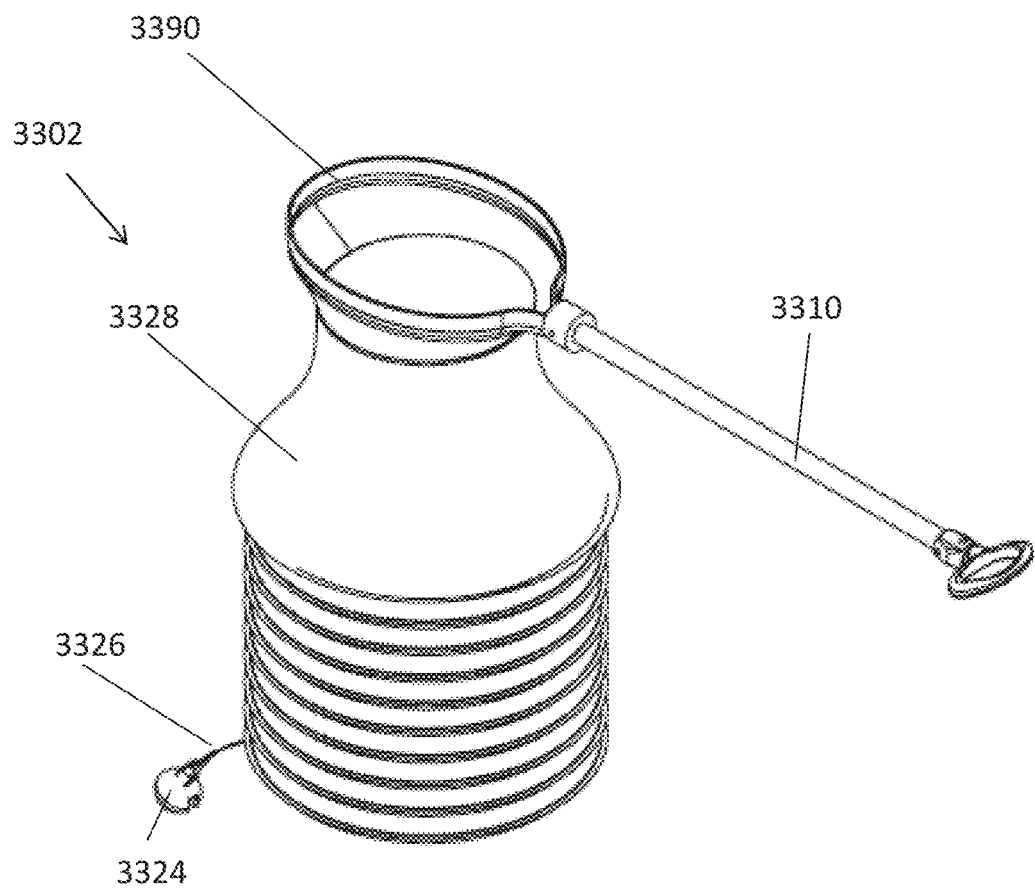
FIG. 33D is a simplified schematic perspective view of a workspace device connected to a deployment handle, according to some embodiments of the invention.

FIG. 33D is a simplified schematic perspective view of a workspace device 3302 connected to a deployment handle 3310 (also herein termed "plunger"), according to some embodiments of the invention.

Figure 34A:
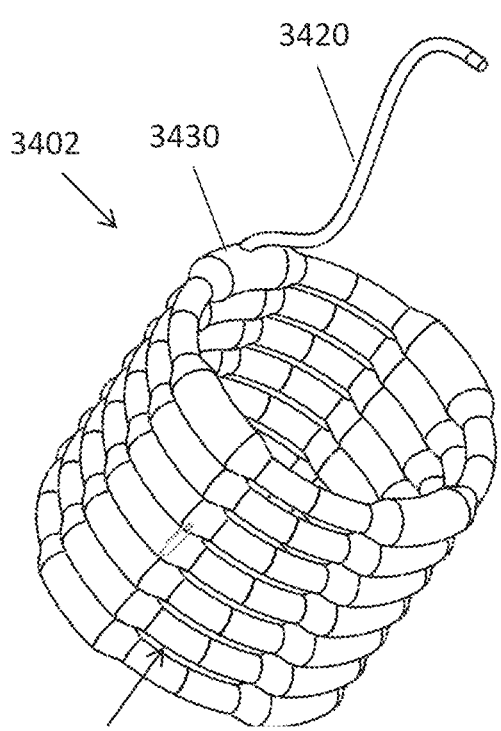
FIGS. 34A-B are simplified schematic perspective view of a workspace device, according to some embodiments of the invention.
Figure 34B:
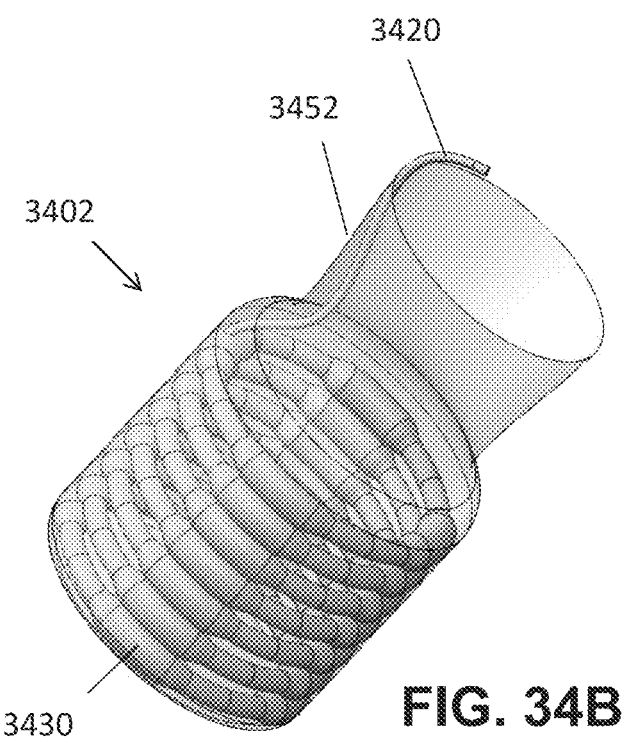

FIGS. 34A-B are simplified schematic perspective view of a workspace device 3400, according to some embodiments of the invention.

Figure 34C:
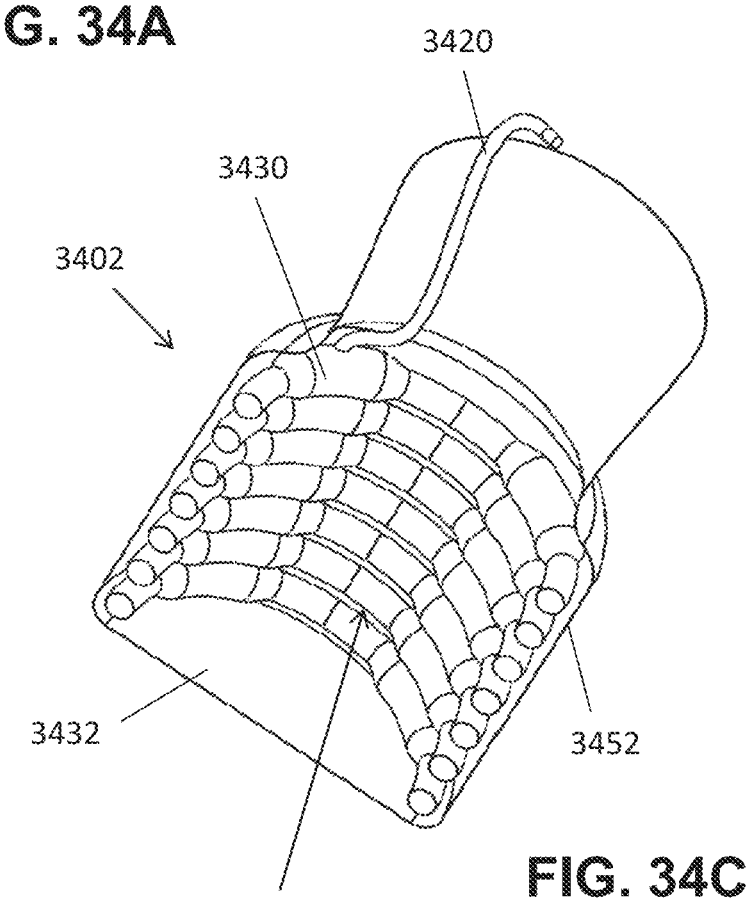
FIG. 34C is a simplified schematic section view of a workspace device, according to some embodiments of the invention.

FIG. 34C is a simplified schematic section view of a workspace device 3400, according to some embodiments of the invention.

In some embodiments, workspace device 3400 includes a plurality of circumferential inflatable chambers 3430 where, at one or more portion of the circumference of the chambers the chambers contact each other. In some embodiments, the more than one circumferential portion is in contact, for example, 2-10, or, in an exemplary embodiment 4 portions. In some embodiments, regions of the inflatable chambers between the contacting portions have smaller cross sectional dimension, in at least one dimension and, in an exemplary embodiment, have a smaller diameter circular cross section leaving gaps 3450 between the inflatable chambers (e.g. forming windows in the workspace device). In some embodiments, 10-90%, or 30-90%, or 30-80% or lower or higher or intermediate ranges or percentages of a circumferential length of one or more (or of all) of the inflatable circumferential segments are in contact, at least when inflated.

As described, previously, in some embodiments, an outer sheath 3452 covers the device. In some embodiments, the inflatable parts are not connected to a base, the sheath 3452 forming a base 3432 to the device, potentially providing a large window for the user to view the patient cavity through from the lumen of the workspace device.

Figure 35:
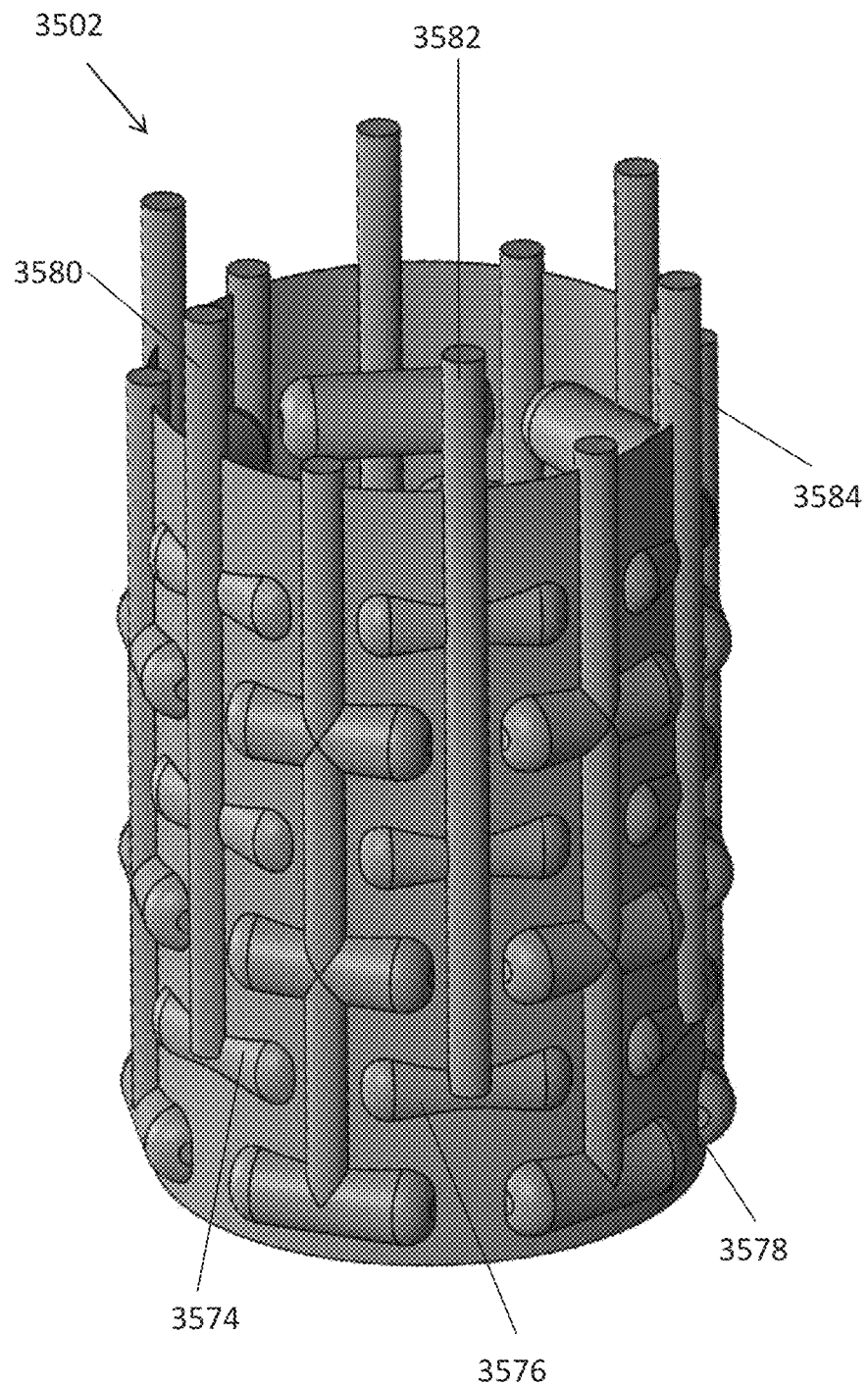
FIG. 35 is a simplified schematic perspective view of a workspace device, according to some embodiments of the invention.

FIG. 35 is a simplified schematic perspective view of a workspace device 3502, according to some embodiments of the invention.

In some embodiments, one or more circumferential portion of the workspace includes a plurality of inflatable circumferential segments 3574, 3576, 3578 which, in some embodiments, are not fluidly connected, e.g. are not directly fluidly connected. In some embodiments, one or more circumferential segment is inflated through a different channel. For example, in an exemplary embodiment, segments 3574, 3576, 3578 are inflated by channels 3580, 3582, 3584 respectively. In some embodiments, one or more channel itself is an inflatable segment.

In some embodiments, once inflated, the circumferential segments push up against other inflated portion/s (e.g. other segment/s and/or channel/s) e.g. to rigidize the workspace device.

In some embodiments, circumferential segments do not push up against each other but are separated by a connecting portion of material, in some embodiments, tension on the connecting portion rigidifies the structure.

In some embodiments, a plurality of axial channels each fill a plurality of circumferential chambers branching from the channel. In some embodiments, there are 2-20 axial channels, or 2-15, or 2-10, or lower or higher or intermediate rages or numbers of axial channels. In some embodiments, the axial channels are equally spaced circumferentially on a tubular (e.g. generally cylindrical) shaped workspace.

A potential benefit of segments for a single circumferential area of the workspace being filled by different channels is that, if a channel fails and/or segment of the channel fails (e.g. ruptures, fails to inflate) the structure maintains a proportion of circumferential strength and/or rigidity.

In some embodiments, the channels are fluidly connected and, for example, supplied with inflation fluid by a single supply channel extending to the workspace e.g. from outside the patient. Alternatively, one or more channel has a separate supply channel. In some embodiments, there is one or more valve within the workspace channel/s and/or segments, e.g. to control flow of inflation fluid.

Figure 36A:
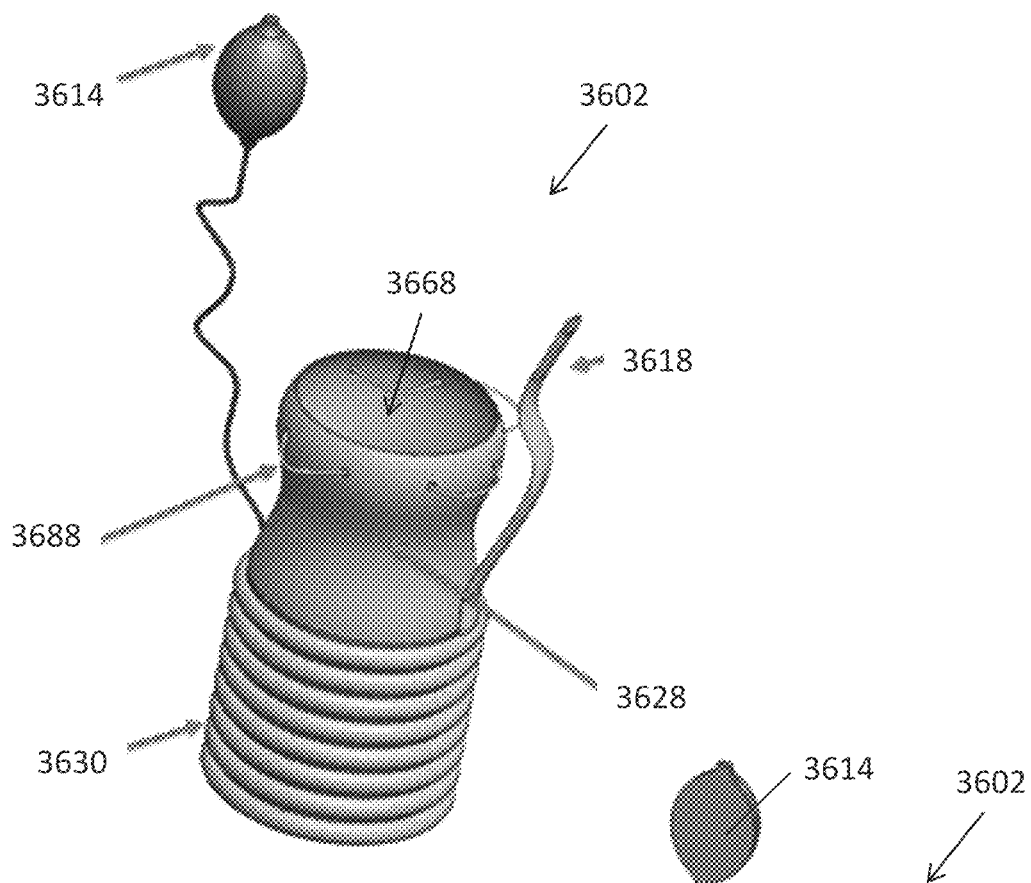
FIG. 36A is a simplified schematic perspective view of a workspace device, according to some embodiments of the invention.

FIG. 36A is a simplified schematic perspective view of a workspace device 3600, according to some embodiments of the invention.

Figure 36B:
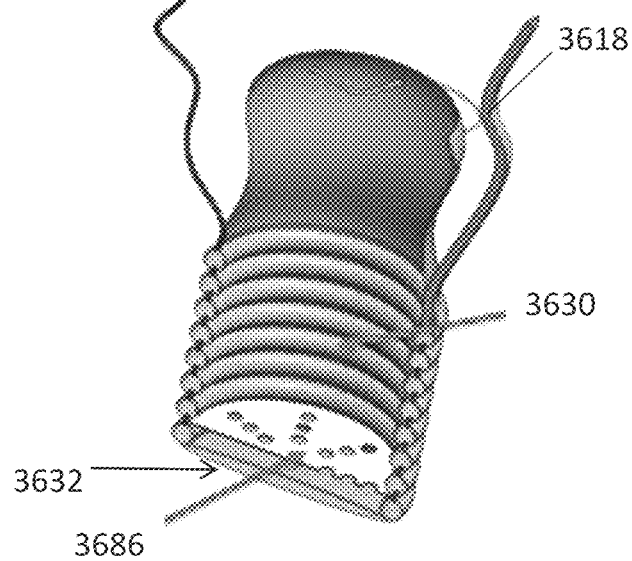
FIG. 36B is a simplified schematic sectional view of a workspace device, according to some embodiments of the invention.

FIG. 36B is a simplified schematic sectional view of a workspace device 3600, according to some embodiments of the invention.

In some embodiments, a workspace device includes a sieve 3686. Where, in some embodiments, sieve 3686 forms part of a second lumen wall where the second lumen is smaller than a total workspace lumen. In some embodiments, sieve 3686 is a portion which is connected to, within workspace 3602, workspace inner walls along a continuous circumferential path on the workspace walls. In some embodiments, sieve 3868 includes holes which are sized and/or shaped to allow tissue under a certain size to pass through the sieve and be contained e.g. by a base 3632 of the workspace device. In some embodiments, holes of the sieve are sized to allow tissue parts small enough to be removed within the workspace device through a laparoscopic incision. In some embodiments, a hole cross sectional area is 0.5-20 $mm^2$, or 0.5-10 $mm^2$, or 0.5-5 $mm^2$, or lower or higher or intermediate ranges or areas.

In some embodiments, a user pulls on a handle 3618 to extract workspace device 3602 is from the cavity (for example, an opening 3668 of the workspace device, e.g. before insertion of a morcellator and/or after treatment when the whole workspace device is removed). In some embodiments, handle 3618 is a flexible tape.

In some embodiments, for example, before extraction of opening 3668, the opening is at least partially closed, for example, by tensioning an elongated element 3688 coupled to a top of a rim portion 3628 of the workspace device. In some embodiments, elongated element is threaded through holes around the circumference of rim portion 3628. In some embodiments, elongated element 3688 is tensioned by tensioning handle 3618 which, in some embodiments, is coupled to elongated element 2588. In some embodiments, elongated element includes a string and/or cable and/or tape.

Figure 37:
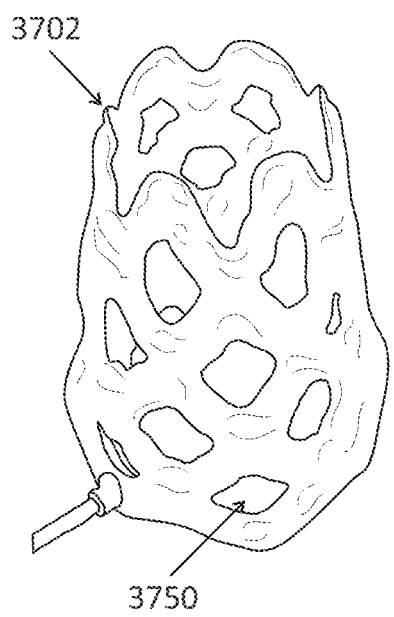
FIG. 37 is a simplified schematic perspective view of a workspace device, according to some embodiments of the invention.

FIG. 37 is a simplified schematic perspective view of a workspace device, according to some embodiments of the invention.

Figure 38:
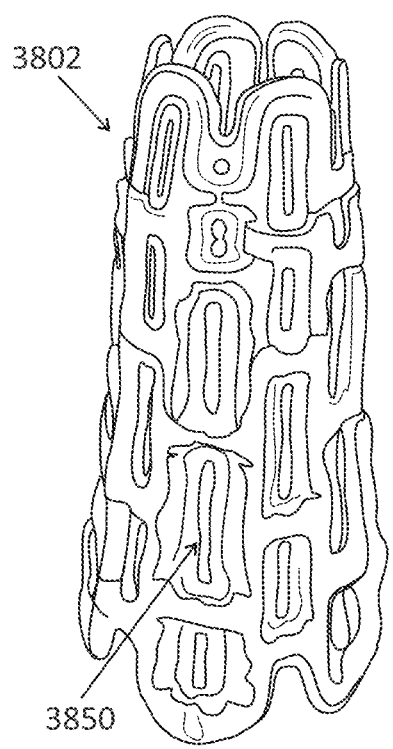
FIG. 38 is a simplified schematic perspective view of a workspace device, according to some embodiments of the invention.

FIG. 38 is a simplified schematic perspective view of a workspace device, according to some embodiments of the invention.

In some embodiments, FIG. 38 illustrates a workspace which includes inflatable segments which are orientated axially and inflatable segments which are orientated circumferentially.

Figure 39:
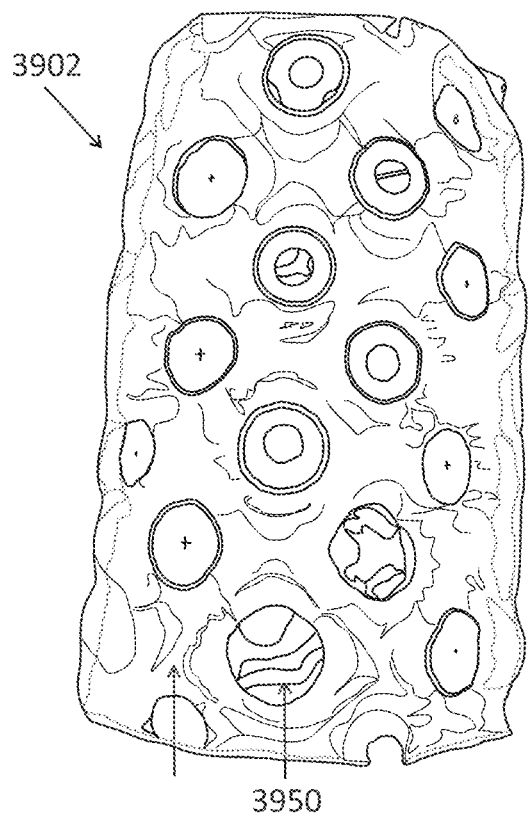
FIG. 39 is a simplified schematic perspective view of a workspace device, according to some embodiments of the invention.

FIG. 39 is a simplified schematic perspective view of a workspace device, according to some embodiments of the invention.

In some embodiments, workspace devices 3702, 3802, 3902, each include a plurality of circumferential windows 3750, 3850, 3950 respectively, between inflatable segments. In some embodiments, the windows are staggered so that adjacent windows do not have the same axial dimensions.

Referring now to FIG. 37 and FIG. 39, in some embodiments, one or more inflatable segment has an orientation which includes an axial and a circumferential element, for example, in some embodiments, segments, forming a diagonal mesh inflatable wall.

In some embodiments, a workspace has a tapered tubular shape, e.g. workspace 3702 FIG. 37, 3802 FIG. 38.

In some embodiments, windows (e.g. one or more of windows 3750, 3850, 3950) include transparent material. In some embodiments, one or more window is a gap, where, in some embodiments, containment is provided by an additional bag into which the workspace device is placed and/or in which the workspace is provided. In some embodiments, a workspace within an external bag is connected to the bag.

General

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

In particular, it is noted that the various species of closure systems, sealing systems, rigidifying systems and safety features are intended to be used with embodiments other than the specific ones used to exemplify them. Furthermore, many of the features described herein can be used to improve prior art designs. For example, safety measures may be used with existing retrieval bag designs.

It is expected that during the life of a patent maturing from this application many relevant tissue reduction technologies will be developed and the scope of the term morcellator is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A workspace device configured to create a protected space within a cavity of a patient body, comprising:
a workspace body having a workspace inner wall defining an internal volume of said workspace body, including a plurality of inflatable segments, and a rim portion defining a single opening to said internal volume and configured to be pulled out from a body cavity while the rest of said workspace body remains in said workspace body, said workspace body formed of a flexible material such that it is:
collapsible to a collapsed state where said workspace body fits through a passageway; and
expandable, to increase said internal volume, to an expanded state within said cavity, by inflation of said inflatable segments, and wherein in said expanded state, said workspace body extends distally from said rim portion defining said single opening in a distal direction defining a workspace axis;
one or more channels sized and shaped to supply inflation fluid to said inflatable segments of said workspace body;
wherein said inflatable segments comprise vertical segments extending axially along said workspace axis, wherein when inflated said inflatable segments expand said workspace device; and
wherein inflation through said one or more channels expands said inflatable segments to said expanded state, where, in said expanded state and while said rim portion is pulled out from the patient body, said inflatable segments rigidize said workspace body to resist collapse by intra-abdominal forces.

2. The workspace device according to claim 1, wherein said rim portion is attached to an elongate handle sized and shaped to extend through said laparoscopic passageway outside of said cavity.

3. The workspace device according to claim 1, wherein one or more of said segments has a reduced axial dimension portion, forming a window between axially adjacent segments.

4. The workspace device according to claim 1, wherein one or more of said inflatable segments have a ring shaped lumen.

5. The workspace device according to claim 4, wherein:
one or more of said inflatable segments is toroidal in shape with a circular cross section; or
one or more of said inflatable segments has an elliptical cross section; or
one or more of said inflatable segments has a semicircular cross section; or
one or more of said inflatable segments has cross section with changing dimensions.

6. The workspace device according to claim 1, comprising a reinforced base portion connected to a distal end of said body.

7. The workspace device according to claim 1, wherein each of said inflatable segments is pre-formed from two tubular sheets of material adhered to each other.

8. The workspace device according to claim 1, wherein said passageway is a laparoscopic passageway in an abdominal wall.

9. The workspace device according to claim 8, wherein a fluid pathway from at least one channel of said one or more channels is connected to a first segment before one or more other segments in the fluid pathway, defining a predetermined order of inflations of said segments.

10. The workspace device according to claim 8, wherein at least one inflatable segment is fluidly connected to one or more adjacent inflatable segments.

11. The workspace device according to claim 10, wherein each segment is fluidly connected to axially adjacent segments.

12. The workspace device according to claim 8, wherein said workspace device has a deployed configuration, where said workspace body is expanded from said collapsed configuration in an axial direction.

13. The workspace device according to claim 12, wherein said rim portion comprises an elastic element configured to elastically relax to transfer said workspace device from said collapsed configuration to said deployed configuration.

14. The workspace device according to claim 8, wherein said plurality of inflatable segments comprise circumferentially extending segments.

15. The workspace device according to claim 8, wherein said cavity is an abdominal cavity, and wherein inflation through said one or more channels expands said inflatable segments to said expanded state, where, in said expanded state and while said rim portion is pulled out from the body, said internal volume is isolated from said abdominal cavity.

16. The workspace device according to claim 1, comprising at least one sensor configured to detect proximity of a metal tool to a surface of said workspace device.

17. A method of processing tissue in a laparoscopic manner, comprising:
inserting to an abdominal cavity of a patient body, a collapsed workspace device having a wall defining an internal volume, a rim portion defining a single opening to said internal volume and plurality of vertical inflatable segments;
bringing tissue from said abdominal cavity into said workspace device through said single opening of said workspace device;
expanding the workspace device to define a workspace volume therein by inflating said plurality of vertical inflatable segments of said workspace device while said single opening of said workspace device is in said abdominal cavity, wherein an inflated segment of said vertical inflatable segments is configured to press on adjacent vertical inflatable segments to expand said workspace device;
isolating said tissue from said abdominal cavity by pulling out said single opening from said patient body.

18. The method according to claim 17, comprising increasing a pressure within said workspace volume to a pressure above a pressure within said abdominal cavity.

19. The method according to claim 17, comprising processing said tissue.

* * * * *